US008399468B2

(12) United States Patent
Cowart et al.

(10) Patent No.: US 8,399,468 B2
(45) Date of Patent: Mar. 19, 2013

(54) OCTAHYDRO-PYRROLO[3,4-B]PYRROLE DERIVATIVES

(75) Inventors: Marlon D. Cowart, Round Lake, IL (US); Chen Zhao, Libertyville, IL (US); Minghua Sun, Libertyville, IL (US); Lawrence A. Black, Libertyville, IL (US); Guo Zhu Zheng, Lake Bluff, IL (US); Robert J. Gregg, Libertyville, IL (US); Geoff G. Z. Zhang, Libertyville, IL (US); Ahmad Y. Sheikh, Deerfield, IL (US); Xiaochun Lou, Long Grove, IL (US); Rodger F. Henry, Wildwood, IL (US); David M. Barnes, Lake Villa, IL (US); Lawrence Kolaczkowski, Gurnee, IL (US); Anthony R. Haight, Wadsworth, IL (US); Sou-Jen Chang, Prairie View, IL (US); Steven J. Wittenberger, Mundelein, IL (US); Michael G. Fickes, Evanston, IL (US)

(73) Assignee: Abbott Laboratories, Abbott Park, IL (US)

( * ) Notice: Subject to any disclaimer, the term of this patent is extended or adjusted under 35 U.S.C. 154(b) by 234 days.

(21) Appl. No.: 12/715,660

(22) Filed: Mar. 2, 2010

(65) Prior Publication Data
US 2010/0222358 A1 Sep. 2, 2010

Related U.S. Application Data

(62) Division of application No. 11/674,518, filed on Feb. 13, 2007, now Pat. No. 7,728,031.

(60) Provisional application No. 60/776,509, filed on Feb. 24, 2006.

(51) Int. Cl.
*A61K 31/501* (2006.01)
*C07D 403/10* (2006.01)

(52) U.S. Cl. ............... 514/252.06; 544/224; 544/238; 514/252.01

(58) Field of Classification Search .............. 544/224, 544/238; 514/252.01, 252.06
See application file for complete search history.

(56) References Cited

U.S. PATENT DOCUMENTS

| | | | |
|---|---|---|---|
| 5,071,999 A | 12/1991 | Schenke et al. | |
| 7,462,599 B2 | 12/2008 | Schilling et al. | |
| 7,727,953 B2* | 6/2010 | Tolle et al. | 514/13.3 |
| 7,728,031 B2 | 6/2010 | Cowart et al. | |
| 7,745,448 B2* | 6/2010 | Mellican et al. | 514/260.1 |
| 8,026,240 B2* | 9/2011 | Cowart et al. | 514/252.03 |
| 8,124,644 B2* | 2/2012 | Levi | 514/411 |
| 2004/0092521 A1 | 5/2004 | Altenbach et al. | |
| 2005/0101602 A1 | 5/2005 | Basha et al. | |
| 2005/0245543 A1 | 11/2005 | Howard et al. | |
| 2006/0019998 A1 | 1/2006 | Wager et al. | |
| 2008/0221093 A1 | 9/2008 | Gege et al. | |
| 2009/0105267 A1 | 4/2009 | Cowart et al. | |

FOREIGN PATENT DOCUMENTS

| | | |
|---|---|---|
| DE | 3231088 A1 | 3/1983 |
| EP | 393424 B1 | 9/1995 |
| EP | 350733 B1 | 8/1997 |
| WO | WO9635691 A1 | 11/1996 |
| WO | WO0024719 A1 | 5/2000 |
| WO | WO0166534 A2 | 9/2001 |
| WO | WO0181347 A2 | 11/2001 |
| WO | WO0206223 A1 | 1/2002 |
| WO | WO0206278 A1 | 1/2002 |
| WO | WO0240461 A2 | 5/2002 |
| WO | WO02070523 A1 | 9/2002 |
| WO | WO02072093 A2 | 9/2002 |
| WO | WO2004092173 A2 | 10/2004 |
| WO | WO2004097408 A1 | 11/2004 |
| WO | WO2005054194 A1 | 6/2005 |
| WO | WO2005056056 A2 | 6/2005 |
| WO | WO2005075479 A1 | 8/2005 |
| WO | WO2006018280 A2 | 2/2006 |
| WO | WO2007007069 A1 | 1/2007 |
| WO | WO2007027734 A2 | 3/2007 |
| WO | WO2007093363 A1 | 8/2007 |
| WO | WO2007093364 A1 | 8/2007 |
| WO | WO2007100990 A2 | 9/2007 |
| WO | WO2007110868 A2 | 10/2007 |
| WO | WO2008005338 A1 | 1/2008 |
| WO | WO2008014240 A2 | 1/2008 |
| WO | WO2008023239 A1 | 2/2008 |
| WO | WO2008024978 A2 | 2/2008 |
| WO | WO2008041090 A1 | 4/2008 |
| WO | WO2008059238 A1 | 5/2008 |
| WO | WO2008153958 A2 | 12/2008 |
| WO | WO2009036132 A1 | 3/2009 |

OTHER PUBLICATIONS

Abdel-Magid, et al., "Reductive Amination of Aldehydes and Ketones with Sodium Triacetoxyborohydride. Studies on Direct and Indirect Reductive Amination Procedures," Journal of Organic Chemistry, 1996, vol. 61 (11), pp. 3849-3862.

Airaksinen, et al., "Histamine Neurons in Human Hypothalamus: Anatomy in Normal and Alzheimer Diseased Brains," Neuroscience, 1991, vol. 44 (2), pp. 465-481.

Aranyos, et al., "Novel Electron-Rich Bulky Phosphine Ligands Facilitate the Palladium-Catalyzed Preparation of Diaryl Ethers," Journal of the American Chemical Society, 1999, vol. 121, pp. 4369-4378.

Arrang, et al., "Auto-inhibition of Brain Histamine Release Mediated by a Novel Class ($H_3$) of Histamine Receptor," Nature, 1983, vol. 302, pp. 832-837.

Arrang, et al., "Highly Potent and Selective Ligands for Histamine $H_3$-Receptors," Nature, 1987, vol. 327, pp. 117-123.

(Continued)

*Primary Examiner* — Golam M M Shameem
(74) *Attorney, Agent, or Firm* — Lisa V. Mueller; Michael Best & Friedrich LLP

(57) ABSTRACT

Octahydro-pyrrolo[3,4-b]pyrrole derivatives are useful in treating conditions or disorders prevented by or ameliorated by histamine-3 receptor ligands. Octahydro-pyrrolo[3,4-b] pyrrole compounds, methods for using such compounds, compositions for making them, and processes for preparing such compounds are disclosed herein.

14 Claims, 5 Drawing Sheets

OTHER PUBLICATIONS

Barbier, et al., "Acute Wake-Promoting Actions of JNJ-5207852, a Novel, Diamine-based $H_3$ Antagonist," British Journal of Pharmacology, 2004, vol. 143, pp. 649-661.

Bates, et al., "High-Yield Benzyne Synthesis of Diaryl Ethers," Journal of Organic Chemistry, 1982, vol. 47, pp. 4374-4376.

Bernaerts, et al., "Histamine H3 Antagonist Thioperamide Dose-Dependently Enhances Memory Consolidation and Reverse Amnesia Induced by Dizocilpine or Scopolamine in a One-Trail Inhibitory Avoidance Task in Mice," Behavioural Brain Research, 2004, vol. 154, pp. 211-219.

Bjenning, et al., "Peripherally Administered Ciproxifan Elevates Hypothalmic Histamine Levels and Potently Reduces Food Intake in the Sprague Dawley Rat" in: Histamine Research in the New Mellennium, Watanabe T., et al., eds., Elsevier Science, 2001, pp. 449-450.

Black, et al., "2, 3-Diarylcyclopentenones as Orally Active, Highly Selective Cyclooxygenase.2 Inhibitors," Journal of Medicinal Chemistry, 1999, vol. 42, pp. 1274-1281.

Browman, et al., "Enhancement of Prepulse Inhibition of Startle in Mice by the H3 Receptor Antagonists Thioperamide and Ciproxifan," Behavioural Brain Research, 2004, vol. 153 (1), pp. 69-76.

Burns, et al., "PET Ligands for Assessing Receptor Occupancy in Vivo," Annual Reports in Medicinal Chemistry, 2001, vol. 36, pp. 267-276.

Burns, et al., "Positron Emission Tomography Neuroreceptor Imaging as a Tool in Drug Discovery, Research and Development," Current Opinion in Chemical Biology, 1999, vol. 3 (4), pp. 388-394.

Carroll, et al., "Synthesis, Nicotinic Acetylcholine Receptor Binding, and Antinociceptive Properties of 2- exo '2-(2'-Substituted 5'-pyridinyl)-7-azabicyclo[2.2.1]heptanes. Epibatidine Analogues," Journal of Medicinal Chemistry, 2001, vol. 44, pp. 2229-2237.

Chavez, et al., "Histamine ($H_3$) Receptors Modulate the Excitatory Amino Acid Response of the Vestibular Afferents," Brain Research, 2005, vol. 1064, pp. 1-9.

Chen, et al., "Effects of Histamine on MK-801-induced Memory Deficits in Radial Maze Performance in Rats," Brain Research, 1999, vol. 839, pp. 186-189.

Chen, et al., "Pharmacological Effects of Carcinine on Histaminergic Neurons in the Brain," British Journal of Pharmacology, 2004, vol. 143, pp. 573-580.

Clapham, et al., "Thioperamide, the Selective Histamine $H_3$ Receptor Antagonist, Attenuates Stimulant Induced Locomotor Activity in the Mouse," European Journal of Pharmacology, 1994, vol. 259 (2), pp. 107-114.

Cowart, et al., "4-(2-[2-(2(R)- Methylpyrrolidin-1-yl) ethyl] Benzofuran-5yl) Benzonitrile and Related 2-Aminoethylbenzofuran $H_3$ Receptor Antagonists Potently Enhance Cognition and Attention," Journal of Medicinal Chemistry, 2005, vol. 48 (1), pp. 38-55.

Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Dealmeida, et al., "Memory Facilitation by Histamine," Archives Internationales De Physiologie Et De Biochimie, 1986, vol. 283 (2), pp. 193-198.

Delaunois, et al., "Modulation of Acetylcholine, Capsaicin and substance P Effects by Histamine $H_3$ Receptors in Isolated Perfused Rabbit Lungs," European Journal of Pharmacology, 1996, vol. 277 (2-3), pp. 243-250.

Dimitriadou, et al., "Functional Relationship Between Mast Cells and C-Sensitive Nerve Fibres Evidenced by Histamine $H_3$ Receptor Modulation in Rat Lung and Spleen," Clinical Science, 1994, vol. 87, pp. 151-163.

Dumery, et al., "Development of Amygdaloid Cholinergic Mediation of Passive Avoidance Learning in the Rat," Experimental Brain Research, 1987, vol. 67(1), pp. 61-69.

Dvorak, et al., "4-Phenoxypiperidines: Potent, Conformationally Restricted, non-Imidazole Histamine $H_3$ Antagonists," Journal of Medicinal Chemistry, 2005, vol. 48 (6), pp. 2229-2238.

Esbenshade, et al., "Pharmacological and Behavioral Properties of A-349821, a Selective and Potent Human Histamine $H_3$ Receptor Antagonist," Biochemical Pharmacology, 2004, vol. 68 (5), pp. 933-945.

Esbenshade, et al., "Pharmacological Properties of ABT-239 [4-(2-{2-[(2R)-2-Methylpyrrolidinyl]ethyl}-benzofuran-5-yObenzonitrile]: 1. Potent and Selective Histamine $H_3$ Receptor Antagonist with Drug-Like Properties," Journal of Pharmacology and Experimental Therapeutics, 2005, vol. 313 (1), pp. 165-175.

Fitzsimons, et al., "Histamine Receptors Signaling in Epidermal Tumor Cell Lines with H-Ras Gene Alterations," Inflammation Research, 1998, vol. 47 (1), pp. S50-S51.

Fox, et al., "Effects of Histamine $H_3$ Receptor Ligands GT2331 and Ciproxifan in a Repeated Acquisition Response in the Spontaneously Hypertensive Rat Pup," Behavioural Brain Research, 2002, vol. 131 (1-2), pp. 151-161.

Fox, et al., "Identification of Novel $H_3$ Receptor ($H_3$R) Antagonists with Cognition Enhancing Properties in Rats," Inflammation Research, 2003, vol. 52 (1), pp. S31-S32.

Fox, et al., "Pharmacological Properties of ABT-239 [4-(2-{2-[(2R)-2-Methylpyrrolidinty]ethyl}-benzofuran-5-yl)benzonitrile]-: II Neurophysiological Characterization and Broad Preclinical Efficacy in Cognition and Schizophrenia of a Potent and Selective Histamine $H_3$R," Journal of Pharmacology and Experimental Therapeutics, 2005, vol. 313 (1), pp. 176-190.

Fox, et al., "Two Novel and Selective Nonimidazole $H_3$ Receptor Antagonists A-304121 and A-317920: II. In Vivo Behavioral and Neurophysiological Characterization," Journal of Pharmacology and Experimental Therapeutics, 2003, vol. 305 (3), pp. 897-908.

Furniss, et al., Vogel's Textbook of Practical Organic Chemistry, 5th Edition, Longman Scientific & Technical, 1989, Table of Contents.

Glase, et al., "Attention Deficit Hyperactivity Disorder: Pathophysiology and Design of New Treatments," Annual Reports in Medicinal Chemistry, 2002, vol. 37, pp. 11-20.

Greene, et al., Protective Groups in Organic Synthesis, 3rd Edition, John Wiley and Sons, Inc., 1999, Table of Contents.

Greene, et al., "Protection for the Amino Group," Protective Groups in Organic Synthesis, 1999, Third Edition, pp. 494-653.

Haas, et al., "Subcortical Modulation of Synaptic Plasticity in the Hippocampus," Behavioural Brain Research, 1995, vol. 66 (1-2), pp. 41-44.

Haga, et al., "Mechanisms of the Photochemical Rearrangement of Diphenyl Ethers," Journal of Organic Chemistry, 1996, vol. 61 (2), pp. 735-745.

Halpern, M., "GT-2331," Current Opinion in Central and Peripheral Nervous System Investigational Drugs, vol. 1, pp. 524-527, 1999.

Hancock, et al., "Antiobesity Effects of A-331440, a Novel Non-Imidazole Histamine $H_3$ Receptor Antagonist," European Journal of Pharmacology, 2004, vol. 487 (1-3), pp. 183-197.

Hancock, et al., "Histamine $H_3$ Antagonists in Models of Obesity," Inflammatory Research, 2004, vol. 53 (Suppl. 1), pp. S47-S48.

Harada, et al., "Inhibitory Effect of Iodophenpropit, a Selective Histamine $H_3$ Antagonist, on Amygdaloid Kindled Seizures," Brain Research Bulletin, 2004, vol. 63 (2), pp. 143-146.

Hartwig, et al., "Room-Temperature Palladium-Catalyzed Amination of Aryl Bromides and Chloride and Extended Scope of Aromatic C-N Bond Formation with a Commercial Ligand," Journal of Organic Chemistry, 1999, vol. 64 (15), pp. 5575-5580.

Hartwig, et al., "Transition Metal Catalyzed Synthesis of Arylamines and Aryl Ethers from Aryl Halides and Triflates: Scope and Mechanism," Angewandte Chemie International Edition, 1998. 37, pp. 2046-2067.

Hietala, J., "Ligand-Receptor Interactions as Studied by PET: Implications for Drug Development," Annals of Medicine, 1999, vol. 31 (6), pp. 438-443.

Higuchi, et al., eds., Pro-drugs as Novels Delivery Systems, vol. 14, ACS Symposium Series, 1975, Table of Contents.

Hriscu, et al., "Experimental Evaluation of the Analgesic Efficacy of Some Antihistamines as Proof of the Histaminergic Receptor Involvement in Pain," Famacia, 2001, vol. 49 (2), pp. 23-30.

Huang, et al., "Effect of the Histamine $H_3$-antagonist Clobenpropit on Spatial Memory Deficits Induced by MK-801 as Evaluated by Radial Maze in Sprague-Dawley Rats," Behavioural Brain Research, 2004, vol. 151 (1-2), pp. 287-293.

Huck, et al., "The Identification of Pyrimidine Diazabicyclo[3.3.0]Octane Derivatives as 5HT2C Receptor Agonists," Bioorganic & Medicinal Chemistry Letters, 2006, vol. 16 (11), pp. 2891-2894.
International Search Report for Application No. PCT/US2007/062329, mailed on Aug. 29, 2007, 4 pages.
Ishiyama, et al., "Synthesis of Pinacol Arylboronates via Cross-coupling Reaction of bis(pinacolato)diburon with Chloroarenes Catalyzed by Palladium(0)-tricyclohexylphosphine Complexes," Tetrahedron, 2001, vol. 57, pp. 9813-9816.
Itoh, et al., "Thioperamide, A Histamine $H_3$ Receptor Antagonist, Powerfully Suppresses Peptide YY-Induced Food Intake in Rats," Biological Psychiatry, 1999, vol. 45 (4), pp. 475-481.
Kamei, et al., "Influence of Certain $H_3$-Blockers on the Step-Through Active Avoidance Response in Rats," Psychopharmacology, 1990, vol. 102 (3), pp. 312-318.
Kamei, et al., "Participation of Histamine in the Step-Through Active Avoidance Response and Its Inhibition by $H_1$-Blockers," Japan Journal of Pharmacology, 1991, vol. 57 (4), pp. 473-482.
Kiyomori, et al., "An Efficient Copper-Catalyzed Coupling of Aryl Halides with Imidazoles," Tetrahedron Letters, 1999, vol. 40, pp. 2657-2660.
Klapars, et al., "A General and Efficient Copper Catalyst for the Amidation of Aryl Halides and the N-Arylation of Nitrogen Heterocycles," Journal of the American Chemical Society, 2001, vol. 123, pp. 7727-7729.
Komater, et al., "H3 Receptor Blockade by Thioperamide Enhances Cognition in Rats without Inducing Locomotor Sensitization," Psychopharmacology, 2003, vol. 167 (4), pp. 363-372.
Krueger, et al., "G Protein-Dependent Pharmacology of Histamine $H_3$ Receptor Ligands: Evidence for Heterogeneous Active State Receptor Conformations," Journal of Pharmacology and Experimental Therapeutics, 2005, vol. 314 (1), pp. 271-281.
Kuwabe, et al., "Palladium-Catalyzed Intramolecular C-O Bond Formation," Journal of the American Chemical Society, 2001, vol. 123 (49), pp. 12202-12206.
Kwong, et al., "Copper-Catalyzed Coupling of Alkylamines and Aryl Iodides: An Efficient System Even in an Air Atmosphere," Organic Letters, 2002, vol. 4, pp. 581-584.
Lamberti, et al., "Antidepressant-like Effects of Endogenous Histamine and of Two Histamine $H_1$ Receptor Agonists in the Mouse Forced Swim Test," British Journal of Pharmacology, 1998, vol. 123 (7), pp. 1331-1336.
Letsinger, et al., "Organoboron Compounds. IX. 8-Quinolineboronic Acid, its Preparation and Influence on Reactions of Chlorohydrins," Journal of the American Chemical Society, 1959, vol. 81, pp. 498-501.
Leurs, et al., eds., "The Histamine $H_3$ Receptor: A Target for New Drugs," vol. 30, Elsevier Science B.V., 1998, Table of Contents.
Leurs, et al., "Histamine Homologues Discriminating between Two Functional $H_3$-Receptor Assays, Evidence for $H_3$ Receptor," Journal of Pharmacology and Experimental Therapeutics, 1996, vol. 276 (3), pp. 1009-1015.
Leurs, et al., The Histamine $H_3$-Receptor: A Target For Developing New Drugs, Elsevier Science, 1998, vol. 39, pp. 127-165.
Leurs, et al., "The Medicinal Chemistry and Therapeutic Potentials of Ligands of the Histamine $H_3$ Receptor," Progress in Drug Research, 1995, vol. 45, pp. 107-165.
Leurs, et al., The Histamine $H_3$-Receptor: Frome Gene Cloning to $H_3$ Receptor Drugs: Native Reviews Drug Discovery, 2005, vol. 4, pp. 107-120.
Li, et al., "Highly Active, Air-Stable Versatile Palladium Catalysts for the C-C, C-N, and C-S Bond Formations Via Cross-Coupling Reactions of Aryl Chlorides," The Journal of Organic Chemistry, 2001, vol. 66 (25), pp. 8677-8681.
Li, et al., "The First Phosphine Oxide Ligand Precursors for Transition Metal Catalyzed Cross-Coupling Reactions: C-C, C-N, and C-S Bond Formation on Unactivated Aryl Chlorides," Angewandte Chemie International Ed, 2001, vol. 40 (8), pp. 1513-1516.
Ligneau, et al., "Neurochemical and Behavioral Effects of Ciproxifan, a Potent Histamine $H_3$-Receptor Antagonist," Journal of Pharmacology and Experimental Therapeutics, 1998, vol. 287 (2), pp. 658-666.

Lin, et al., "Involvement of Histaminergic Neurons in Arousal Mechanisms Demonstrated with $H_3$-Receptor Ligands in the Cat," Brain Research, 1990, vol. 523 (2), pp. 325-330.
Liu, et al., "Novel—Arylthio Cinnamides as Antagonists of Leukocyte Function-Associated Antigen- 1/Intracellular Adhesion Molecule-1 Interaction. 2. Mechanism of Inhibition and Structure-Based Improvement of Pharmaceutical Properties," The Journal of Medicinal Chemistry, 2001, vol. 44 (8), pp. 1202-1210.
Lozada, et al., "Plasticity of Histamine $H_3$ Receptor Expression and Binding in the Vestibular Nuclei After Labyrinthectomy in Rat," Biomedical Center Neuroscience, 2004, vol. 5, pp. 32.
Malmberg-Aiello, et al., "Role of Histamine in Rodent Antinociception," British Journal of Pharmacology, 1994, vol. 111 (4), pp. 1269-1279.
Malmlof, et al., "Influence of a Selective Histamine $H_3$ Receptor Antagonist on Hypothalamic Neural Activity, Food Intake and Body Weight," International Journal of Obesity, 2005, vol. 29, pp. 1402-1412.
Mann, et al., "Palladium-Catalyzed Formation of Diarl Ethers from Aryl Bromides. Electron Poor Phosphines Enhance Reaction Yields," Tetrahedron Letters, 1997, vol. 38 (46), pp. 8005-8008.
Marcoux, et al., "A General Copper-Catalyzed Synthesis of Diaryl Ethers," Journal of the American Chemical Society, 1997, vol. 119, pp. 10539-10540.
Mazurkiewicz-Kwilecki, et al., "Changes in the Regional Brain Histamine and Histidine Levels in Postmortem Brains of Alzheimer Patients," Canadian Journal of Physiology and Pharmacology, 1989, vol. 67 (1), pp. 75-78.
McLeod, et al., "Combined Histamine $H_1$ and $H_3$ Receptor Blockade Produces Nasal Decongestion in an Experimental Model of Nasal Congestion," American Journal of Rhinology, 1999, vol. 13 (5), pp. 391-399.
McLeod, et al., "Histamine $H_3$ Antagonists," Progress in Respiratory Research, 2001, vol. 31, pp. 133-136.
Meguro, et al., "Effects of Thioperamide, a Histamine $H_3$ Antagonist, on the Step-Through Passive Avoidance Response and Histidine Decarboxylase Activity in Senescence-Accelerated Mice," Pharmacology, Biochemistry and Behavior, 1995, vol. 50 (3), pp. 321-325.
Miyaura, et al., "Palladium-Catalyzed Cross-Coupling Reactions of Organoboron Compounds," Chemical Reviews, 1995, vol. 95 (7), pp. 2457-2483.
Monti, et al., "Sleep and Waking During Acute Histamine $H_3$ Agonist BP2.94 or $H_3$ Antagonist Carboperamide (MR 16155) Administration in Rats," Neuropsychopharmacology, 1996, vol. 15 (1), pp. 31-35.
Monti, et al., "Effects of Selective Activation or Blockade of the Histamine $H_3$ Receptor on Sleep and Wakefulness," Journal of Pharmacology, 1991, vol. 205, pp. 283-287.
Morisset, et al., "Atypical Neuroleptics Enhance Histamine Turnover in Brain Via 5-Hydroxytryptamino$_{2A}$ Receptor Blockade," Journal of Pharmacology and Experimental Therapeutics, 1999, vol. 288 (2), pp. 590-596.
Murakami, et al., "AQ-0145, A Newly Developed Histamine $H_3$ Antagonist, Decreased Seizure Susceptibility of Electrically Induced Convulsions in Mice," Methods and Findings in Experimental and Clinical Pharmacology, 1995, vol. 17 Suppl. C, pp. 70-73.
Olivera, et al., "Dibenzoxepino[4,5-d]Pyrazoles: A Facile Approach Via the Ullmann-Ether Reaction," Tetrahedron Letters, 2000, vol. 41, pp. 4353-4356.
O'Neill, et al., "Pharmacological Evaluation of the In Vivo Model of Vestibular Dysfunction in the Rat," Methods and Findings in Experimental and Clinical Pharmacology, 1999, vol. 21 (4), pp. 285-289.
O'Neill, et al., "Total Synthesis of (±)-Cytisine," Organic Letters, 2000, vol. 2 (26), pp. 4201-4204.
Onodera, et al., "Improvement by FUB 181, A Novel Histamine $H_3$-Receptor Antagonist, of Learning and Memory in the Elevated Plus-Maze Test in Mice," Naunyn-Schmiedebergs' Archives of Pharmacology, 1998, vol. 357 (5), pp. 508-513.
Onodera, et al., "Neuropharmacology of the Histaminergic Neuron System in the Brain and its Relationship with Behavioral Disorders," Progress in Neurobiology, 1994, vol. 42 (6), pp. 685-702.

Opposition document received in Costa Rican counterpart Application No. PCT/US2007/0623329; File No. 10287, dated Mar. 13, 2009. (English translation).

Opposition documents received in Ecuadorian counterpart Application No. SP-08-08687 PCT, dated Feb. 5, 2009.

Pagliara, et al., "Molecular Properties and Pharmacokinetic Behavior of Cetirizine, a Zwitterionic $H_3$-Receptor Antagonist," J. Med. Chem. vol. 41, pp. 853-863, 1998.

Palomo, et al., "Phosphazene Bases for the Preparation of Biaryl Thioethers from Aryl Iodides and Arenethiols," Tetrahedron Letters, 2000, vol. 41, pp. 1283-1286.

Palucki, et al., "Palladium-Catalyzed Intermolecular Carbon-Oxygen Bond Formation: A New Synthesis of Aryl Ethers," Journal of the American Chemical Society, 1997, vol. 119, pp. 3395-3396.

Pan, et al., "Histaminergic Ligands Attenuate Barrel Rotation in Rats Following Unilateral Labyrinthectomy," Methods and Findings in Experimental and Clinical Pharmacology, 1998, vol. 20 (9), pp. 771-777.

Panula, et al., "Neuronal Histamine Deficit in Alzheimer's Disease," Neuroscience, 1998, vol. 82 (4), pp. 993-997.

Passani, et al., "Central Histaminergic System and Cognition," Neuroscience and Biobehavioral Reviews, 2000, vol. 24 (1), pp. 107-113.

Perez-Garcia, et al., "Effects of Histamine $H_3$ Receptor Ligands in Experimental Models of Anxiety and Depression," Psychopharmacology, 1999, vol. 142 (2), pp. 215-220.

Poste, et al., "Lipid Vesicles as Carriers for Introducing Biologically Active Materials into Cells," Methods in Cell Biology, 1976, vol. 14, pp. 33-71.

Prast, et al., "Histaminergic Neurons Facilitate Social Memory in Rats," Brain Research, 1996, vol. 734 (1-2), pp. 316-318.

Pu, et al., "An Efficient Copper-Catalyzed N-Arylation of Pyridazinones with a Structurally Well-Defined Copper Complex," Tetrahedron Letters, 2006, vol. 47 (2), pp. 149-153.

Pu, et al., "A Facile and Scaleable Synthesis of ABT-239, A Benzofuranoid $H_3$ Antagonist," Organic Process Research and Development, 2005, vol. 9, pp. 45-50.

Roche, E., Bioreversible Carries in Drug Design Theory and Application, Pergamon Press, 1987, Table of Contents.

Rodrigues, et al., "Interaction of Clozapine with the Histamine $H_3$ Receptor in Rat Brain," British Journal of Pharmacology, 1995, vol. 114 (8), pp. 1523-1524.

Sakai, et al., "Effects of Thioperamide, a Histamine $H_3$ Receptor Antagonist, on Locomotor Active and Brain Histamine Content in Mast Cell-Deficient W/W$^V$ Mice," Life Sciences, 1991, vol. 48 (25), pp. 2397-2404.

Sakata, et al., "Hypothalamic Neuronal Histamine Modulates Ad Libitum Feeding by Rats," Brain reasearch, 1990, vol. 537 (1-2), pp. 303-306.

Sanchez-Lemus, et al., "Histamine H·Receptor Activation Inhibits Dopamine $D_1$ Receptor-Induced Camp Accumulation in Rat Striatal Slices," Neuroscience Letters, 2004, vol. 364 (3), pp. 179-184.

Satoh, et al., "Regioselective Arylation Reactions of Biphenyl-2-0Ls, Naphthols, and Benzylic Compounds With Aryl Halides Under Palladium Catalysis," Bulletin of the Chemical Society of Japan, 1998, vol. 71 (9), pp. 2239-2246.

Schopfer, et al., "A General Palladium-Catalysed Synthesis of Aromatic and Heteroaromatic Thioethers," Tetrahedron, 2001, vol. 57, pp. 3069-3073.

Schwartz, et al., "Histamine", in: Psychopharmacology: The Fourth Generation of Progess, Chapter 35, Bloom F.E., et al., eds., Raven Press, 1995, pp. 397-405.

Schweitzer et al., "Drugs Under Investigation for Attention-Deficit Hyperactivity Disorder," Current Opinion in Investigational Drugs, 2002, vol. 3 (8), pp. 1207-1211.

Shaywitz, et al., "Dopaminergic But Not Noradrenergic Mediation of Hyperactivity and Performance Deficits in the Developing Rat Pup," Psychopharmacology, 1984, vol. 82 (1-2), pp. 73-77.

Sindkhedkar, et al., "Aromatic Interactions of the Synthesis and Conformation of Two Collapsible Tetracationic Cyclophanes," Tetrahedron, 2001, vol. 57, pp. 2991-2996.

Sugahara, et al., "A Facile Copper-Catalyzed Ullmann Condensation: N-Arylation of Heterocyclic Compounds Containing an -NHCO- Moiety," Chemical & Pharmaceutical Bulletin, 1997, vol. 45, pp. 719-721.

Szelag, A., "Role of Histamine $H_3$-Receptors in the Proliferation Neoplastic Cells in Vitro," Medical Science Monitor, 1998, vol. 4 (5), pp. 747-755.

Takagi, et al., "Iridium-Catalyzed C-H Coupling Reaction of Heteroaromatic Compounds with Bis(Pinacolato)Diboron: Regioselective Synthesis of Heteroarylboronates," Tetrahedron Letters, 2002, vol. 43, pp. 5649-5651.

Tedford, et al., "Pharmacological Characterization of Gt-2016, A Non-Thiourea-Containing Histamine $H_3$ Antagonist: in Vitro and in Vivo Studies," The Journal of Pharmacology and Experimental Therapeutics, 1995, vol. 275 (2), pp. 598-604.

Tedford, et al., "Cognition and Locomotor Activity in the Developing Rat: Comparisons of Histamine $H_3$ Receptor Antagonists and ADHD Therapeutics," Society for Neuroscience Abstract, vol. 22, pp. 22, 1996.

Torraca, et al., "A High-Yield, General Method for the Catalytic Formation of Oxygen Heterocycles," Journal of the American Chemical Society, 2000, vol. 122 (51), pp. 12907-12908.

Torraca, et al., "An Efficient Intermolecular Palladium-Catalyzed Synthesis of Aryl Ethers," Journal of the American Chemical Society, 2001, vol. 123 (43), pp. 10770-10771.

Tozer, et al., "Histamine $H_3$ Receptor Antagonists," Expert Opnion Therapeutic Patents, 2000, vol. 10 (7), pp. 1045-1055.

Tsuji, J., "Palladium Reagents and Catalysts, Innovations in Organic Synthesis," John Wiley & Sons, 1995, Table of Contents.

Vohora, et al., "Thioperamide, A Selective Histamine $H_3$ Receptor Antagonist, Protects Against PTZ-Induced Seizures in Mice," Life Sciences, 2000, vol. 66 (22), pp. PL297-PL301.

Wada, et al., "Is the Histaminergic Neuron System a Regulatory Center for Whole-Brain Activity?" Trends in Neurosciences, 1991, vol. 14 (9), pp. 415-418.

Wang, et al., "Design and Synthesis of Ether Analogues as Potent and Selective $M_2$ Muscarinic Receptor Antagonists," Bioorganic and Medicinal Chemistry Letters, 2001, vol. 11 (7), pp. 891-894.

Wolfe, et al., "Rational Development of Practical Catalysts for Aromatic Carbon-Nitrogen Bond Formation," Accounts of Chemical Research, 1998, vol. 13, pp. 805-818.

Wolfe, et al., "Simple, Efficient Catalyst System for the Palladium-Catalyzed Amination of Aryl Chlorides, Bromides, and Triflates," Journal of Organic Chemistry, 2000, vol. 65 (4), pp. 1158-1174.

Yamamoto, et al., "Ullmann Condensation Using Copper or Copper Oxide as the Reactant. Arylation of Active Hydrogen Compound (Imides, Amides, Amines, Phenol, Benzoic Acid, and Phenylacetylene)," Canadian Journal of Chemistry, 1983, vol. 61, pp. 86-91.

Yang, et al., "Palladium-catalyzed Amination of Aryl Halides and Sulfonates," Journal of Organometallic Chemistry, 1999, vol. 576, pp. 125-146.

Yates, et al., "Effects of a novel histamine $H_3$ receptor antagonist, GT2394, on food intake and weight gain in Sprague-Dawley rats," Society for Neuroscience, vol. 102 (10), pp. 219, 2000.

Yates, et al., "Identification and Pharmacological Characterization of a Series of New 1H-4-Substituted- Imidazoyl Histamine $H_3$ Receptor Ligands," Journal of Pharmacology and Experimental Therapeutics, 1999, vol. 289 (2), pp. 1151-1159.

Yawata, et al., "Role of Histaminergic Neurons in Development of Epileptic Seizures in El Mice," Brain Research, Molecular Brain Research, 2004, vol. 132 (1), pp. 13-17.

Yokoyama, et al., "Clobenpropit (Vuf-9153), a New Histamine $H_3$ Receptor Antagonist, Inhibits Electrically Induced Convulsions in Mice," European Journal of Pharmacology, 1994, vol. 260 (1), pp. 23-28.

Yokoyama, et al., "Effect of Thioperamide, a Histamine $H_3$ Receptor Antagonist on Electrically Induced Convulsions in Mice," Journal of Pharmacology, 1993, vol. 234 (1), pp. 129-133.

Yokoyama, et al., "Histamine and Seizures Implications for the Treatment of Epilepsy," CNS Drugs, 1996, vol. 5 (5), pp. 321-330.

* cited by examiner

OCTAHYDRO-PYRROLO[3,4-B]PYRROLE DERIVATIVES

This application is a divisional application of U.S. patent application Ser. No. 11/674,518, filed Feb. 13, 2007, which claims the benefit of U.S. Provisional Application Ser. No. 60/776,509, filed Feb. 24, 2006, which is herein incorporated by reference in its entirety.

BACKGROUND OF THE INVENTION

1. Technical Field

The invention relates to octahydro-pyrrolo[3,4-b]pyrrole compounds, compositions comprising such compounds, particular salts and polymorphs thereof, methods for making the compounds, salts, and polymorphs, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as the histamine-3 receptor (also sometimes called the histamine $H_3$ receptor or the $H_3$ receptor) is believed to play a role in neurotransmission in the central nervous system.

The histamine-3 ($H_3$) receptor was first pharmacologically characterized on histaminergic nerve terminals (Nature, 302: 832-837 (1983)). The histamine $H_3$ receptor is able to regulate the release of neurotransmitters in the central nervous system and peripheral nervous system, and also in peripheral organs such as the gastrointestinal tract. Histamine $H_3$ ligands have been shown to be able to modulate the release of histamine, dopamine, serotonin, acetylcholine, and other neurotransmitters. The existence of $H_3$ receptors and their established role in modulating neurotransmitter release activity in animal models of disease indicate the utility of histamine $H_3$ ligands for the treatment of disease. This has motivated a search for, and the development of, selective $H_3$ receptor agonists and antagonists ((Leurs, et al., "The histamine $H_3$ receptor: From gene cloning to $H_3$ receptor drugs" Nature Reviews Drug Discovery (2005) v. 4, p 107-120; Arrang, et al. Nature, 327:117-123 (1987); Leurs and Timmerman, ed. "The History of $H_3$ Receptor: a Target for New Drugs," Elsevier (1998)).

The activity of histamine $H_3$ receptors can be modified or regulated by the administration of histamine $H_3$ receptor ligands. The ligands can demonstrate antagonist, inverse agonist, or partial agonist activity. For example, histamine $H_3$ receptors have been linked to conditions and disorders related to the central nervous system involving memory, cognitive and other neurological processes, obesity, and also peripheral and systemic activities, such those involved in asthma and allergic rhinitis. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

Figure 1:
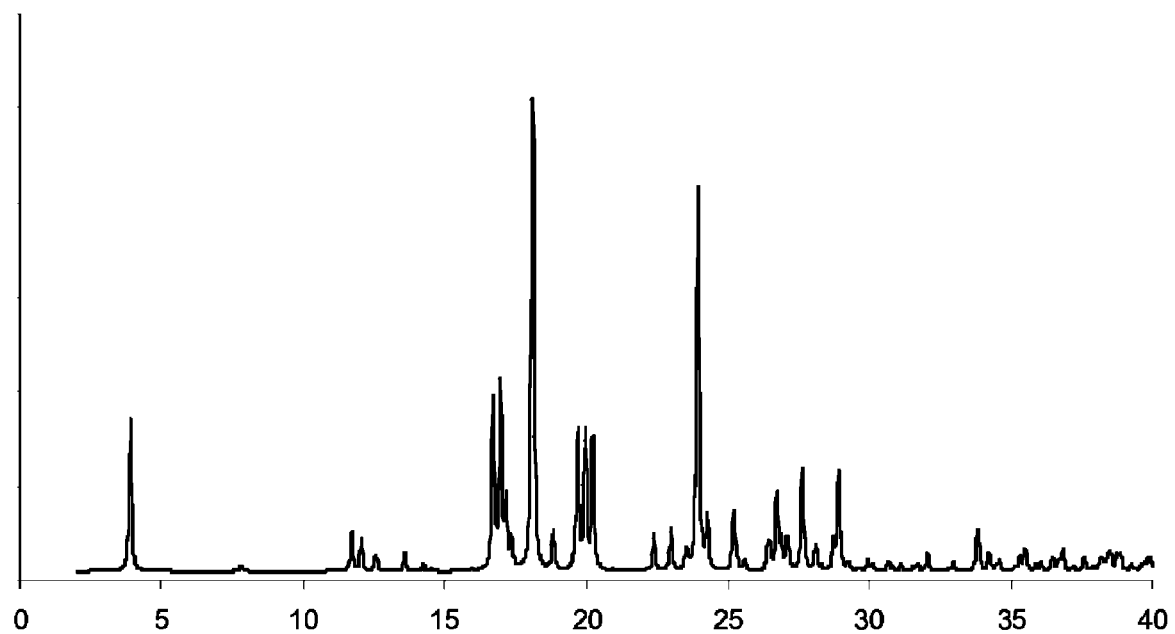
FIG. 1 is a powder X-ray diffraction pattern of a L-tartrate monohydrate Form A polymorph of 2-{4'-[(3aR,6aR)-5-methylhexahydropyrrolo[3,4-b]pyrrol-1(2H)-yl]-1,1'-biphenyl-4-yl}pyridazin-3(2H)-one.

The invention is directed to octahydro-pyrrolo[3,4-b]pyrrole derivatives and, more particularly, octahydro-pyrrolo[3,4-b]pyrrole derivatives having a compound of formula (I):

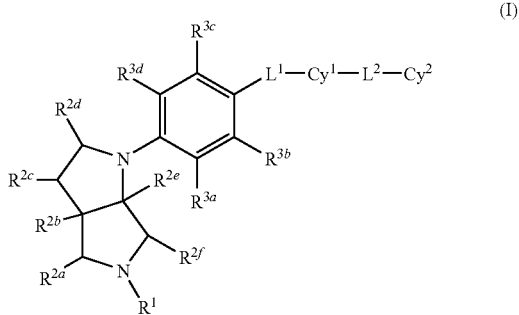

or a pharmaceutically acceptable salt, ester, amide, prodrug, or radioactive isotopic form thereof, wherein $R^1$ is alkyl, $C_3$-$C_5$ cycloalkyl, or ($C_3$-$C_5$ cycloalkyl)methyl; $R^{2a}$, $R^{2b}$, $R^{2c}$, $R^{2e}$, and $R^{2f}$ each is independently hydrogen, methyl, or fluoromethyl; $R^{3a}$, $R^{3b}$, $R^{3c}$, and $R^{3d}$ are each independently hydrogen, alkyl, fluoroalkyl, fluoroalkoxy, alkoxy, thioalkoxy, halogen, or nitrile, with the proviso that when one or more of $R^{3a}$, $R^{3b}$, $R^{3c}$, and $R^{3d}$ are alkyl, then at least one of $R^{3a}$, $R^{3b}$, $R^{3c}$, and $R^{3d}$ is fluoroalkyl, fluoroalkoxy, alkoxy, thioalkoxy, halogen, or nitrile; $L^1$ is a bond, oxygen, sulfur, carbonyl, alkylene, alkylcarbonyl, alkylamino, —C(=N—Oalkyl)-, $NR^4$, —C(=O) $NR^4$—, or —$NR^4$C(=O)—; $L^2$ is a bond, oxygen, sulfur, carbonyl, alkylene, alkylcarbonyl, alkylamino, —C(=N—Oalkyl)-, $NR^5$, —C(=O)$NR^5$—, or —$NR^5$C(=O)—; $Cy^1$ is aryl, cycloalkyl, cycloalkenyl, heteroaryl, or heterocycle; $Cy^2$ is aryl, cycloalkyl, cycloalkenyl, heteroaryl or heterocycle; $R^4$ and $R^5$ at each occurrence is hydrogen or alkyl; and provided that $Cy^2$ is not

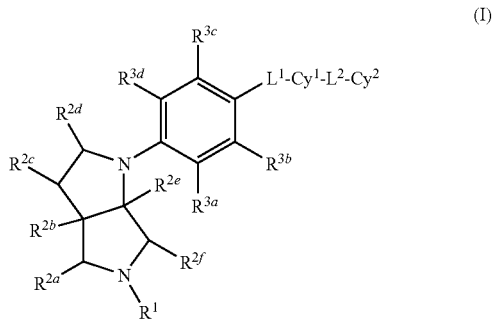

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

In addition, compounds of the invention can have the formula (II) and also demonstrate an ability modulate histamine-3 receptor activity. Compounds of formula (II) have the structure:

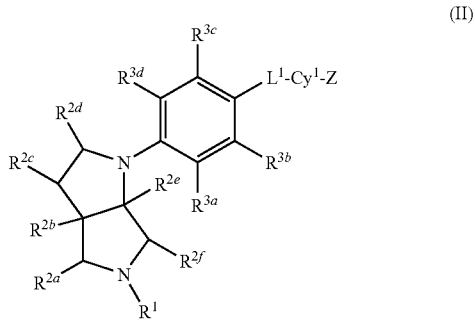

or a pharmaceutically acceptable salt, ester, amide, prodrug, or radiolabelled form thereof, wherein $R^1$ is alkyl, $C_3$-$C_5$ cycloalkyl, or ($C_3$-$C_5$ cycloalkyl)methyl; $R^{2a}$, $R^{2b}$, $R^{2c}$, $R^{2d}$, $R^{2e}$, and $R^{2f}$ each are independently hydrogen, methyl, or fluoromethyl; $R^{3a}$, $R^{3b}$, $R^{3c}$, and $R^{3d}$ each are independently hydrogen, alkyl, fluoroalkyl, fluoroalkoxy, alkoxy, thioalkoxy, halogen, or nitrile, with the proviso that when one or more of $R^{3a}$, $R^{3b}$, $R^{3c}$, and $R^{3d}$ are alkyl, then at least one of $R^{3a}$, $R^{3b}$, $R^{3c}$, and $R^{3d}$ is fluoroalkyl, fluoroalkoxy, alkoxy, thioalkoxy, halogen, or nitrile; $L^1$ is a bond, oxygen, sulfur, carbonyl, alkylene, alkylcarbonyl, alkylamino, —C(=N—Oalkyl)-, $NR^4$, —C(=O)$NR^4$—, or —$NR^4$C(=O)—; $R^4$ is hydrogen or alkyl; $Cy^1$ is aryl, cycloalkyl, cycloalkenyl, heteroaryl, or heterocycle; Z is a substituent $R^6$ or a group represented by -$L^3$-$Cy^3$; $R^6$ is hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, haloalkoxy, haloalkyl, halogen, hydroxy, hydroxyalkyl, mercapto, nitro, alkylthio, amino, $NHR^7$, $NR^7R^8$, —N($R^7$)C(=O)$R^9$, —C(=O)$NR^7R^8$, or N($R^7$)$SO_2$($R^{10}$); $L^3$ is a bond, oxygen, sulfur, carbonyl, alkylene, alkylcarbonyl, alkylamino, —C(=N—Oalkyl)-, $NR^{11}$, —C(=O)$NR^{11}$—, or —$NR^{11}$C(=O)—; $Cy^3$ is aryl, cycloalkyl, cycloalkenyl, heteroaryl, or heterocycle; $R^7$, $R^8$, $R^9$, $R^{10}$, and $R^{11}$ at each occurrence are independently hydrogen, $C_{1-4}$ alkyl, $C_3$-$C_4$ cycloalkyl, or a ($C_3$-$C_4$ cycloalkyl)amine; provided that $Cy^3$ is not

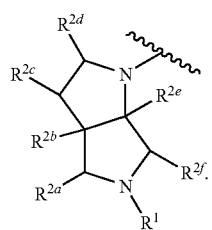

Yet another aspect of the invention relates to a method of selectively modulating $H_3$ receptor activity. The method is useful for treating, or preventing conditions and disorders related to $H_3$ receptor modulation in mammals. Such conditions and disorders include Alzheimer's disease, asthma, allergic rhinitis, attention-deficit hyperactivity disorder, bipolar disorder, cognitive dysfunction, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, metabolic syndrome, mild cognitive impairment, migraine, mood and attention alteration, motion sickness, narcolepsy, neurogenic inflammation, obesity, obsessive compulsive disorder, pain, Parkinson's disease, polycystic ovary syndrome, schizophrenia, cognitive deficits of schizophrenia, seizures, septic shock, Syndrome X, Tourette's syndrome, vertigo, and sleep disorders. More particularly, the method is useful for treating or preventing conditions and disorders related conditions and disorders related to the central nervous system involving memory, cognitive and other neurological processes, obesity, and also peripheral and systemic activities, such those involved in asthma, allergic rhinitis and obesity. Accordingly, the compounds and compositions of the invention are useful as a medicament for treating or preventing $H_3$ receptor modulated disease.

Yet another aspect of the invention relates to radiolabelled pharmaceutical compositions. Radiolabelled forms of compounds of formula (I) can be provided as compositions of the invention and administered in accordance with a method of the invention, typically for assessing or diagnosing conditions and disorders related to $H_3$ receptor activity, for example in medical imaging. More particularly, positron-emitting isotopes of compounds of the invention may be used for medical imaging in PET (positron emitting tomography), wherein the localization of histamine $H_3$ receptors, and the extent to which these receptors are occupied by ligands, can be determined. In this use, the compounds of the invention possess at least one atom of a positron-emitting radioisotope selected from $^{11}C$, $^{18}F$, $^{15}O$, and $^{13}N$. Compounds of the invention may also incorporate isotopes that useful for sPECT imaging, for example $^{123}I$. The invention also relates to particular salts and polymorphs of certain compounds of the invention as well as compositions comprising and processes for preparing such compounds, salts, and polymorphs. The invention also relates to compounds that are intermediates in processes for preparing the compounds, salts, and polymorphs described herein.

The compounds, compositions comprising the compounds, processes for making the compounds, methods for treating or preventing conditions and disorders by administering the compounds, radiolabelled forms of the compounds, particular salts of certain compounds, particularly polymorphs of certain compounds, and compositions containing such salts, polymorphs, and radiolabelled forms of the compounds are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein means a straight or branched chain hydrocarbon containing from 1 to 10 carbon atoms, and preferably 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —NH$_2$ group.

The term "aryl," as used herein, means phenyl, a bicyclic aryl, or a tricyclic aryl. The bicyclic aryl is naphthyl, a phenyl fused to a cycloalkyl, or a phenyl fused to a cycloalkenyl. The bicyclic aryl of the invention must be attached to the parent molecular moiety through any available carbon atom contained within the phenyl ring. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within a phenyl ring. Representative examples of tricyclic aryl ring include, but are not limited to, azulenyl, dihydroanthracenyl, fluorenyl, and tetrahydrophenanthrenyl.

The carbon atoms of the aryl groups of this invention are substituted with hydrogen or are optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —NR$^7$R$^8$, (NR$^7$R$^8$)carbonyl, —SO$_2$N(R$^9$)(R$^{10}$), and N(R$^9$)SO$_2$(R$^{10}$), wherein R$^7$, R$^8$ and R$^9$ are independently selected from the group hydrogen, C$_{1-4}$ alkyl, C$_3$-C$_4$ cycloalkyl, and aryl, and R$^{10}$ is selected from the group C$_{1-4}$ alkyl, C$_3$-C$_4$ cycloalkyl, and aryl. Where the aryl group is a phenyl group, the number of substituents is 0, 1, 2, 3, 4, or 5. Where the aryl group is a bicyclic aryl, the number of substituents is 0, 1, 2, 3, 4, 5, 6, 7, 8, or 9. Where the aryl group is a tricyclic aryl, the number of substituents is 0, 1, 2, 3, 4, 5, 6, 7, 8, or 9.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "carboxy" as used herein means a —CO$_2$H group.

The term "cyano" as used herein means a —CN group, attached to the parent molecular moiety through the carbon.

The term "cyanophenyl" as used herein means a —CN group appended to the parent molecular moiety through a phenyl group, including, but not limited to, 4-cyanophenyl, 3-cyanophenyl, and 2-cyanophenyl.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl. C$_3$-C$_5$ cycloalkyl in particular refers to a saturated cyclic hydrocarbon group containing from 3 to 5 carbons, for example, cyclopropyl, cyclobutyl, and cyclopentyl.

The term "cycloalkenyl" as used herein means a cyclic hydrocarbon group containing from 3 to 8 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

Each of the carbon atoms of the cycloalkyl or cycloalkenyl groups of the invention is substituted with 0, 1, or 2 substituents selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, oxo, nitro, alkylthio, —NR$^7$R$^8$, (NR$^7$R$^8$)carbonyl, —SO$_2$N(R$^9$)(R$^{10}$), and —N(R$^9$)SO$_2$(R$^{10}$), wherein, R$^7$, R$^8$, R$^9$, and R$^{10}$ are defined herein.

The term "cycloalkylcarbonyl" as used herein means a cycloalkyl group, as defined herein, appended to the parent molecular moiety through a carbonyl group, as defined herein. Representative examples of cycloalkylcarbonyl include, but are not limited to, cyclopropylcarbonyl, cyclopentylcarbonyl, cyclohexylcarbonyl, and cycloheptylcarbonyl.

The term "cycloalkylalkyl" as used herein means a cycloalkyl group, as defined herein, appended to the parent molecular moiety through an alkyl group, as defined herein. Representative examples of cycloalkylalkyl include, but are not limited to, cyclopropylmethyl, cyclopentylmethyl, cyclohexylmethyl, and cycloheptylmethyl. (C$_3$-C$_5$ cycloalkyl)alkyl in particular refers to a saturated cyclic hydrocarbon group containing from 3 to 5 carbons, for example, cyclopropyl, cyclobutyl, and cyclopentyl, appended to the parent molecular moiety through a alkyl group.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "fluoro" as used herein means —F.

The term "fluoroalkyl" as used herein means at least one fluoro group, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "fluoroalkoxy" as used herein means at least one fluoro group, appended to the parent molecular moiety through an alkoxy group, as defined herein. Representative examples of fluoroalkoxy include, but are not limited to, fluoromethoxy, difluoromethoxy, trifluoromethoxy, pentafluoroethoxy, and 2,2,2-trifluoroethoxy.

The term "formyl" as used herein means a —C(O)H group.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle", as used herein, refers to non-aromatic cyclic groups that contain at least one heteroatom. Non-aromatic heterocycles are non-aromatic cyclic groups that contain at least one heteroatom; examples of non-aromatic heterocyclic groups or non-aromatic heterocycles are further defined below. Heterocyclic rings are connected to the parent molecular moiety through a carbon atom, or alternatively in the case of heterocyclic rings that contain a bivalent nitrogen atom having a free site for attachment, the heterocyclic ring may be connected to the parent molecular moiety though a nitrogen atom. Additionally, the heterocycles may be present as tautomers.

The term "heteroaryl", as used herein, refers to an aromatic ring containing one or more heteroatoms independently selected from nitrogen, oxygen, and sulfur. Such rings can be monocyclic or bicyclic as further described herein. Heteroaryl rings are connected to the parent molecular moiety, or to L$^1$ or L$^2$, wherein L$^1$ and L$^2$ and L$^3$ are defined in formula (I) or (II), through a carbon or nitrogen atom.

The terms "monocyclic heteroaryl" or "5- or 6-membered heteroaryl ring", as used herein, refer to 5- or 6-membered aromatic rings containing at least one heteroatom independently selected from nitrogen, oxygen, and sulfur. The 5-membered ring contains two double bonds; such a ring may contain one, two, three or four nitrogen atoms, or may contain one or two nitrogen atoms and one oxygen atom, or may contain one or two nitrogen atoms and one sulfur atom, or may contain one oxygen atom, or may contain one sulfur atom. The 6-membered ring contains three double bonds, or alternatively, the 6-membered ring may contains 2 double bonds within the ring when the ring is substituted with an oxo group. Furthermore, the 6-membered ring may contain one, two, three or four nitrogen atoms, or may contain one or two nitrogen atoms and one oxygen atom, or may contain one or two nitrogen atoms and one sulfur atom, or may contain one or two nitrogen atoms and one sulfur atom, or may contain one or two nitrogen atoms and one oxygen atom. The 5- or 6-membered heteroaryl is connected to the parent molecular moiety through any carbon atom or any nitrogen atom contained within the monocyclic heteroaryl ring. Representative examples of 5- to 6-membered heteroaryl rings include, but are not limited to, furyl, imidazolyl, isoxazolyl, isothiazolyl, oxazolyl, pyrazinyl, pyrazolyl, pyridazinyl, pyridinyl, pyrimidinyl, pyrrolyl, tetrazolyl, thiadiazolyl, thiadiazolonyl, thiadiazinonyl, oxadiazolyl, oxadiazolonyl, oxadiazinonyl, thiazolyl, thienyl, triazinyl, triazolyl, pyridazinonyl, pyridonyl, and pyrimidinonyl.

The term "bicyclic heteroaryl" or "8- to 12-membered bicyclic heteroaryl ring", as used herein, refers to an 8-, 9-, 10-, 11-, or 12-membered bicyclic aromatic ring wherein one or more of the atoms of the ring has been replaced with at least one heteroatom selected from oxygen, sulfur, and nitrogen. The bicyclic heteroaryl of the invention maybe attached to the parent molecular moiety through any available carbon atom or nitrogen atom contained within the heteroaryl ring. Representative examples of bicyclic heteroaryl rings include indolyl, benzothienyl, benzofuranyl, indazolyl, benzimidazolyl, benzothiazolyl, benzoxazolyl, benzoisothiazolyl, benzoisoxazolyl, quinolinyl, isoquinolinyl, quinazolinyl, quinoxalinyl, phthalazinyl, pteridinyl, purinyl, naphthyridinyl, cinnolinyl, thieno[2,3-d]imidazole, 1,5-dihydro-benzo[b][1,4]diazepin-2-on-yl, and pyrrolopyrimidinyl.

Heteroaryl groups of the invention, whether monocyclic or bicyclic, are substituted with hydrogen, or optionally substituted with substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkylthio, alkynyl, amido, carboxy, cyano, cycloalkyl, fluoroalkoxy, formyl, haloalkoxy, haloalkyl, halogen, hydroxy, hydroxyalkyl, mercapto, nitro, oxo, —$NR^7R^8$, ($NR^7R^8$)carbonyl, —$SO_2N(R^9)(R^{10})$, and —$N(R^9)SO_2(R^{10})$. Monocyclic heteroaryl or 5- or 6-membered heteroaryl rings are substituted with 0, 1, 2, 3, 4, or 5 substituents. Bicyclic heteroaryl or 8- to 12-membered bicyclic heteroaryl rings are substituted with 0, 1, 2, 3, 4, 5, 6, 7, 8, or 9 substituents. Heteroaryl groups of the invention may be present as tautomers.

The term "heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3- or 4-membered ring contains 1 heteroatom selected from the group consisting of O, N and S. The 5-membered ring contains zero or one double bond and one, two or three heteroatoms selected from the group consisting of O, N and S. The 6- or 7-membered ring may contain zero, one, or two double bonds provided that the ring, when taken together with a substituent, does not tautomerize with a substituent to form an aromatic ring. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, a monocyclic heterocycle fused to a cycloalkyl, a monocyclic heterocycle fused to a cycloalkenyl, or a monocyclic heterocycle fused to a monocyclic heterocycle. The bicyclic heterocycle is connected to the parent molecular moiety through any carbon atom or any nitrogen atom contained within the monocyclic heterocycle. Representative examples of bicyclic heterocycle include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

The non-aromatic heterocycles of the invention substituted with hydrogen, or optionally substituted with 0, 1, 2, 3, 4, 5, 6, 7, 8, or 9 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, formyl, haloalkoxy, haloalkyl, halogen, hydroxy, hydroxyalkyl, mercapto, nitro, alkylthio, —$NR^7R^8$, ($NR^7R^8$)carbonyl, —$SO_2N(R^9)(R^{10})$, and —$N(R^9)SO_2(R^{10})$.

Additional examples of heterocycles include, but are not limited to, isoindoline-1,3-dione, (Z)-1H-benzo[e][1,4]diazepin-5(4H)-one, pyrimidine-2,4(1H,3H)-dione, benzo[d]thiazol-2(3H)-one, pyridin-4(1H)-one, imidazolidin-2-one, 1H-imidazol-2(3H)-one, pyridazin-3(2H)-one, tetrahydropyrimidin-2(1H)-one, and 1H-benzo[d]imidazol-2(3H)-one.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "mercapto" as used herein means a —SH group.

The term "($NR^7R^8$)" as used herein means both $R^7$ and $R^8$ group, as defined herein, appended to the parent molecular moiety through a nitrogen atom. $R^7$ and $R^8$ are each independently selected from the group consisting of hydrogen, $C_{1-4}$ alkyl, $C_3$-$C_4$ cycloalkyl, and aryl.

The term "($NR^7R^8$)alkyl" as used herein means an —$NR^7R^8$ group, as defined herein, appended to the parent molecular moiety through an alkyl group, as defined herein. Representative examples of ($NR^7R^8$)alkyl include, but are not limited to, 2-(methylamino)ethyl, 2-(dimethylamino)ethyl, 2-(amino)ethyl, 2-(ethylmethylamino)ethyl, and the like.

The term "($NR^7R^8$)carbonyl" as used herein means an —$NR^7R^8$ group, as defined herein, appended to the parent molecular moiety through a carbonyl group, as defined herein. Representative examples of ($NR^7R^8$)carbonyl include, but are not limited to, aminocarbonyl, (methylamino)carbonyl, (dimethylamino)carbonyl, (ethylmethylamino)carbonyl, and the like.

The term "($NR^7R^8$)sulfonyl" as used herein means a —$NR^7R^8$ group, as defined herein, appended to the parent molecular moiety through a sulfonyl group, as defined herein. Representative examples of ($NR^7R^8$)sulfonyl include, but are not limited to, aminosulfonyl, (methylamino)sulfonyl, (dimethylamino)sulfonyl and (ethylmethylamino)sulfonyl.

The term "—$N(R^9)SO_2(R^{10})$" as used herein means an amino group attached to the parent moiety to which is further appended with an $R^9$ group as defined herein, and a $SO_2$ group to which is appended an $(R^{10})$ group as defined herein. $R^9$ is selected from the group consisting of hydrogen, $C_{1-4}$ alkyl, $C_3$-$C_4$ cycloalkyl, and aryl, and $R^{10}$ is selected from the group consisting of $C_{1-4}$ alkyl, $C_3$-$C_4$ cycloalkyl, and aryl. Representative examples of —$N(R^9)SO_2(R^{10})$ include, but are not limited to, N-methylmethanesulfonamide.

The term "—$SO_2N(R^9)(R^{10})$" as used herein means a $N(R^9)(R^{10})$ group attached to a $SO_2$ group, appended to the parent moiety through the sulfonyl group. Representative examples of —$SO_2N(R^9)(R^{10})$ include, but are not limited to (dimethylamino)sulfonyl and N-cyclohexyl-N-methylsulfonyl.

The term "nitro" as used herein means a —$NO_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

The term "oxo" as used herein means (=O).

The term "sulfonyl" as used herein means a —$S(O)_2$— group.

As used herein, the term "antagonist" encompasses and describes compounds that prevent receptor activation by an $H_3$ receptor agonist, such as histamine, and also encompasses compounds known as "inverse agonists". Inverse agonists are compounds that not only prevent receptor activation by an $H_3$ receptor agonist, such as histamine, but also are able to inhibit intrinsic $H_3$ receptor activity.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3H$ (tritium), $^{14}C$, $^{11}C$, $^{15}O$, $^{18}F$, $^{35}S$, $^{123}I$, and $^{125}I$.

Compounds of the Invention

Compounds of the invention can have the formula (I) as described in the Summary of the Invention. In addition, certain embodiments of the invention further describe compounds of formula (I).

In compounds of formula (I), $L^1$ is a bond or alkylene. $L^1$ is preferably a bond. $L^2$ is a bond or alkylene. $L^2$ is preferably a bond.

$L^1$ and $L^2$ are both independently a bond or alkylene. Preferably $L^1$ and $L^2$ are a bond.

In addition, there is disclosed compounds of formula (I), wherein $R^{2a}$, $R^{2b}$, $R^{2c}$, $R^{2d}$, $R^{2e}$, and $R^{2f}$ all are hydrogen.

In another embodiment, there is disclosed compounds of formula (I), wherein at least two of $R^{3a}$, $R^{3b}$, $R^{3c}$, or $R^{3d}$ are a substituent other than hydrogen. Alternatively, there is also disclosed compounds of the invention wherein $R^{3a}$, $R^{3b}$, $R^{3c}$, and $R^{3d}$ are each hydrogen.

There are also disclosed compounds of formula (I), wherein $L^1$ is a bond; $L^2$ is a bond; $R^{3a}$, $R^{3b}$, $R^{3c}$, and $R^{3d}$ are each hydrogen; $Cy^1$ is phenyl, and $Cy^2$ is aryl, cycloalkyl, cycloalkenyl, heteroaryl or heterocycle, wherein the heteroaryl or heterocycle moiety has 1, 2, or 3 heteroatoms selected from nitrogen, oxygen, and sulfur, provided that at least one heteroatom is nitrogen. In a more preferred embodiment $Cy^2$ is pyridazinone. Preferably, compounds of formula (I), wherein $R^1$ is alkyl; $L^1$ is a bond; $L^2$ is a bond; $R^{2a}$, $R^{2b}$, $R^{2c}$, $R^{2d}$, $R^{2e}$, and $R^{2f}$ each is hydrogen; $R^{3a}$, $R^{3b}$, $R^{3c}$, and $R^{3d}$ are all hydrogen; $Cy^1$ is phenyl, and $Cy^2$ pyridazinone. More specifically, $R^1$ is more preferably a methyl.

There also exists an embodiment describing compounds of formula (I), wherein $L^1$ is a bond; $L^2$ is a bond; $R^{3a}$, $R^{3b}$, $R^{3c}$, and $R^{3d}$ are all hydrogen; $Cy^1$ is piperazine, and $Cy^2$ is aryl, cycloalkyl, cycloalkenyl, heteroaryl, or heterocycle, wherein the heteroaryl or heterocycle moiety has 1, 2, or 3 heteroatoms selected from nitrogen, oxygen, and sulfur, provided that at least one heteroatom is nitrogen. In a more preferred embodiment $Cy^2$ is pyridine optionally substituted with cyano.

There also exists a pharmaceutical composition comprising a compound of formula (I) and a pharmaceutically acceptable carrier.

Specific embodiments contemplated as part of the invention also include, but are not limited to:

(3aR,6aR)-4'-(5-ethyl-hexahydro-pyrrolo[3,4-b]pyrrol-1-yl)-biphenyl-4-carbonitrile;

4'-[(3aR,6aR)-5-isopropylhexahydropyrrolo[3,4-b]pyrrol-1(2H)-yl]-1,1'-biphenyl-4-carbonitrile;

4'-[(3aR,6aR)-5-propylhexahydropyrrolo[3,4-b]pyrrol-1(2H)-yl]-1,1'-biphenyl-4-carbonitrile;

4'-[(3aR,6aR)-5-butylhexahydropyrrolo[3,4-b]pyrrol-1(2H)-yl]-1,1'-biphenyl-4-carbonitrile;

4'-((3aR,6aR)-5-isobutyl-hexahydro-pyrrolo[3,4-b]pyrrol-1-yl)-biphenyl-4-carbonitrile;

4'-[(3aR,6aR)-5-(cyclopropylmethyl)hexahydropyrrolo[3,4-b]pyrrol-1(2H)-yl]-1,1'-biphenyl-4-carbonitrile;

4'-[(3aR,6aR)-5-methylhexahydropyrrolo[3,4-b]pyrrol-1(2H)-yl]-1,1'-biphenyl-4-carbonitrile;

(3aR,6aR)-1-(4'-methoxy-1,1'-biphenyl-4-yl)-5-methyloctahydropyrrolo[3,4-b]pyrrole;

{4'-[(3aR,6aR)-5-methylhexahydropyrrolo[3,4-b]pyrrol-1(2H)-yl]-1,1'-biphenyl-4-yl}acetonitrile;

1-{4'-[(3aR,6aR)-5-methylhexahydropyrrolo[3,4-b]pyrrol-1(2H)-yl]-1,1'-biphenyl-4-yl}ethanone;

3-{4-[(3aR,6aR)-5-methylhexahydropyrrolo[3,4-b]pyrrol-1(2H)-yl]phenyl}quinoline;

(3aR,6aR)-1-[4-(6-methoxypyridin-3-yl)phenyl]-5-methyloctahydropyrrolo[3,4-b]pyrrole;

{4'-[(3aR,6aR)-5-methylhexahydropyrrolo[3,4-b]pyrrol-1(2H)-yl]-1,1'-biphenyl-4-yl}methanol;

5-{4-[(3aR,6aR)-5-methylhexahydropyrrolo[3,4-b]pyrrol-1(2H)-yl]phenyl}pyridine-2-carbonitrile;

(3aR,6aR)-1-[4-(2,6-dimethylpyridin-3-yl)phenyl]-5-methyloctahydropyrrolo[3,4-b]pyrrole;

(3aR,6aR)-1-(3'-fluoro-4'-methoxy-1,1'-biphenyl-4-yl)-5-methyloctahydropyrrolo[3,4-b]pyrrole;

2-methyl-5-{4-[(3aR,6aR)-5-methylhexahydropyrrolo[3,4-b]pyrrol-1(2H)-yl]phenyl}-1,3-benzothiazole;

(3aR,6aR)-1-[4-(1H-imidazol-1-yl)phenyl]-5-methyloctahydropyrrolo[3,4-b]pyrrole;

(3aR,6aR)-1-(4'-ethoxy-1,1'-biphenyl-4-yl)-5-methyloctahydropyrrolo[3,4-b]pyrrole;

(3aR,6aR)-5-methyl-1-[4'-(methylthio)-1,1'-biphenyl-4-yl]
octahydropyrrolo[3,4-b]pyrrole;
(3aR,6aR)-5-methyl-1-(4-pyridin-4-ylphenyl)octahydropyr-
rolo[3,4-b]pyrrole;
4'-[(3aR,6aR)-5-methylhexahydropyrrolo[3,4-b]pyrrol-1
(2H)-yl]-1,1'-biphenyl-3-carbonitrile;
(3aR,6aR)-1-[4-(1,3-benzodioxol-5-yl)phenyl]-5-methyloc-
tahydropyrrolo[3,4-b]pyrrole;
(3aR,6aR)-5-methyl-1-(4-pyridin-3-ylphenyl)octahydropyr-
rolo[3,4-b]pyrrole;
(3aR,6aR)-1-[4-(2,6-difluoropyridin-3-yl)phenyl]-5-methy-
loctahydropyrrolo[3,4-b]pyrrole;
1-{4'-[(3aR,6aR)-5-methylhexahydropyrrolo[3,4-b]pyrrol-1
(2H)-yl]-1,1'-biphenyl-3-yl}ethanone;
(3aR,6aR)-1-[4'-(ethylthio)-1,1'-biphenyl-4-yl]-5-methyloc-
tahydropyrrolo[3,4-b]pyrrole;
(3aR,6aR)-5-methyl-1-[3'-(trifluoromethyl)-1,1'-biphenyl-
4-yl]octahydropyrrolo[3,4-b]pyrrole;
(3aR,6aR)-5-methyl-1-(4'-vinyl-1,1'-biphenyl-4-yl)octahy-
dropyrrolo[3,4-b]pyrrole;
(3aR,6aR)-5-methyl-1-[4'-methyl-3'-nitro-1,1'-biphenyl-4-
yl]octahydropyrrolo[3,4-b]pyrrole;
(3aR,6aR)-1-[4-(2,4-dimethoxypyrimidin-5-yl)phenyl]-5-
methyloctahydropyrrolo[3,4-b]pyrrole;
(3aR,6aR)-1-(4'-fluoro-1,1'-biphenyl-4-yl)-5-methyloctahy-
dropyrrolo[3,4-b]pyrrole;
(3aR,6aR)-5-methyl-1-[4-(1-naphthyl)phenyl]octahydropy-
rrolo[3,4-b]pyrrole;
{4'-[(3aR,6aR)-5-methylhexahydropyrrolo[3,4-b]pyrrol-1
(2H)-yl]-1,1'-biphenyl-3-yl}methanol;
(3aR,6aR)-1-(4-dibenzo[b,d]furan-4-ylphenyl)-5-methyloc-
tahydropyrrolo[3,4-b]pyrrole;
(3aR,6aR)-5-methyl-1-[3'-(trifluoromethyl)-1,1'-biphenyl-
4-yl]octahydropyrrolo[3,4-b]pyrrole;
(3aR,6aR)-1-(4'-fluoro-3'-methyl-1,1'-biphenyl-4-yl)-5-me-
thyloctahydropyrrolo[3,4-b]pyrrole;
(3aR,6aR)-5-methyl-1-[4-(2-naphthyl)phenyl]octahydropy-
rrolo[3,4-b]pyrrole;
(1E)-1-{4'-[(3aR,6aR)-5-methylhexahydropyrrolo[3,4-b]
pyrrol-1(2H)-yl]-1,1-biphenyl-4-yl}ethanone oxime;
1-{4'-[(3aR,6aR)-5-methylhexahydropyrrolo[3,4-b]pyrrol-1
(2H)-yl]-1,1-biphenyl-4-yl}ethanol;
2-{4'-[(3aR,6aR)-5-methylhexahydropyrrolo[3,4-b]pyrrol-1
(2H)-yl]-1,1'-biphenyl-4-yl}pyridazin-3(2H)-one, or
(3aR,6aR)-2-[4'-(5-methyl-hexahydro-pyrrolo[3,4-b]pyrrol-
1-yl)-biphenyl-4-yl]-2H-pyridazin-3-one;
(3aR,6aR)-5-methyl-1-(4'-pyrimidin-5-yl-1,1'-biphenyl-4-
yl)octahydropyrrolo[3,4-b]pyrrole;
4''-[(3aR,6aR)-5-methylhexahydropyrrolo[3,4-b]pyrrol-1
(2H)-yl]-1,1':4',1''-terphenyl-3-carbonitrile;
(3aR,6aR)-1-[4'-(6-fluoropyridin-3-yl)-1,1'-biphenyl-4-yl]-
5-methyloctahydropyrrolo[3,4-b]pyrrole;
(3aR,6aR)-1-[4'-(2,6-dimethylpyridin-3-yl)-1,1'-biphenyl-
4-yl]-5-methyloctahydropyrrolo[3,4-b]pyrrole;
(3aR,6aR)-1-[4'-(6-chloropyridin-3-yl)-1,1'-biphenyl-4-yl]-
5-methyloctahydropyrrolo[3,4-b]pyrrole;
4''-[(3aR,6aR)-5-methylhexahydropyrrolo[3,4-b]pyrrol-1
(2H)-yl]-1,1':4',1''-terphenyl-4-carbonitrile;
6-(4-{4-[(3aR,6aR)-5-methylhexahydropyrrolo[3,4-b]pyr-
rol-1(2H)-yl]phenyl}piperazin-1-yl)nicotinonitrile;
(3aR,6aR)-1-{4-[4-(6-chloropyridazin-3-yl)piperazin-1-yl]
phenyl}-5-methyloctahydropyrrolo[3,4-b]pyrrole;
(3aR,6aR)-5-methyl-1-{4-[4-(1,3-thiazol-2-yl)piperazin-1-
yl]phenyl}octahydropyrrolo[3,4-b]pyrrole;
(3aR,6aR)-5-methyl-1-[4-(4-pyridin-2-ylpiperazin-1-yl)
phenyl]octahydropyrrolo[3,4-b]pyrrole;
(3aR,6aR)-5-methyl-1-{4-[4-(4-nitrophenyl)piperazin-1-yl]
phenyl}octahydropyrrolo[3,4-b]pyrrole;
2-(4-{4-[(3aR,6aR)-5-methylhexahydropyrrolo[3,4-b]pyr-
rol-1(2H)-yl]phenyl}piperazin-1-yl)benzonitrile;
(3aR,6aR)-5-methyl-1-[4-(4-pyridin-4-ylpiperazin-1-yl)
phenyl]octahydropyrrolo[3,4-b]pyrrole;
(3aR,6aR)-5-methyl-1-{4-[4-(6-methylpyridazin-3-yl)pip-
erazin-1-yl]phenyl}octahydropyrrolo[3,4-b]pyrrole;
(3aR,6aR)-5-methyl-1-[4-(4-pyrazin-2-ylpiperazin-1-yl)
phenyl]octahydropyrrolo[3,4-b]pyrrole;
(3aR,6aR)-5-methyl-1-[4-(4-pyrimidin-2-ylpiperazin-1-yl)
phenyl]octahydropyrrolo[3,4-b]pyrrole;
4-(4-{4-[(3aR,6aR)-5-methylhexahydropyrrolo[3,4-b]pyr-
rol-1(2H)-yl]phenyl}piperazin-1-yl)benzonitrile;
(3aR,6aR)-1-{4-[4-(5-ethylpyrimidin-2-yl)piperazin-1-yl]
phenyl}-5-methyloctahydropyrrolo[3,4-b]pyrrole;
(3aR,6aR)-5-methyl-1-[4-(4-pyrimidin-5-ylpiperazin-1-yl)
phenyl]octahydropyrrolo[3,4-b]pyrrole;
(3aR,6aR)-2-{4-[4-(5-methyl-hexahydro-pyrrolo[3,4-b]pyr-
rol-1-yl)-phenyl]-piperazin-1-yl}-nicotinonitrile;
(3aR,6aR)-1-(4-benzylphenyl)-5-methyloctahydropyrrolo
[3,4-b]pyrrole;
(3aR,6aR)-5-methyl-1-(4-phenoxyphenyl)octahydropyrrolo
[3,4-b]pyrrole;
1-{4-[(3aR,6aR)-5-methylhexahydropyrrolo[3,4-b]pyrrol-1
(2H)-yl]phenyl}-2-phenylethanone;
(3aR,6aR)-1-[4-(4-bromophenoxy)phenyl]-5-methyloctahy-
dropyrrolo[3,4-b]pyrrole;
4'-{4-[(3aR,6aR)-5-methylhexahydropyrrolo[3,4-b]pyrrol-1
(2H)-yl]phenoxy}-1,1'-biphenyl-4-carbonitrile;
{4-[(3aR,6aR)-5-methylhexahydropyrrolo[3,4-b]pyrrol-1
(2H)-yl]phenyl}(phenyl)methanone;
4-[(3aR,6aR)-5-methylhexahydropyrrolo[3,4-b]pyrrol-1
(2H)-yl]benzonitrile;
1-{4-[(3aR,6aR)-5-methylhexahydropyrrolo[3,4-b]pyrrol-1
(2H)-yl]phenyl}methanamine;
3-({4-[(3aR,6aR)-5-methylhexahydropyrrolo[3,4-b]pyrrol-
1(2H)-yl]benzyl}amino)benzonitrile;
5-ethyl-N-{4-[(3aR,6aR)-5-methylhexahydropyrrolo[3,4-b]
pyrrol-1(2H)-yl]benzyl}pyrimidin-2-amine;
2-(5-{4-[(3aR,6aR)-5-methylhexahydropyrrolo[3,4-b]pyr-
rol-1(2H)-yl]phenyl}pyridin-2-yl)pyridazin-3(2H)-one;
2-(6-{4-[(3aR,6aR)-5-methylhexahydropyrrolo[3,4-b]pyr-
rol-1(2H)-yl]phenyl}pyridin-3-yl)pyridazin-3(2H)-one;
2-(5-{4-[(3aR,6aR)-5-methylhexahydropyrrolo[3,4-b]pyr-
rol-1(2H)-yl]phenyl}-1,3-thiazol-2-yl)pyridazin-3(2H)-
one;
5-(4-{4-[(3aR,6aR)-5-methylhexahydropyrrolo[3,4-b]pyr-
rol-1(2H)-yl]phenyl}piperazin-1-yl)pyridine-2-carboni-
trile;
(3aR,6aR)-1-[4'-(2-methoxypyrimidin-5-yl)-1,1'-biphenyl-
4-yl]-5-methyloctahydropyrrolo[3,4-b]pyrrole;
5-{4'-[(3aR,6aR)-5-methylhexahydropyrrolo[3,4-b]pyrrol-1
(2H)-yl]-1,1'-biphenyl-4-yl}pyridine-2-carbonitrile;
6-methyl-2-{4'-[(3aR,6aR)-5-methylhexahydropyrrolo[3,4-
b]pyrrol-1(2H)-yl]-1,1'-biphenyl-4-yl}pyridazin-3(2H)-
one;
(3aR,6aR)-5-methyl-1-[4'-(1-methyl-1H-pyrazol-4-yl)-1,1'-
biphenyl-4-yl]octahydropyrrolo[3,4-b]pyrrole;
(3aR,6aR)-1-[4'-(3,5-dimethyl-1H-pyrazol-4-yl)-1,1'-biphe-
nyl-4-yl]-5-methyloctahydropyrrolo[3,4-b]pyrrole;
(3aR,6aR)-5-methyl-1-[4'-(1-trityl-1H-pyrazol-4-yl)-1,1'-
biphenyl-4-yl]octahydropyrrolo[3,4-b]pyrrole;
(3aR,6aR)-5-methyl-1-[4'-(1H-pyrazol-4-yl)-1,1'-biphenyl-
4-yl]octahydropyrrolo[3,4-b]pyrrole;

3-methyl-1-{4'-[(3aR,6aR)-5-methylhexahydropyrrolo[3,4-b]pyrrol-1(2H)-yl]-1,1'-biphenyl-4-yl}pyridin-2(1H)-one;

5-methyl-1-{4'-[(3aR,6aR)-5-methylhexahydropyrrolo[3,4-b]pyrrol-1(2H)-yl]-1,1'-biphenyl-4-yl}pyridin-2(1H)-one;

6-methyl-1-{4'-[(3aR,6aR)-5-methylhexahydropyrrolo[3,4-b]pyrrol-1(2H)-yl]-1,1'-biphenyl-4-yl}pyridin-2(1H)-one;

2-{4'-[(3aR,6aR)-5-ethylhexahydropyrrolo[3,4-b]pyrrol-1(2H)-yl]-1,1'-biphenyl-4-yl}pyridazin-3(2H)-one;

2-{4'-[(3aR,6aR)-5-cyclobutylhexahydropyrrolo[3,4-b]pyrrol-1(2H)-yl]-1,1'-biphenyl-4-yl}pyridazin-3(2H)-one; and 2-{4'-[(3aR,6aR)-5-methylhexahydropyrrolo[3,4-b]pyrrol-1(2H)-yl]biphenyl-4-yl}-4,5-dihydropyridazin-3(2H)-one.

In addition, there are disclosed compounds of formula (II), wherein when $L^1$ is a bond, Z is $-L^3-Cy^3$. Furthermore, there are described compounds of formula (II), wherein when $L^1$ is a bond, and $Cy^1$ is phenyl, and Z is $-L^3-Cy^3$ and $L^3$ is a bond, and $Cy^3$ is not a cyclic amine of formula

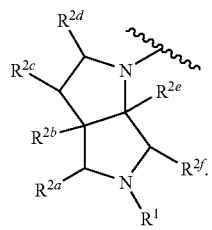

Compounds of the invention were named by ACD/ChemSketch version 5.01 (developed by Advanced Chemistry Development, Inc., Toronto, ON, Canada), or ChemDraw Ultra 9.0 (CambridgeSoft), or were given names consistent with ACD nomenclature. The practice of assigning names to chemical compounds from structures, and of assigning chemical structures from given chemical names is well known to those of ordinary skill in the art.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes and cyclohexanes may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen, deuterium and tritium, or $^{12}C$, $^{11}C$ and $^{13}C$, or $^{19}F$ and $^{18}F$.

Methods of the Invention

Compounds and compositions of the invention are useful for modulating the effects of histamine-3, particularly by histamine-3 antagonism, agonism, or inverse agonism. In particular, the compounds and compositions of the invention can be used for treating and preventing disorders modulated by histamine-3. Typically, such disorders can be ameliorated by modulating the histamine-3 receptors in a mammal, preferably by administering a compound or composition of the invention, either alone or in combination with another active agent, for example, as part of a therapeutic regimen.

Certain substituted octahydro-pyrrolo[3,4-b]pyrrole derivatives, including but not limited to those specified as compounds of the invention, demonstrate the ability to affect histamine-3 activity, and particularly for histamine-3 antagonism. Such compounds can be useful for the treatment and prevention of a number of histamine-3-mediated diseases or conditions. Substituted octahydro-pyrrolo[3,4-b]pyrrole compounds contemplated to demonstrate such activity have the formula:

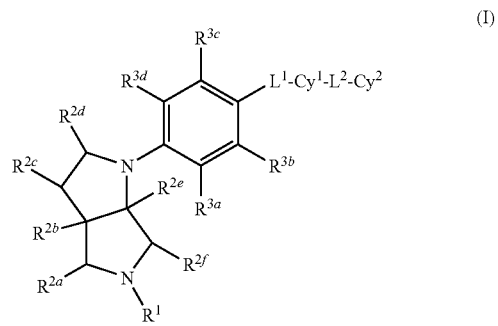

(I)

wherein $R^1$, $R^{2a}$, $R^{2b}$, $R^{2c}$, $R^{2d}$, $R^{2e}$, $R^{2f}$, $R^{3a}$, $R^{3b}$, $R^{3c}$, $R^{3d}$, $L^1$, $L^2$, $Cy^1$, and $Cy^2$ are as previously described herein.

There is also disclosed a method of treating a mammal having a condition where modulation of histamine-3 receptor activity is of therapeutic benefit, said method comprising administering to a subject having or susceptible to said disorder with a therapeutically effective amount of a compound of the formula (II),

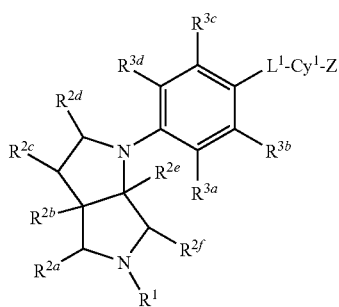

(II)

or a pharmaceutically acceptable salt, ester, amide, or prodrug thereof, wherein, $R^1$ is alkyl, $C_3$-$C_5$ cycloalkyl, or ($C_3$-$C_5$ cycloalkyl)methyl; $R^{2a}$, $R^{2b}$, $R^{2c}$, $R^{2d}$, $R^{2e}$, and $R^{2f}$ each are independently hydrogen, methyl, or fluoromethyl; $R^{3a}$, $R^{3b}$, $R^{3c}$, and $R^{3d}$ each are independently hydrogen, alkyl, fluoroalkyl, fluoroalkoxy, alkoxy, thioalkoxy, halogen, or nitrile, with the proviso that when one or more of $R^{3a}$, $R^{3b}$, $R^{3c}$, and $R^{3d}$ are alkyl, then at least one of $R^{3a}$, $R^{3b}$, $R^{3c}$, and $R^{3d}$ is fluoroalkyl, fluoroalkoxy, alkoxy, thioalkoxy, halogen, or nitrile; $L^1$ is a bond, oxygen, sulfur, carbonyl, alkylene, alkylcarbonyl, alkylamino, —C(=N—Oalkyl)-, $NR^4$, —C(=O)$NR^4$—, or —$NR^4$C(=O)—; $R^4$ is hydrogen or alkyl; $Cy^1$ is aryl, cycloalkyl, cycloalkenyl, heteroaryl, or heterocycle; Z is a substituent $R^6$ or a group represented by -$L^3$-$Cy^3$; $R^6$ is hydrogen, acyl, acyloxy, alkenyl, alkoxy, alkoxyalkoxy, alkoxyalkyl, alkoxycarbonyl, alkoxyimino, alkoxysulfonyl, alkyl, alkylcarbonyl, alkylsulfonyl, alkynyl, amido, carboxy, cyano, cycloalkyl, fluoroalkoxy, haloalkoxy, haloalkyl, halogen, hydroxy, hydroxyalkyl, mercapto, nitro, alkylthio, amino, $NHR^7$, $NR^7R^8$, —N($R^7$)C(=O)$R^9$, —C(=O)$NR^7R^8$, or N($R^7$)$SO_2$($R^{10}$); $L^3$ is a bond, oxygen, sulfur, carbonyl, alkylene, alkylamino, alkylamino, —C(=N—Oalkyl)-, $NR^{11}$, —C(=O)$NR^{11}$—, or —$NR^{11}$C (=O)—; $Cy^3$ is aryl, cycloalkyl, cycloalkenyl, heteroaryl, or heterocycle; and $R^7$, $R^8$, $R^9$, $R^{10}$, and $R^{11}$ at each occurrence are independently hydrogen, $C_{1-4}$ alkyl, $C_3$-$C_4$ cycloalkyl, or a ($C_3$-$C_4$ cycloalkyl)amine; provided that $Cy^3$ is not

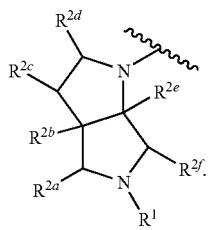

There is also disclosed a method of treating a mammal having a condition where modulation of histamine-3 receptor activity is of therapeutic benefit, said method comprising administering to a subject having or susceptible to said disorder with a therapeutically effective amount of a compound of the formula (II), wherein $Cy^2$ is aryl, cycloalkyl, cycloalkenyl, heteroaryl or heterocycle, each having 1, 2, or 3 heteroatoms selected from nitrogen, oxygen, and sulfur, provided that at least one heteroatom is nitrogen; provided that when $L^1$ is a bond, Z is -$L^3$-$Cy^3$ and further provided that when $L^1$ is a bond, and $Cy^1$ is phenyl, and Z is -$L^3$-$Cy^3$ and $L^3$ is a bond, $Cy^3$ is not a cyclic amine of formula

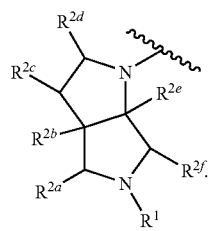

The method of treating a mammal having a condition where modulation of histamine-3 receptor activity is of therapeutic benefit from the administration of a compounds of formula (II), wherein the condition or disorder is selected from the group consisting of Alzheimer's disease, asthma, attention-deficit hyperactivity disorder, bipolar disorder, cognitive dysfunction, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, metabolic syndrome, mild cognitive impairment, migraine, mood and attention alteration, motion sickness, narcolepsy, neurogenic inflammation, obesity, obsessive compulsive disorder, pain, Parkinson's disease, polycystic ovary syndrome, schizophrenia, cognitive deficits of schizophrenia, seizures, septic shock, Syndrome X, Tourette's syndrome, vertigo, and sleep disorders.

In particular, the method of treating a mammal having attention-deficit hyperactivity disorder, Alzheimer's disease, or dementia where modulation of histamine-3 receptor activity is of therapeutic benefit from the administration of a compounds of formula (II).

In particular, the method of treating a mammal having schizophrenia or cognitive deficits of schizophrenia, where modulation of histamine-3 receptor activity is of therapeutic benefit from the administration of a compounds of formula (II).

In particular, the method of treating a mammal having narcolepsy, sleep disorders, asthma, or obesity, where modulation of histamine-3 receptor activity is of therapeutic benefit from the administration of a compounds of formula (II).

As an important consequence of the ability of the compounds of the invention to modulate the effects of histamine-3 receptors in cells, the compounds described for the method of the invention can affect physiological processes in humans and animals. In this way, the compounds and compositions of formulas (I) or (II), are useful for treating and preventing diseases and disorders modulated by histamine-3 receptors. Typically, treatment or prevention of such diseases and disorders can be effected by selectively modulating the histamine-3 receptors in a mammal, by administering a compound or composition of the invention, either alone or in combination with another active agent as part of a therapeutic regimen.

Particularly preferred are compounds of formula (I) or (II) as described in the Detailed Description above. More preferred are the compounds of formula (I).

Compounds of formulas (I) or (II), can be administered to a subject having such a disorder or susceptible to such disorders in a therapeutically effective amount. The compounds are particularly useful for a method of treating a mammal having a condition where modulation of histamine-3 receptor activity is of therapeutic benefit, wherein the method is accomplished by administering a therapeutically effective amount of a compound of formula (I) or (II) to a subject having, or susceptible to, such a disorder.

Compounds useful for the method of the invention, include but are not limited to those specified in the examples, and possess an affinity for the histamine-3 receptors. Such compounds therefore may be useful for the treatment and prevention of diseases or conditions related to histamine-3 modulation. Examples of such diseases or conditions are, for example, attention-deficit hyperactivity disorder (ADHD), deficits in attention, dementia, and diseases with deficits of memory, learning, schizophrenia, cognitive deficits of schizophrenia, cognitive deficits and dysfunction in psychiatric disorders, Alzheimer's disease, mild cognitive impairment, epilepsy, seizures, allergic rhinitis, and asthma, motion sickness, dizziness, Meniere's disease, vestibular disorders, vertigo, obesity, diabetes, type II diabetes, Syndrome X, insulin resistance syndrome, metabolic syndrome, pain, including neuropathic pain, neuropathy, sleep disorders, narcolepsy, pathological sleepiness, jet lag, drug abuse, mood alteration, bipolar disorder, depression, obsessive compulsive disorder, Tourette's syndrome, Parkinson's disease, and medullary thyroid carcinoma, melanoma, and polycystic ovary syndrome. The ability of histamine-3 receptor modulators, and consequently the compounds of the invention, to prevent or treat such disorders is demonstrated by examples found in the following references.

The ability of the compounds of the invention, including, but not limited to, those specified in the examples, to treat attention-deficit hyperactivity disorder (ADHD), and deficits in attention, may be demonstrated by Cowart, et al. *J. Med. Chem.* 2005, 48, 38-55; Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190; "Effects of histamine $H_3$ receptor ligands GT-2331 and ciproxifan in a repeated acquisition avoidance response in the spontaneously hypertensive rat pup." Fox, G. B., et al. Behavioural Brain Research (2002), 131(1,2), 151-161; Yates, et al. JPET (1999) 289, 1151-1159 "Identification and Pharmacological Characterization of a Series of New 1H-4-Substituted-Imidazoyl Histamine $H_3$ Receptor Ligands"; Ligneau, et al. Journal of Pharmacology and Experimental Therapeutics (1998), 287, 658-666; Tozer, M. Expert Opinion Therapeutic Patents (2000) 10, p. 1045; M. T. Halpern, "GT-2331" Current Opinion in Central and Peripheral Nervous System Investigational Drugs (1999) 1, pages 524-527; Shaywitz et al., Psychopharmacology, 82:73-77 (1984); Dumery and Blozovski, Exp. Brain Res., 67:61-69 (1987); Tedford et al., J. Pharmacol. Exp. Ther., 275:598-604 (1995); Tedford et al., Soc. Neurosci. Abstr., 22:22 (1996); and Fox, et al., Behav. Brain Res., 131:151-161 (2002); Glase, S. A., et al. "Attention deficit hyperactivity disorder: pathophysiology and design of new treatments." Annual Reports in Medicinal Chemistry (2002), 37 11-20; Schweitzer, J. B., and Holcomb, H. H. "Drugs under investigation for attention-deficit hyperactivity disorder" Current Opinion in Investigative Drugs (2002) 3, p. 1207.

The ability of the compounds of the invention, including, but not limited to, those specified in the examples, to treat dementia, and diseases with deficits of memory and learning, may be demonstrated by "Two novel and selective nonimidazole $H_3$ receptor antagonists A-304121 and A-317920: II. In vivo behavioral and neurophysiological characterization." Fox, G. B., et al. Journal of pharmacology and experimental therapeutics (2003 June), 305(3), 897-908; "Identification of novel $H_3$ receptor ($H_3R$) antagonist with cognition enhancing properties in rats." Fox, G. B.; Inflammation Research (2003), 52(Suppl. 1), S31-S32; Bernaerts, P., et al. "Histamine $H_3$ antagonist thioperamide dose-dependently enhances memory consolidation and reverses amnesia induced by dizocilpine or scopolamine in a one-trial inhibitory avoidance task in mice" Behavioural Brain Research 154 (2004) 211-219; Onodera, et al. Nauyn-Schmiedebergs' Arch. Pharmacol. (1998), 357, 508-513; Prast, et al. Brain Research (1996) 734, 316-318; Chen, et al. Brain Research (1999) 839, 186-189 "Effects of histamine on MK-801-induced memory deficits in radial maze performance in rats"; Passani, et al. "Central histaminergic system and cognition" Neuroscience and Biobehavioral Reviews (2000) 24, p 107-113.

The ability of the compounds of the invention, including, but not limited to, those specified in the examples, to treat schizophrenia, cognitive deficits of schizophrenia, and cognitive deficits, may be demonstrated by Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190 and by "Enhancement of prepulse inhibition of startle in mice by the $H_3$ receptor antagonists thioperamide and ciproxifan." Browman, Kaitlin E., et al. Behavioural Brain Research (2004), 153(1), 69-76; "$H_3$ receptor blockade by thioperamide enhances cognition in rats without inducing locomotor sensitization."; Komater, V. A., et al. Psychopharmacology (Berlin, Germany) (2003), 167(4), 363-372; A A Rodrigues, F P Jansen, R Leurs, H Timmerman and G D Prell "Interaction of clozapine with the histamine $H_3$ receptor in rat brain" British Journal of Pharmacology (1995), 114(8), pp. 1523-1524; Passani, et al. "Central histaminergic system and cognition" Neuroscience and Biobehavioral Reviews (2000) 24, p 107-113; Morriset, S., et al. "Atypical Neuroleptics Enhance Histamine Turnover in Brain Via 5-Hydroxytryptamine$_{2A}$ Receptor Blockade" Journal of Pharmacology and Experimental Therapeutics (1999) 288, pages 590-596.

The ability of the compounds of the invention, including, but not limited to, those specified in the examples, to treat dysfunction in psychiatric disorders, Alzheimer's disease, and mild cognitive impairment may be demonstrated by Meguro, et al. Pharmacology, Biochemistry and Behavior (1995) 50(3), 321-325; Esbenshade, T., et al. "Pharmacological and behavioral properties of A-349821, a selective and potent human histamine $H_3$ receptor antagonist" Biochemical Pharmacology 68 (2004) 933-945; Huang, Y.-W., et al. "Effect of the histamine H3-antagonist clobenpropit on spatial memory deficits induced by MK-801 as evaluated by radial maze in Sprague-Dawley rats" Behavioural Brain Research 151 (2004) 287-293; Mazurkiewicz-Kwilecki and Nsonwah, Can. J. Physiol. Pharmacol. (1989) 67, p. 75-78; P. Panula, et al., Neuroscience (1997) 82, 993-997; Haas, et al., Behav. Brain Res. (1995) 66, p. 41-44; De Almeida and Izquierdo, Arch. Int. Pharmacodyn. (1986), 283, p. 193-198; Kamei et al., Psychopharmacology, (1990) 102, p. 312-318; Kamei and Sakata, Jpn. J. Pharmacol. (1991), 57, p. 437-482; Schwartz et al., Psychopharmacology, The Fourth Generation of Progress. Bloom and Kupfer (eds). Raven Press, New York, (1995) 397; and Wada, et al., Trends in Neurosci. (1991) 14, p. 415.

The ability of the compounds of the invention, including, but not limited to, those specified in the examples, to treat epilepsy, and seizures, may be demonstrated by Harada, C., et al. "Inhibitory effect of iodophenpropit, a selective histamine $H_3$ antagonist, on amygdaloid kindled seizures" Brain Research Bulletin (2004) 63 p, 143-146; as well as by Yokoyama, et al., Eur. J. Pharmacol. (1993) 234, p. 129-133; Yokoyama, et al. European Journal of Pharmacology (1994)

260, p. 23; Yokoyama and Iinuma, CNS Drugs (1996) 5, p. 321; Vohora, Life Sciences (2000) 66, p. 297-301; Onodera et al., Prog. Neurobiol. (1994) 42, p. 685; Chen, Z., et al. "Pharmacological effects of carcinine on histaminergic neurons in the brain" British Journal of Pharmacology (2004) 143, 573-580; R. Leurs, R. C. Volling a and H. Timmerman, "The medicinal chemistry and therapeutic potential of ligands of the histamine $H_3$ receptor", Progress in Drug Research (1995) 45, p. 170-165; Leurs and Timmerman, Prog. Drug Res. (1992) 39, p. 127; H. Yokoyama and K. Iinuma, "Histamine and Seizures: Implications for the treatment of epilepsy", CNS Drugs, 5(5): 321-330 (1995); and K. Hurukami, H. Yokoyama, K. Onodera, K. Iinuma and T. Watanabe, "AQ-0145, A newly developed histamine $H_3$ antagonist, decreased seizure susceptibility of electrically induced convulsions in mice", Meth. Find. Exp. Clin. Pharmacol., 17(C):70-73 (1995); Yawata, et al. "Role of histaminergic neurons in development of epileptic seizures in EL mice" Molecular Brain Research 132 (2004) 13-17.

The ability of the compounds of the invention, including, but not limited to, those specified in the examples, to treat allergic rhinitis, and asthma, may be demonstrated by McLeod, R. L., Mingo, G. G., Herczku, C., DeGennaro-Culver, F., Kreutner, W., Egan, R. W., Hey, J. A., "Combined histamine $H_1$ and $H_3$ receptor blockade produces nasal decongestion in an experimental model of nasal congestion" Am. J. Rhinol. (1999a) 13, p. 391-399; McLeod, Robbie L.; Egan, Robert W.; Cuss, Francis M.; Bolser, Donald C.; Hey, John A. (Allergy, Schering-Plough Research Institute, Kenilworth, N.J., USA.) Progress in Respiratory Research (2001), 31 (in *New Drugs for Asthma, Allergy and COPD*), pp. 133-136; A. Delaunois A., et al., "Modulation of acetylcholine, capsaicin and substance P effects by histamine $H_3$ receptors in isolated perfused rabbit lungs," European Journal of Pharmacology (1995) 277, p. 243-250; Dimitriadou, et al., "Functional relationship between mast cells and C-sensitive nerve fibres evidenced by histamine $H_3$-receptor modulation in rat lung and spleen," Clinical Science (1994), 87, p. 151-163.

The ability of the compounds of the invention, including, but not limited to, those specified in the examples, to treat motion sickness, dizziness, Meniere's disease, vestibular disorders, and vertigo, may be demonstrated by Pan, et al. Methods and Findings in Clinical Pharmacology (1998), 20(9), 771-777; O'Neill, et al. Methods and Findings in Clinical Pharmacology (1999) 21(4), 285-289; Chavez, et al. "Histamine (H3) receptors modulate the excitatory amino acid receptor response of the vestibular afferents" Brain Research (2005), v. 1064, p. 1-9, and by R. Leurs, R. C. Volling a and H. Timmerman, "The medicinal chemistry and therapeutic potential of ligands of the histamine $H_3$ receptor," Progress in Drug Research (1995), 45, p. 170-165, Lozada, et al. "Plasticity of histamine $H_3$ receptor expression and binding in the vestibular nuclei after labyrinthectomy in rat" BioMedCentral Neuroscience 2004, 5:32.

The ability of the compounds of the invention, including, but not limited to, those specified in the examples, to treat obesity, diabetes, type II diabetes, Syndrome X, insulin resistance syndrome, and metabolic syndrome, may be demonstrated by Hancock, A. A. "Antiobesity effects of A-331440, a novel non-imidazole histamine $H_3$ receptor antagonist" European Journal of Pharmacology (2004) 487, 183-197; Hancock, A. A., et al. "Histamine $H_3$ antagonists in models of obesity" Inflamm. res. (2004) 53, Supplement 1 S47-S48; as well as by E. Itoh, M. Fujimiay, and A. Inui, "Thioperamide, A histamine $H_3$ receptor antagonist, powerfully suppresses peptide YY-induced food intake in rats," Biol. Psych. (1999) 45(4), p. 475-481; S. I. Yates, et al., "Effects of a novel histamine $H_3$ receptor antagonist, GT-2394, on food intake and weight gain in Sprague-Dawley rats," Abstracts, Society for Neuroscience, 102.10:219 (November, 2000); Malmlof, et al. "Influence of a selective histamine $H_3$ receptor antagonist on hypothalamic neural activity, food intake and body weight" International Journal of Obesity (2005) 29, 1402-1412; and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, #P39 (November, 2000); Sakata T; et al. "Hypothalamic neuronal histamine modulates ad libitum feeding by rats." Brain research (1990 Dec. 24), 537(1-2), 303-6.

The ability of the compounds of the invention, including, but not limited to, those specified in the examples, to treat pain, including neuropathic pain and neuropathy, may be demonstrated by Malmberg-Aiello, Petra; Lamberti, Claudia; Ghelardini, Carla; Giotti, Alberto; Bartolini, Alessandro. British Journal of Pharmacology (1994), 111(4), 1269-1279; Hriscu, Anisoara; Gherase, Florenta; Pavelescu, M.; Hriscu, E. "Experimental evaluation of the analgesic efficacy of some antihistamines as proof of the histaminergic receptor involvement in pain." Farmacia, (2001), 49(2), 23-30, 76.

The ability of the compounds of the invention, including, but not limited to, those specified in the examples, to treat sleep disorders, including narcolepsy and pathological sleepiness, and jet lag, may be demonstrated by Barbier, A. J., et al. "Acute wake-promoting actions of JNJ-5207852, a novel, diamine-based $H_3$ antagonist" British Journal of Pharmacology (2004) 1-13; Monti et al., Neuropsychopharmacology (1996) 15, 31-35; Lin et al., Brain Res. (1990) 523, p. 325-330; Monti, et al., Neuropsychopharmacology (1996) 15, p. 31-35; Ligneau, et al. Journal of Pharmacology and Experimental Therapeutics (1998), 287, 658-666; Sakai, et al., Life Sci. (1991) 48, p. 2397-2404; Mazurkiewicz-Kwilecki and Nsonwah, Can. J. Physiol. Pharmacol., (1989) 67, p. 75-78; P. Panula, et al., Neuroscience (1998) 44, 465-481; Wada, et al., Trends in Neuroscience (1991) 14, p. 415; and Monti, et al., Eur. J. Pharmacol. (1991), 205, p. 283; Dvorak, C., et al. "4-Phenoxypiperidines: Potent, Conformationally Restricted, Non-Imidazole Histamine $H_3$ Antagonists" Journal of Medicinal Chemistry (2005) 48, 2229-2238.

The ability of the compounds of the invention, including, but not limited to, those specified in the examples, to treat drug abuse. Amphetamine is an abused stimulant in humans. It, and similar abused drugs stimulate locomotor activity in animals, and it has been found that the $H_3$ antagonist thioperamide suppresses the locomotor stimulation induced by amphetamine; therefore $H_3$ antagonists are likely to be useful for treating drug abuse as may be demonstrated by Clapham J.; Kilpatrick G. J. "Thioperamide, the selective histamine $H_3$ receptor antagonist, attenuates stimulant-induced locomotor activity in the mouse", European journal of pharmacology (1994), 259(2), 107-14.

The ability of the compounds of the invention, including, but not limited to, those specified in the examples, to treat mood alteration, bipolar disorder, depression, obsessive compulsive disorder, and Tourette's syndrome, may be demonstrated by Lamberti, et al. British Journal of Pharmacology (1998) 123, 1331-1336; Perez-Garcia C, et. al., Psychopharmacology (Berlin) (1999) 142(2): 215-20.

The ability of the compounds of the invention, including, but not limited to, those specified in the examples, to treat Parkinson's disease (a disease wherein patients have deficits in ability to initiate movements, and patients' brain have low dopamine levels) may be demonstrated by Sánchez-Lemus, E., et al. "Histamine $H_3$ receptor activation inhibits dopamine $D_1$ receptor-induced cAMP accumulation in rat striatal slices" Neuroscience Letters (2004) 364, p. 179-184; Sakai, et al., Life Sci. (1991) 48, 2397-2404; Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist" Journal of Pharmacology and Experimental Therapeutics, 313:176-190, 2005; Chen, Z., et al. "Pharmacological effects of carcinine on histaminergic neurons in the brain" British Journal of Pharmacology (2004) 143, 573-580.

The ability of the compounds of the invention, including, but not limited to, those specified in the examples, to treat medullary thyroid carcinoma, melanoma, polycystic ovary syndrome, may be demonstrated by Polish Med. Sci. Mon. (1998) 4(5): 747; Adam Szelag, "Role of histamine $H_3$-receptors in the proliferation of neoplastic cells in vitro," Med. Sci. Monitor (1998) 4(5): 747-755; and C. H. Fitzsimons, et al., "Histamine receptors signalling in epidermal tumor cell lines with H-ras gene alterations," Inflammation Res. (1998) 47 (Suppl 1):S50-S51.

Compounds of the invention are particularly useful for treating and preventing a condition or disorder affecting attention-deficit hyperactivity, Alzheimer's disease, or dementia. Compounds of the invention are particularly useful for treating and preventing a condition or disorder affecting schizophrenia or cognitive deficits of schizophrenia. Compounds of the invention are particularly useful for treating and preventing a condition or disorder affecting narcolepsy, sleep disorders, allergic rhinitis, asthma, or obesity.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 30 mg/kg of body weight. For purposes of oral administration, more preferable doses can be in the range of from about 0.001 to about 0.1 mg/kg body weight. If desired, the effective daily dose can be divided into multiple doses for purposes of administration; consequently, single dose compositions may contain such amounts or submultiples thereof to make up the daily dose.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: Xantphos for 4,5-bis(diphenylphosphino)-9,9-dimethylxanthene, [161265-03-8]; BINAP for 2,2'-bis(diphenylphosphino)-1,1'-binaphthyl; Boc for butyloxycarbonyl; EtOAc for ethyl acetate; HPLC for high pressure liquid chromatography; IPA for isopropyl alcohol; Me for methyl; MeOH for methanol; Ms for methanesulfonyl; Pd for palladium; tBu for tert-butyl; TEA for triethylamine; TFA for trifluoroacetic acid; THF for tetrahydrofuran; and Ts for para-toluenesulfonyl; dba for dibenzylidine acetone, rt for "room temperature" or ambient temperature suitably ranging 17-30° C. Copper iodide is CuI; palladium acetate is $Pd(OAc)_2$. Emrys™ Process Vial is a microwave process vial (10 ml or 30 ml glass vial with sealed cap). All microwave irradiation experiments were carried out using the Emrys Synthesizer from PersonalChemistry AB (Uppsala). All experiments were carried out in sealed microwave process vials utilizing the standard absorbance level (300 W maximum power). If not stated otherwise, reaction times under microwave conditions reflect total irradiation times counted from the beginning of the irradiation. As identifiers of compounds available from descriptions reported in the literature or available commercially, CAS numbers may be used; CAS numbers are identifier numbers assigned to compounds by Chemical Abstracts Service of the American Chemical Society, and are well known to those of ordinary skill in the art.

The compounds of this invention can be prepared by a variety of synthetic procedures. Representative procedures are shown in, but are not limited to, Schemes 1-17.

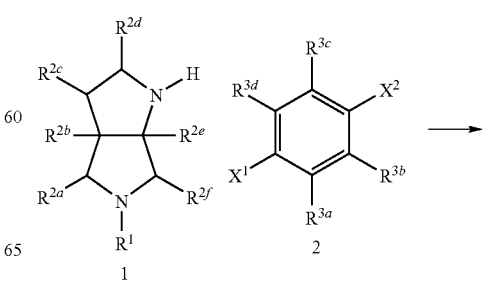

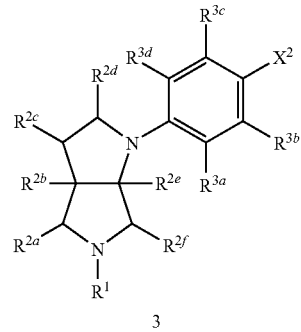

3

Compounds represented by formula 3, which are representative of compounds of the invention may be obtained as describe in Scheme 1. Compounds of formula 1, wherein $R^1$ is an alkyl, cycloalkyl or a cycloalkyl alkyl group as defined in formula (I) and $R^{2a}$, $R^{2b}$, $R^{2c}$, $R^{2d}$, and $R^{2e}$, are as defin d in formula (I), when treated with compounds of formula 2, wherein $R^{3a}$, $R^{3b}$, $R^{3c}$, and $R^{3d}$, are as defined in formula (I), $X^1$ is bromide, iodide, chloride or $F_3CCO_2$—and wherein $X^2$ is -$L^1$-$Cy^1$-$L^2$-$Cy^2$, -$L^3$-$Cy^3$ or $R^6$, along with a palladium catalyst such as but not limited to palladium acetate (Pd(OAc)$_2$) or tris(dibenzylideneacetone)dipalladium (Pd$_2$dba$_3$), a ligand additive such racemic-2,2'-bis(diphenylphosphino)-1,1'-binaphthyl (BINAP) and a base such as sodium tert-butoxide in a solvent such as but not limited to toluene, with the reaction carried out under heating conditions between about 50° C. to about 110° C. for about 12 to about 20 hours will provide compounds of formula 3 which are representative of compounds of the invention.

The general reaction of amines with aryl halides and aryl triflates is well known to those of ordinary skill in the art of organic synthesis. The reaction of amines with aryl halides and aryl triflates is known to proceed in the presence of sodium t-butoxide (NaOt-Bu) or cesium carbonate (Cs$_2$CO$_3$) in the presence of a metal catalyst such as, but not limited to, copper metal or CuI, palladium diacetate (Pd(OAc)$_2$) or tris (dibenzylideneacetone)dipalladium (Pd$_2$ dba$_3$), and also optionally with a ligand such as, but not limited to, BINAP, or tri-tert-butylphosphine ((t-Bu)$_3$P) under ambient or heated conditions to provide new compounds wherein the nitrogen of the amine moiety has displaced the halide or triflate of the aryl halides and aryl triflate. The reaction can be performed in a solvent such as dioxane, toluene, or pyridine. References that describe examples of the methodologies may be found in the following: J. Hartwig, et al., Angew. Chem. Int. Ed., 37:2046-2067 (1998); J. P. Wolfe et al., Acc. Chem. Res., 13:805-818 (1998); J. P. Wolfe et al., J. Org. Chem., 65:1158-1174 (2000); F. Y. Kwong et al., Org. Lett., 4:581-584 (2002); and B. H. Yang et al., J. Organomet. Chem., 576:125-146 (1999).

Diamine compounds of general formula 1 described in Scheme 1 are available by general routes and methods described in the literature. For specific examples, Schenke, et al. (U.S. Pat. No. 5,071,999) describes 5,6-dimethyloctahydropyrrolo[3,4-b]pyrrole where $R^1$ and $R^{2f}$ are methyl, and $R^{2a}$, $R^{2b}$, $R^{2c}$, $R^{2d}$, and $R^{2e}$ are hydrogen is described. Also described in Schenke, et al. (U.S. Pat. No. 5,071,999) is a 3-fluoro-5-methyloctahydropyrrolo[3,4-b]pyrrole wherein $R^1$=methyl, $R^{2b}$=fluoro, and $R^{2a}$, $R^{2c}$, $R^{2d}$, $R^{2e}$, and $R^{2f}$ are hydrogen. In the same reference (Schenke, et al. U.S. Pat. No. 5,071,999) is described ethyl 3-methylhexahydropyrrolo[3,4-b]pyrrole-5(1H)-carboxylate, a compound which may be treated with lithium aluminum hydride in THF to reduce the ethyl carbamate group to a methyl group and produce 3,5-dimethyloctahydropyrrolo[3,4-b]pyrrole, wherein $R^1$ and $R^{2c}$ are methyl, and $R^{2a}$, $R^{2b}$, $R^{2d}$, $R^{2e}$, and $R^{2f}$ are hydrogen. In the same reference (Schenke, et al. U.S. Pat. No. 5,071,999) is described ethyl 3-methyl-2,7-diazabicyclo[3.3.0]octane-7-carboxylate, a compound which may be treated with lithium aluminum hydride in THF to reduce the ethyl carbamate groups to a methyl groups and produce 2,5-dimethyloctahydropyrrolo[3,4-b]pyrrole wherein $R^1$ and $R^{2d}$ are methyl, and $R^{2a}$, $R^{2b}$, $R^{2c}$, $R^{2e}$, and $R^{2f}$ are hydrogen. In Basha, et al. (US Patent Publication 2005/0101602A1) is described 6a-methyl-hexahydro-pyrrolo[3,4-b]pyrrole-1-carboxylic acid benzyl ester, which after treatment with methyl iodide followed by treatment with HBr in acetic acid to remove the benzyl ester, will provide 5,6a-dimethyloctahydropyrrolo[3,4-b]pyrrole, wherein $R^1$ and $R^{2e}$ are methyl, and $R^{2a}$, $R^{2b}$, $R^{2c}$, $R^{2d}$, and $R^{2f}$ are hydrogen. In the case where compounds of formula (I) are present as a racemic mixture, and it is desired that enantiomerically purified products be isolated, column chromatography of the racemic mixture on a chiral column may be utilized to separate one or both enantiomers.

Scheme 2

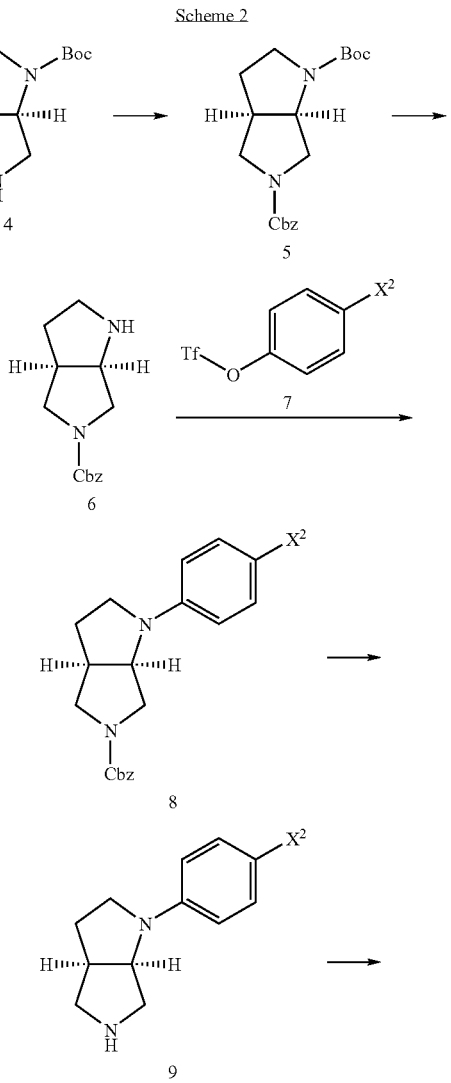

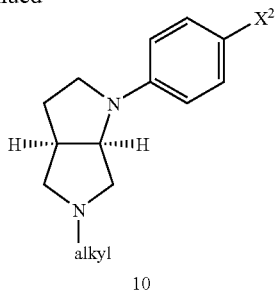

10

Alternatively, the nitrogen of compound formula 4, may be protected with a benzyloxycarbonyl protecting group utilizing N-(benzyloxycarbonyloxy)-succinimide or benzyloxycarbonyl chloride, and a base such as diisopropylethylamine in solvents such as dichloromethane to provide a compound of formula 5. Compounds of formula 5 may undergo acid catalyzed removal of the butoxycarbonyl group when treated with an acid such as trifluoroacetic acid in a solvent such as dichloromethane, to provide a compound of formula 6. Compound of formula 6, when treated with a compound of formula 7 according to conditions outlined in Scheme 1 will provide compounds of formula 8. The removal of the benzyloxycarbonyl protecting group using heated trifluoroacetic acid or other acids such as HBr in acetic acid or by hydrogenolysis utilizing hydrogen gas and a palladium catalyst are processes well known by those skilled in the art, and will provide compounds of formula 9. Compounds of formula 9 when treated with a base such as sodium hydride in a solvent such as but not limited to THF followed by the addition of an alkyl halide and will provide compounds of formula 10 which are representative of compounds of the invention. Alternative methods of direct alkyation of compounds of formula 9 are available by treatment of alkyl halides and triflates with compounds of formula 9 in solvents such as but not limited to dichloromethane, toluene, ethyl acetate, at temperatures ranging from −78 to 150° C., optionally in the presence of a base such as sodium carbonate, sodium bicarbonate, cesium carbonate, or triethylamine to produce compounds of formula 10. Other methods for the conversion of compounds of formula 9 into compounds of formula 10 involve treatment with sodium cyanoborohydride in a solvent such as THF with carbonyl compounds such as paraformaldehyde, acetone, or acetaldehyde. Yet another method for the conversion of compounds of formula 9 to compounds of formula 10 involves reaction of compounds of formula 9 with a carbonyl compound in dichloromethane in the presence of sodium triacetoxyborohydride, as is well known to those skilled in the art, and as described in Abdel-Magid, et al. in the Journal of Organic Chemistry (1996) 61, p. 3849-3862.

Compound of formula 4 (CAS #370880-09-4, also known as pyrrolo[3,4-b]pyrrole-1(2H)-carboxylic acid, hexahydro-1,1'-dimethylethyl ester, (3aR,6aR) or (3aR,6aR)-tert-butyl hexahydropyrrolo[2,3-c]pyrrole-1(2H)-carboxylate is available from methods described in Basha, et al. U.S. Pat. Appl. Publ. (2005) 2005101602 A1 and Schrimpf, et al. PCT Int. Appl. (2001), WO 2001081347 A2. Compound of formula 4 is available in racemic form commercially from J & W PharmLab LLC, 1300 W Steel Rd, Unit #1, Morrisville, Pa., 19067, USA and from Anichem LLC, 1 Deer Park Dr., Suite P, Monmouth Junction, N.J., 08852. An alternative preparation of compounds of formula 4 may be obtained by hydrogenolytic removal (with palladium and hydrogen gas) of the benzyl moiety from tert-butyl 1-benzylhexahydropyrrolo[2,3-c]pyrrole-5(1H)-carboxylate, to provide a compound produced as a racemic mixture is provided in Schenke, T., et al, U.S. Pat. No. 5,071,999, (1991); the isolation of enantiomerically purified products from racemic mixtures by column chromatography on a chiral column is well known to those of ordinary skill in the art of organic synthesis, will provide enantiomerically pure (3aR,6aR)-tert-butyl hexahydropyrrolo[3,4-b]pyrrole-5(1H)-carboxylate, from its racemic form.

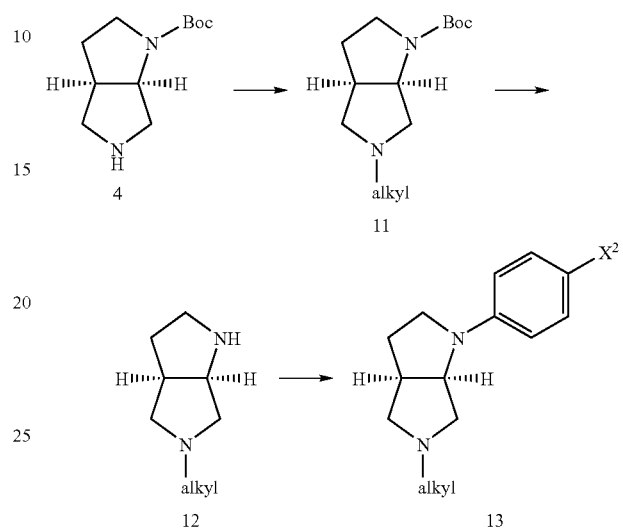

Compounds of formula 4 may also be treated directly with a base such as sodium hydride or sodium carbonate in a solvent such as THF followed by an alkyl halide to provide compounds of formula 11. Alternatively, compounds of formula 4 when treated with paraformaldehyde, an alkylaldehyde or alkyl ketone, followed by treatment with sodium cyanoborohydride will provide compounds of formula 11. Compounds of formula 11 when treated with a mixture of trifluoroacetic acid and dichloromethane will provide compounds of formula 12. Compounds of formula 12 when treated with compounds of formula 2 according to conditions outlined in Scheme 1 will provide compounds of formula 13 which are representative of compounds of the invention. Alternatively, the method of direct alkyation of compounds of formula 4 by treatment of alkyl halides or triflates with compounds of formula 4 in solvents such as but not limited to dichloromethane, toluene, ethyl acetate, optionally in the presence of a base such as sodium carbonate, sodium bicarbonate, cesium carbonate, or triethylamine to produce compounds of formula 11.

Scheme 4

[Structure 14]

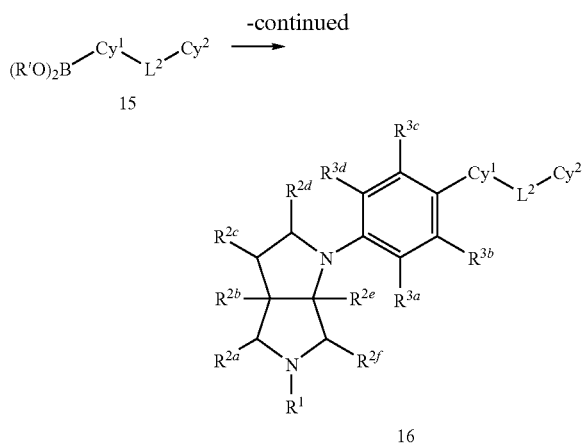

Compounds of formula 14, which may be prepared according to the methods outlined in Scheme 1, wherein $X^2$ is $R^6$ and $R^6$ is bromide may be treated according to methods known to one skilled in the art to provide compounds of formula 16, which are representative of compounds of the invention. Compound of formula 14 when treated with compounds of formula 15, wherein $Cy^2$ is aryl or heteroaryl, as defined within the scope of formula (I), in the presence of palladium acetate, 2-(dicyclohexlphosphino)biphenyl and potassium phosphate in a mixture of solvents such as but not limited to toluene, isopropanol and water under heated conditions of about 60° C. to about 75° C. will provide compounds of formula 16.

The reaction of aryl and heteroaryl halides and triflates, such as those represented by compounds of formula 14 with aryl and heteroaryl boronic acids, boronic acid esters, and pinacol boranes in the presence of a base such as sodium carbonate, $K_3PO_4$, or KF in a solvent such as tetrahydrofuran or toluene, in the presence of a palladium source such as palladium diacetate, $PdCl_2(PPh_3)_2$, or $Pd(PPh_3)_4$, and a ligand such as triphenylphosphine, 2-(dicyclohexylphosphino)biphenyl, tri-t-Butylphosphine, or tris(2-furyl)phosphine is well known to those skilled in the art as a Suzuki reaction. The general methodology has been reviewed for example in J. Tsuji, Palladium Reagents and Catalysts-Innovations in Organic Synthesis, John Wiley & Sons: New York, 1995. Reference describing the preparation of boronic acids such as compounds of formula 15 may be found for example in B. T. O'Neill, et al., Organic Letters, 2:4201 (2000); M. D. Sindkhedkar, et al., Tetrahedron, 57:2991 (2001); W. C. Black, et al., Journal of Medicinal Chemistry, 42:1274 (1999); Letsinger; Dandegaonker, J. Amer. Chem. Soc., 81:498-501 (1959); Carroll, F. Ivy, et al. J. Med. Chem., 2229-2237 (2001).

Boronic acids and esters of formula 15 include both boronic acids wherein R' is H, boronic acid esters wherein R' is an alkyl such as methyl or isopropyl, and also includes pinacol borane esters wherein the two R'O groups taken together with the boron atom form a 4,4,5,5-tetramethyl-[1,3,2]dioxaborolanyl moiety. There are many aryl, heteroaryl, and heterocyclic boronic acids and boronic acid esters that are available commercially or that can be prepared as described in the scientific literature of synthetic organic chemistry. Examples of boronic acid and boronic acid ester reagents are shown in the following table.

TABLE

Examples of Boronic Acid and Boronic Acid Ester Reagents

| Boronic Acid or Boronic Acid Ester | Commercial Source, Chemical Abstracts Number (CAS #), or Literature Reference |
|---|---|
| 2-pyrimidinone-5-boronic acid | CAS #373384-19-1 |
| 2-methoxypyrimidine-5-boronic acid | Frontier Scientific, Inc., Logan, UT, USA |
| 1H-pyrimidine-2,4-dione-5-boronic acid | Specs, Fleminglaan, the Netherlands CAS #70523-22-7; Schinazi, Raymond F.; Prusoff, William H., Synthesis of 5-(dihydroxyboryl)-2'-deoxyuridine and related boron-containing pyrimidines, Journal of Organic Chemistry (1985), 50(6), 841-7. |
| pyridine-3-boronic acid | CAS #1692-25-7, Frontier Scientific, Inc., Logan, UT, USA |
| 2,4-dimethoxypyrimidine-5-boronic acid | CAS #89641-18-9, Frontier Scientific, Inc., Logan, UT, USA |
| 2-methoxy-5-pyridine boronic acid | Digital Specialty Chemicals, Dublin, NH; CAS #163105-89-3; New shelf-stable halo- and alkoxy-substituted pyridylboronic acids and their Suzuki cross-coupling reactions to yield heteroarylpyridines, Parry, Paul R.; Bryce, Martin R.; Tarbit, Brian, Department of Chemistry, Synthesis (2003), (7), 1035-1038; Functionalized Pyridylboronic Acids and Their Suzuki Cross-Coupling Reactions To Yield Novel Heteroarylpyridines, Parry, Paul R.; Wang, Changsheng; Batsanov, Andrei S.; Bryce, Martin R.; Tarbit, Brian, Journal of Organic Chemistry (2002), 67(21), 7541-7543. |
| pyrimidine-5-boronic acid | CAS #109299-78-7, S. Gronowitz, et al., "On the synthesis of various thienyl- and selenienylpyrimidines", Chem. Scr. 26(2): 305-309 (1986). |

TABLE-continued

Examples of Boronic Acid and Boronic Acid Ester Reagents

| | |
|---|---|
| pyrimidine-5-boronic acid, pinacol ester | Umemoto, et al., Angew. Chem. Int. Ed. 40(14): 2620-2622 (2001). |
| 2-methylpyridine-5-boronic acidhydrate | SYNCHEM OHG Heinrich-Plett-Strassse 40; Kassel, D-34132; Germany; CAS #659742-21-9 |
| 2H-Pyran, 3,6-dihydro-4-(4,4,5,5-tetramethyl-1,3,2-dioxaborolan-2-yl) | CAS # 287944-16-5; Murata, Miki; Oyama, Takashi; Watanabe, Shinji; Masuda, Yuzuru, Synthesis of alkenylboronates via palladium-catalyzed borylation of alkenyl triflates (or iodides) with pinacolborane. Synthesis(2000), (6), 778-780. |
| 1(2H)-Pyridinecarboxylic acid, 3,6-dihydro-4-(4,4,5,5-tetramethyl-1,3,2-dioxaborolan-2-yl)-, 1,1-dimethylethyl ester | CAS # 286961-14-6; A versatile synthesis of 4-aryltetrahydropyridines via palladium mediated Suzuki cross-coupling with cyclic vinyl boronates, Eastwood, Paul R., Discovery Chemistry, Aventis Pharma, Essex, UK., Tetrahedron Letters (2000), 41(19), 3705-3708. |
| (5-cyano-3-pyridinyl)-boronic acid | CAS # 497147-93-0; Chemstep Institut du PIN - University Bordeaux 1 351 cours de la liberation Talence Cedex, 33450 France |
| Thianthrene-1-boronic acid | Aldrich Chemical Company, Inc. |
| Benzoxazole-5-boronic acid | Cat # 110831, Asymchem Laboratories, Inc. |
| Benzothiazole-5-boronic acid | Cat # 1464, Digital Specialty Chemicals, Inc. |
| 4-Methyl-7-(4,4,5,5-tetramethyl-1,3,2-dioxaborolan-2-yl)-3,4-dihydro-2h-1,4-benzoxazine | Cat # CC13539CB, Acros Organics USA |
| 10-Methyl-3-(4,4,5,5-tetramethyl-[1,3,2]dioxaborolan-2-yl)-10H-phenothiazine | Kraemer, C. S.; et. al. Synthesis 2002, 9, 1163-1170. |
| (1,4-Dihydro-4,4-dimethyl-2-oxo-2H-3,1-benzoxazin-6-yl)boronic acid | Zhang, P.; et. al. J. Med.Chem. 2002, 45, 4379-4382. |

Pinacolboronate esters may be prepared by procedures such as those described in Takagi et al. Tetrahedron Letters, 43:5649-5651 (2002), N. Miyaura et al., Chem. Rev. 95:2457 (1995) or references cited within the article, and Ishiyama, et al. Tetrahedron, 9813-9816 (2001).

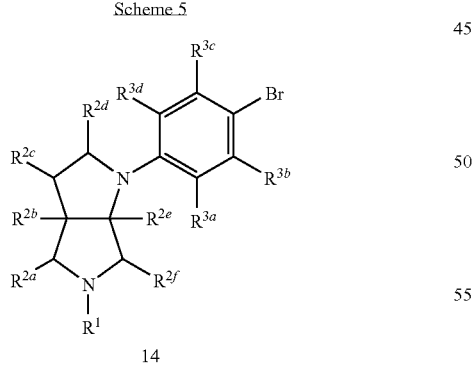

Scheme 5

14

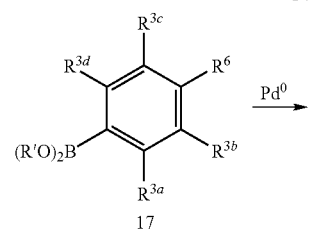

17

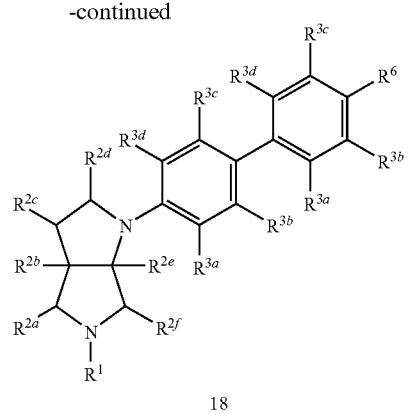

-continued

18

Similarly, in a Suzuki reaction, compounds of formula 14 may be treated with phenyl boronic acids of formula 17, in the presence of palladium diacetate, 2-(dicyclohexlphosphino) biphenyl and potassium phosphate ($K_3PO_4$) or sodium carbonate in a mixture of solvents such as but not limited to toluene, isopropanol and water under heated conditions of about 30° C. to about 150° C. to provide compounds of formula 18.

Scheme 6

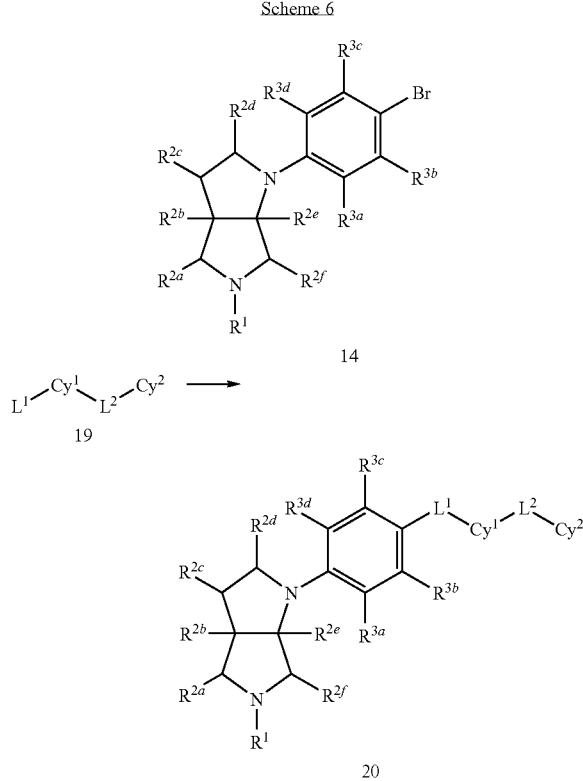

Alternatively, compounds of formula 14 may also be used to generate compounds of formula 20 which are representative of compounds of formula (I). Compounds of formula 14 when treated with compounds of formula 19, wherein $L^1$ is a heteroatom such as oxygen, sulfur or nitrogen, in the presence of copper powder and potassium carbonate in quinoline under heated conditions between about 120° C. to about 150° C. will provide compounds of formula 20 which are representative of compounds of the invention. Alternative methodologies that describe the reaction of halides such as compounds of formula 14 with compounds of formula 19 where $L^1$ is nitrogen as for example $NH_2$ or NH(alkyl) in the presence of sodium t-butoxide or cesium carbonate in the presence of a metal catalyst such as, but not limited to copper metal or CuI, palladium diacetate, and also optionally with a ligand such as, but not limited to, BINAP, tri-tertbutylphosphine in solvents such as dioxane, toluene, and pyridine, are well known to those skilled in the art, with examples described in J. Hartwig, et al., Angew. Chem. Int. Ed., 37:2046-2067 (1998); J. P. Wolfe et al., Acc. Chem. Res., 13:805-818 (1998); J. P. Wolfe et al., J. Org. Chem., 65:1158-1174 (2000); F. Y. Kwong et al., Org. Lett., 4:581-584, (2002); and B. H. Yang et al., J. Organomet. Chem., 576:125-146 (1999).

Alternative methodologies that describe the reaction of halides such as compounds of formula 14 with compounds of formula 19 where $L^1$ is oxygen as for example hydroxyl in the presence of a base such as but not limited to sodium hydride in a solvent such as toluene or N,N-dimethylformamide in the presence of a metal-containing catalyst such as CuI or palladium diacetate are well known to those skilled in the art, with examples described in Hartwig et al., Angew. Chem. Int. Ed., 37:2046-2067 (1998); K. E. Torraca et al., J. Amer. Chem. Soc., 123:10770-10771 (2001); S. Kuwabe et al., J. Amer. Chem. Soc., 123:12202-12206 (2001); K. E. Toracca et al., J. Am. Chem. Soc., 122:12907-12908 (2000); R. Olivera et al., Tet. Lett., 41:4353-4356 (2000); J.-F. Marcoux et al., J. Am. Chem. Soc., 119:10539-10540 (1997); A. Aranyos et al., J. Amer. Chem. Soc., 121:4369-4378 (1999); T. Satoh et al., Bull. Chem. Soc. Jpn., 71:2239-2246 (1998); J. F. Hartwig, Tet. Lett., 38:2239-2246 (1997); M. Palucki et al., J. Amer. Chem. Soc., 119:3395-3396 (1997); N. Haga et al, J. Org. Chem., 61:735-745 (1996); R. Bates et al., J. Org. Chem., 47:4374-4376 (1982); T. Yamamoto et al., Can. J. Chem., 61:86-91 (1983).

Alternative methodologies that describe the reaction of halides such as compounds of formula 14 with compounds of formula 19 where $L^1$ is sulfur such as a thiol in the presence of a base with or without a metal catalyst such as CuI or palladium diacetate in a solvent such as dimethylformamide or toluene are described in G. Y. Li et al., J. Org. Chem., 66:8677-8681 (2001); Y. Wang et al., Bioorg. Med. Chem. Lett., 11:891-894 (2001); G. Liu et al., J. Med. Chem., 44:1202-1210 (2001); G. Y. Li et al., Angew. Chem. Int. Ed., 40:1513-1516 (2001); U. Schopfer et al., Tetrahedron, 57:3069-3074 (2001); and C. Palomo et al., Tet. Lett., 41:1283-1286 (2000).

Scheme 7

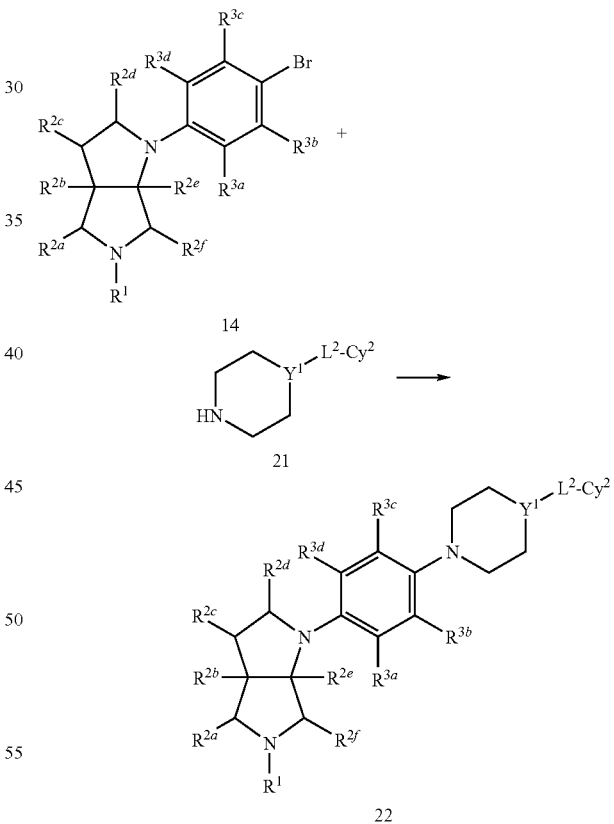

Compounds of formula 14 may also be used to generate compounds of formula 22 which are representative of compounds of formula (I) wherein $L^1$ is a bond and $Cy^1$ is a nitrogen containing heterocycle. Compounds of formula 14 when treated with compounds of formula 21 wherein $Y^1$ is a bond or is selected from the group consisting of CH and N, in the presence of copper powder and potassium carbonate in quinoline under heated conditions between about 120 to about 150° C. will provide compounds of formula 22 which are representative of compounds of the invention.

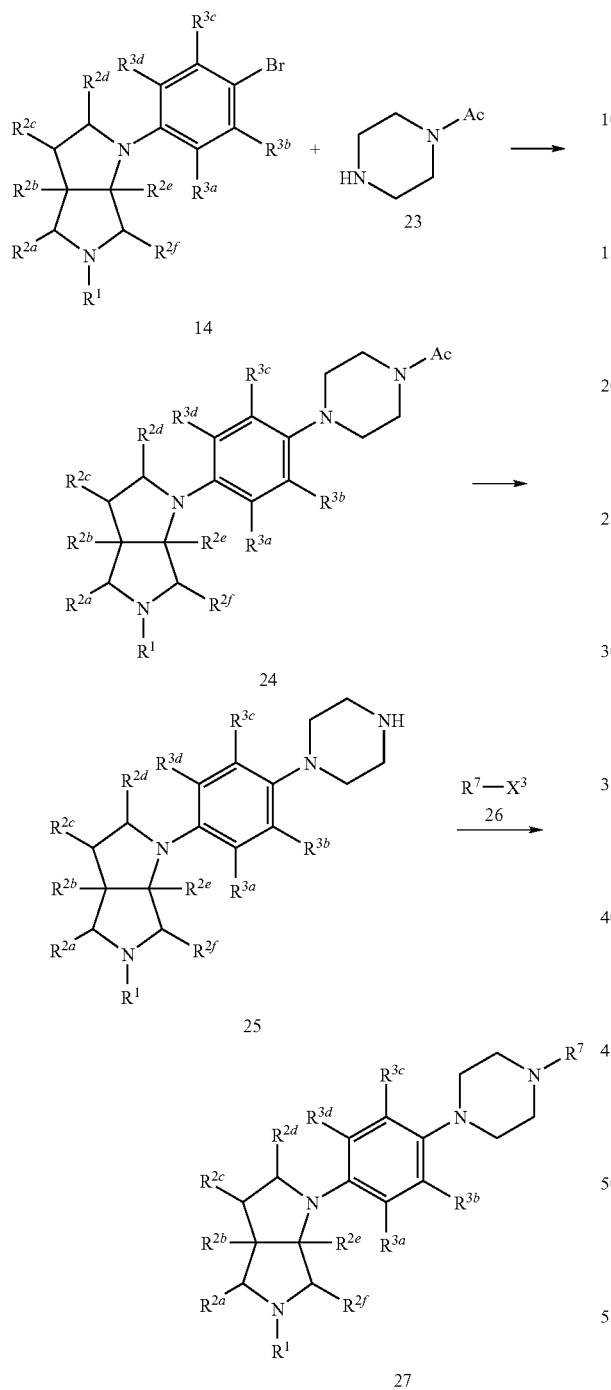

Similarly, compounds of formula 14 when treated with 1-acetylpiperazine, the compound of formula 23, in the presence of tris(dibenzylideneacetone)dipalladium, (R)-(+)-2,2'-bis(diphenylphosphino)-1,1'-binaphthyl and sodium tert-butoxide in toluene subjected to microwave heating under heated microwave conditions will provide compounds of formula 24. The compounds of formula 24 when treated according to conditions known to remove an acetyl group from a nitrogen atom such as but not limited to heating a the compound in a mixture of 2N HCl and methanol will provide compounds of formula 25. The conditions suitable to convert compounds of formula 25 into compounds of formula 27 may vary based on the reactivity of compounds of formula 26. The treatment of compounds of formula 25 with compounds of formula 26 ($R^7$—$X^3$), wherein $R^7$ is aryl, cycloalkyl, cycloalkenyl, heteroaryl or heterocycle and $X^3$ is halogen or another appropriate electrophile known to one skilled in the art, will provide compounds of formula 27 maybe carried out under different conditions depending on the reagent, $R^7$—$X^3$. When $R^7$ is cycloalkyl, cycloalkenyl, heterocycle or certain heteroaryl rings and $X^3$ is a halogen or triflate ($F_3CSO_2O$—), the conversion may be carried out by heating a mixture in a solvent such as acetonitrile in the presence of a base such as but not limited to triethylamine. When $R^7$ is aryl or heteroaryl then the conversion can be carried out by heating the mixture in the presence of tris(dibenzylideneacetone)dipalladium, racemic-2,2'-bis(diphenylphosphino)-1,1'-binaphthyl and sodium tert-butoxide in a solvent such as toluene at 30-150° C.

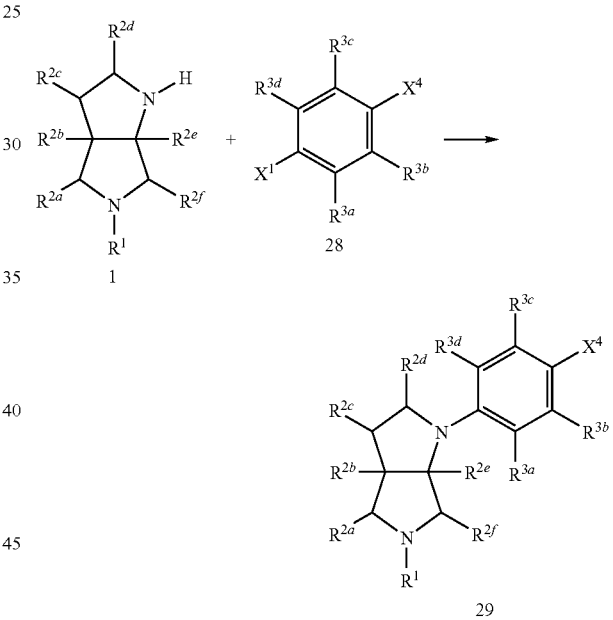

In addition, compounds of formula 29 are obtained by the treatment of compounds of formula 1 with compounds of formula 28, wherein $X^1$ is a halogen (Cl, Br, I) or a triflate ($CF_3SO_2O$) using conditions outlined in Scheme 1. Compounds of formula 28 may be obtained from commercial sources, or are readily available according to methods described in the scientific literature, or in the case where $X^1$ is a triflate may be made from phenols by treatment with triflic anhydride in the presences of a base. Examples of readily available suitable compounds of formula 28 include but are not limited to 1,4-dibromo-2,5-difluorobenzene, 2,5-dibromo(trifluoromethoxy)benzene, 4-bromo-2-fluorophenol, and 5-bromo-2-iodobenzonitrile.

Furthermore, compounds of formula 29 which contain an $X^4$ group that is a bromide, may be further treated according the methods outlined in Schemes 4, 5, 6, 7 or 8 to generate compounds of formula 16, 18, 20, 22 or 27, respectively which are representative of compounds of the invention.

Scheme 10

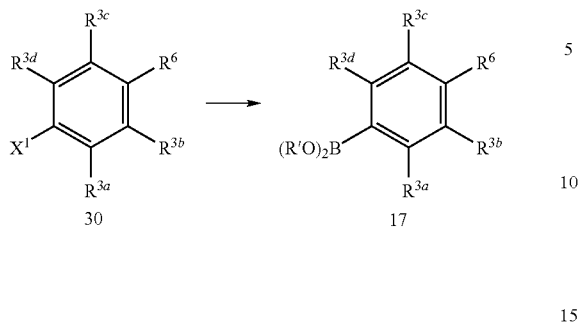

A wide variety of compounds of formula 17 are available from commercial suppliers. In addition, compounds of formula 17 are also available synthetically through methods described in the scientific literature, or may be prepared from compounds of formula 30 by methods described in Scheme 10. Compounds of formula 17 include include both boronic acids wherein R' is H, and boronic acid esters wherein R' is an alkyl such as methyl or isopropyl, and also includes pinacol borane esters wherein the two R'O groups taken together with the boron atom form a 4,4,5,5-tetramethyl-[1,3,2]dioxaborolanyl moiety.

Scheme 11

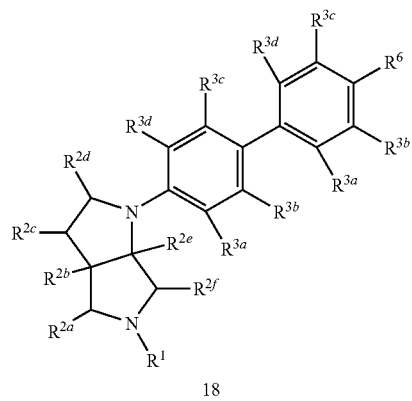

Compounds of formula 18, wherein $R^6$ is a halogen may be treated with aryl boronic acids or aryl boronic esters according to the procedure outlined in Scheme 4, to provide compounds of formula 31 wherein $Cy^3$ is an aryl ring. Alternatively, compounds of formula 18, wherein $R^6$ is a halogen may also be treated with heteroaryl boronic acids or heteroaryl boronic esters according to the procedure outlined in Scheme 4, to provide compounds of formula 31 wherein $Cy^3$ is a heteroaryl.

Compounds of formula 31 wherein $Cy^3$ is a heterocyclic or heteroaryl ring connected to the parent molecular moiety through a nitrogen atom contained within the ring, may be prepared by the treatment of a heteraromatic compound or a heterocyclic compound with a compound of formula 18 wherein $R^6$ is a halogen or triflate. The conditions needed to effected this transformation include but are not limited to heating in the presence of a base such as, but not limited to, sodium t-butoxide or cesium carbonate, in the presence of a metal catalyst such as, but not limited to copper metal or CuI, palladium diacetate, optionally with a ligand such as, but not limited to, BINAP, tri-tertbutylphosphine in solvents such as dioxane, toluene and pyridine. References that describe these methodologies may be found in the following references: J. Hartwig et al., Angew. Chem. Int. Ed. 37:2046-2067 (1998); J. P. Wolfe et al., Acc. Chem. Res., 13:805-818 (1998); M. Sugahara et al., Chem. Pharm. Bull., 45:719-721 (1997); J. P. Wolfe et al., J. Org. Chem., 65:1158-1174, (2000); F. Y. Kwong et al., Org. Lett., 4:581-584, (2002); A. Klapars et al., J. Amer. Chem. Soc., 123:7727-7729 (2001); B. H. Yang et al., J. Organomet. Chem., 576:125-146 (1999); A. Kiyomori et al., Tet. Lett., 40:2657-2640 (1999); Hartwig, J. Org. Chem., 64(15):5575-5580 (1999); Pu, et al. Tetrahedron Letters (2006) vol. 47 p 149; WO 0024719, p. 127, Example 62. Examples of suitable heterocyclic and heteroaromatic reagents include but are not limited to piperidin-2-one, 1H-pyridin-2

Scheme 12

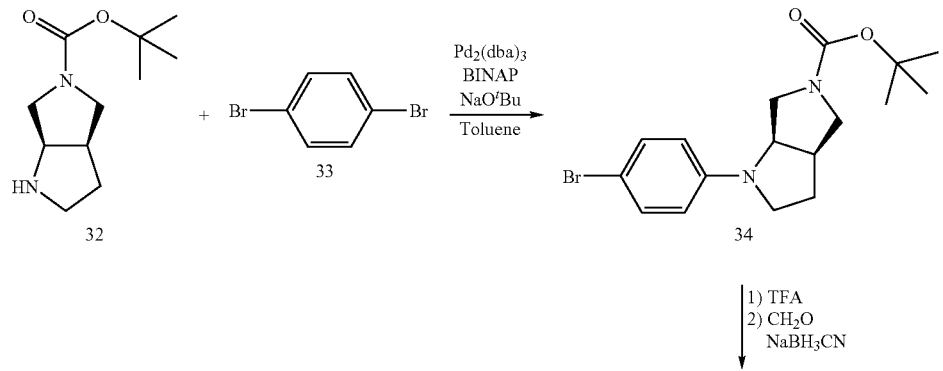

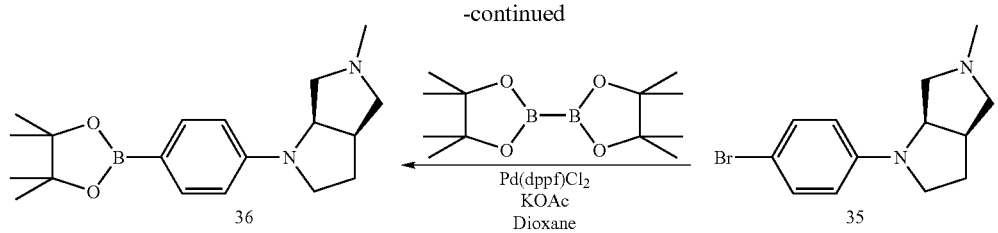

Similarly, the compound of formula 32, protected by a tert-butyloxycarbonyl protecting group (Boc), when treated with 1,4-dibromobenzene along with tris(dibenzylideneacetone)dipalladium (Pd$_2$(dba)$_3$), racemic-2,2'-bis(diphenylphosphino)-1,1'-binaphthyl (BINAP), sodium tert-butoxide in toluene as described in Scheme 1, will provide the compound of formula 34. The removal of the Boc protecting group using TFA in dichloromethane followed by reductive amination using formaldehyde and sodium cyanoborohydride will provide the compound of formula 35. The treatment of the compound of formula 35 with 4,4,4',4',5,5,5',5'-octamethyl-2,2'-bi(1,3,2-dioxaborolane), Pd(dppf)Cl$_2$ and potassium acetate in dioxane will provide compounds of formula 36.

Scheme 13

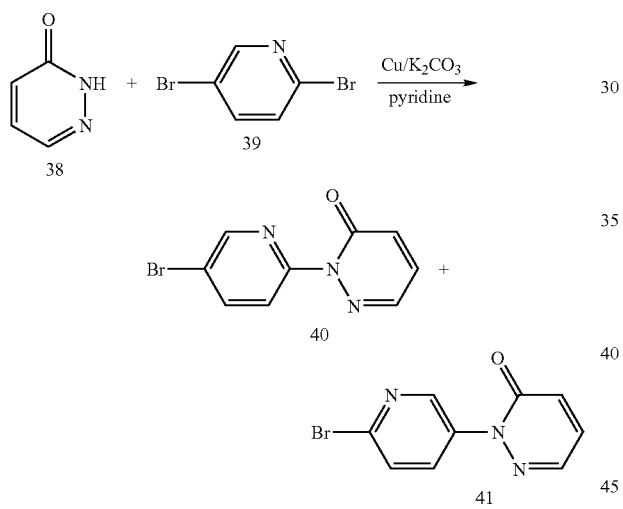

Compounds of the present invention containing a heteroaryl ring such as but not limited to a pyridinyl ring in the Cy$^1$ position may be prepared by following the procedures outlined in Scheme 13 followed by the procedure outlined in either Scheme 13 or Scheme 14. The compound of formula 38 when treated with the compound of formula 39 in the presence of copper and potassium carbonate in pyridine under heated conditions will provide a mixture of both the compound of formula 40 and the compound of formula 41. The mixture of compounds is separable utilizing chromatographic procedures known to one skilled in the art.

Scheme 14

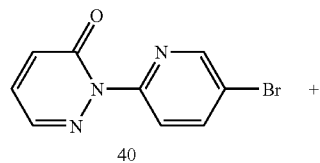

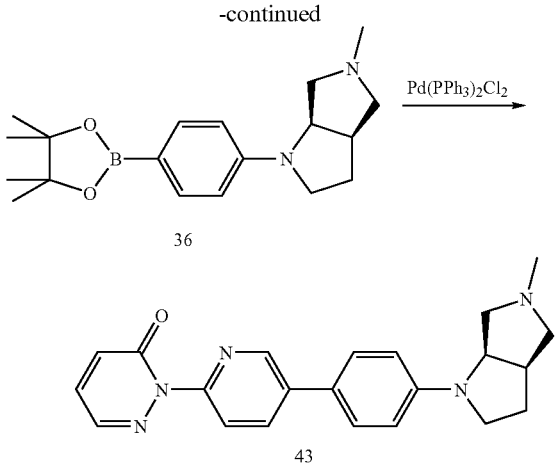

The compound of formula 40 and the compound of formula 36 when heated and microwaved in the presence of dichloroditriphenylphosphino palladium, 2-(dicyclohexylphosphino)biphenyl, and Na$_2$CO$_3$ in a solvents such as a mixture of ethanol and dioxane will provide the compound of formula 43.

Scheme 15

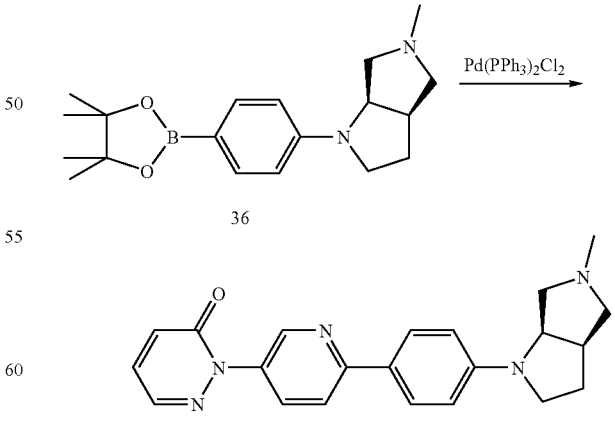

Similarly, compound of formula 41 and compound of formula 36 when treated according to the procedure outlined in Scheme 14, will provide the compound of formula 44.

Scheme 16

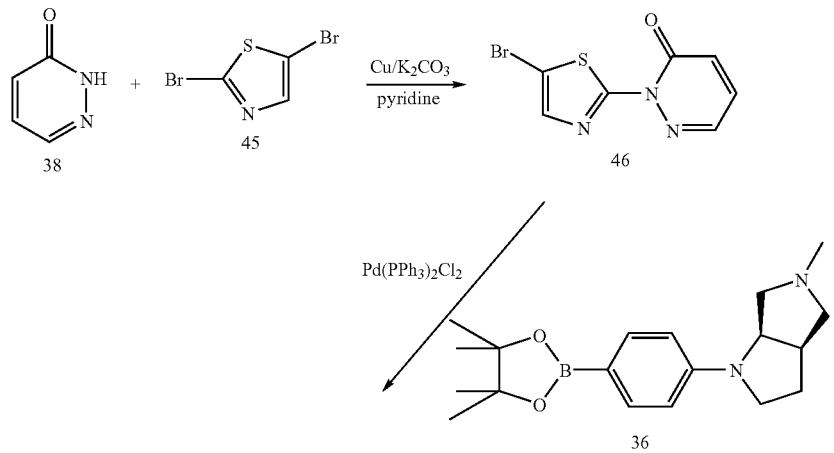

Examples of other heteroaryl rings in the Cy$^1$ position of the compounds of formula (I) may be prepared accordingly. For example, the compound of formula 38 when treated with the compound of formula 45 according to the procedure outlined in Scheme 13 will provide the compound of formula 46. The compound of formula 46 when treated with the compound of formula 36 according to the procedure outlined in Scheme 14 will provide the compound of formula 47.

Scheme 17

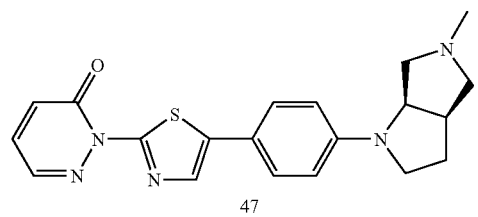

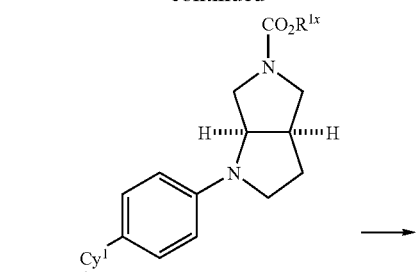

-continued

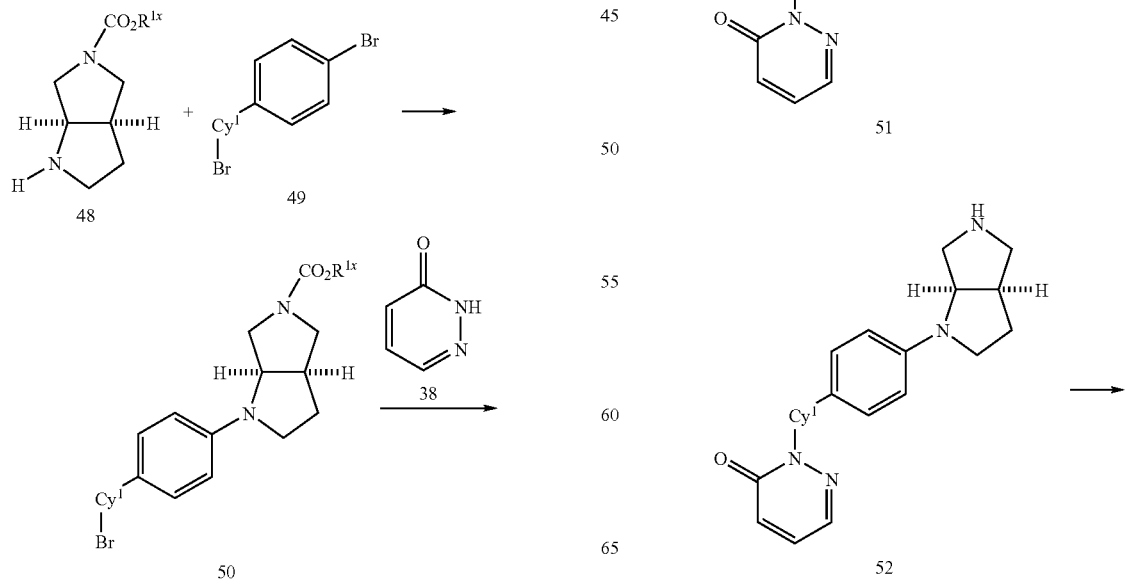

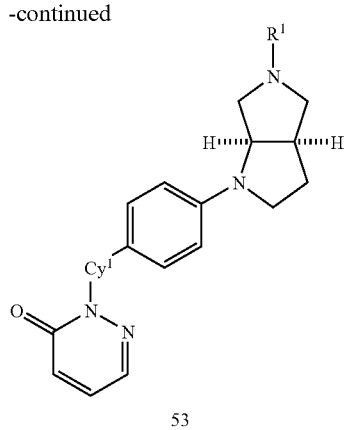

53

Similarly, compounds of formula 48, wherein $R^{1x}$ is alkyl, when heated with compounds of formula 49, wherein $Cy^1$ is aryl, and preferably is phenyl, in the presence of palladium acetate, Xantphos, and cesium carbonate will provide compounds of formula 50. Alternatively, other carbonate bases also can be suitable, for example potassium carbonate. Typical conditions include but are not limited to heating the mixture of 2 molar equivalents of compounds of formula 49 with 1 molar equivalent of compounds of formula 50 along with 2 molar equivalents of cesium carbonate and catalytic quantities of palladium acetate and Xantphos in toluene at a temperature of about 80° C. to about 110° C., and preferably about 95° C. Compounds of formula 50 when heated in the presence of compounds of formula 38 with copper iodide, or copper powder with a base in a polar, high-boiling solvent, for example DMF, DMA, pyridine, or 4-methylpyridine. Preferred conditions are heating compounds of formula 50 in the presence of compounds of formula 38 along with 8-hydroxyquinoline, copper iodide, and potassium carbonate, in a solvent such as DMF, to provide compounds of formula 51. Compounds of formula 51, wherein $R^{1x}$ is alkyl such as methyl or ethyl, and preferably ethyl, when treated with 33% HBr in acetic acid while heated to about 65 to about 75° C. will provide compounds of formula 52 isolated as a salt. Alternatively, compounds of formula 51 can be treated with base in ethylene glycol to provide compounds of formula 52. Accordingly, compounds of formula 52 may be used to provide compounds of formula 53 which are representative of compounds of the present invention. Therefore, contemplated within the scope of the invention is the process of preparing the compounds of formula (III),

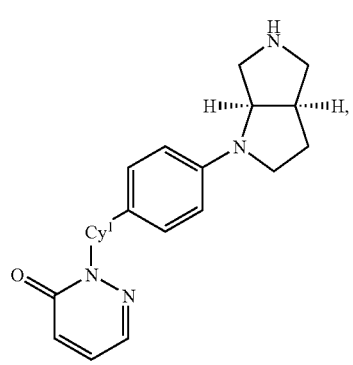

wherein $Cy^1$ is aryl, preferably phenyl, which are useful for the preparation of some compounds of formula (I). In addition, the process also discloses the treatment of a compound of formula (III) with alkylating conditions to provide compounds of formula (IV)

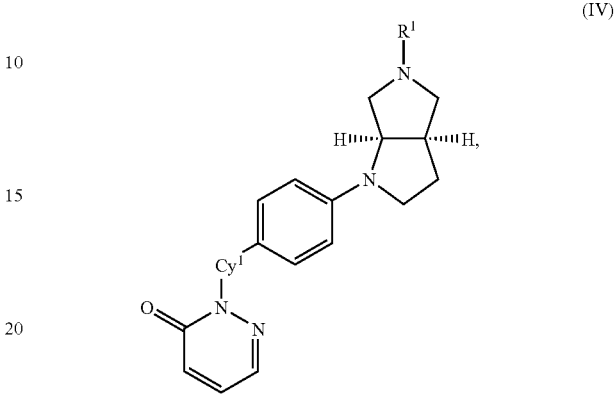

wherein $R^1$ is an alkyl group. The alkylating conditions comprise treating a mixture of a compound of formula (III) and formaldehyde, acetaldehyde, or cycloalkyl ketones, with a reducing agent such as sodium triacetoxyborohydride, sodium cyanoborohydride, or sodium borohydride. In a preferred embodiment, the alkylating conditions comprises treating a mixture of a compound of formula (III) and formaldehyde with sodium triacetoxyborohydride.

The treatment of compounds of formula 52 with alkylating conditions known to one skilled in the art will provide compounds of formula 53. For example, the treatment of compounds of formula 52 with a base such as lithium diisopropylamide or lithium bis(trimethylsilyl)amide in a solvent such as THF or dioxane at a temperature between about −78° C. to about 0° C. followed by treatment with a compound of formula $R^1$—X, wherein $R^1$ is defined in formula (I) and X is chloro, bromo, iodo, mesyl or triflate will provide compounds of formula 53. Alternative conditions for a base mediated alkylation include the treatment of compounds of formula 52 with sodium hydride in DMF at about −10° C. to about 0° C. followed by treatment with $R^1$—X will provide compounds of formula 53. Furthermore, the treatment of the mixture of compounds of formula 52 and $R^1$—X with sodium hydroxide in a mixture of water and an appropriate organic solvent containing a phase transfer catalyst known to one skilled in the art will provide compounds of formula 53. Alternatively, treatment of compounds of formula 52 with reductive amination conditions known to those skilled in the art will provide compounds of formula 53. Accordingly, the treatment of compounds of formula 52 with aldehydes, such as but not limited to formaldehyde, acetaldehyde, or cycloalkyl ketones, in the presence of a reducing reagent, such as but not limited to sodium triacetoxyborohydride, sodium cyanoborohydride, or sodium borohydride, provides compounds of formula 53.

The process of preparing compounds of formula (III) relates to heating the mixture of the compounds of formula (IIIa) (wherein P is a nitrogen protecting group such as but not limited to alkoxycarbonyl compounds), with compounds of formula (IIIb) (wherein $Cy^1$ is aryl), and with a carbonate base, a palladium source, and Xantphos in a solvent. Suitable carbonate bass are, for example, potassium carbonate or cesium carbonate. A suitable palladium source can be, for example, palladium acetate or palladium chloride. Preferably the reaction is carried out with cesium carbonate, palladium acetate, and Xantphos in toluene and heated to, preferably, a temperature between about 80° C. and about 110° C. to complete the reaction to provide a compound of formula (IIIc). The resulting mixture can be cooled to between about 15° C. and about 40° C. and diluted with a halogenated hydrocarbon, followed by filtering the mixture, and then concentrating the mixture to provide an isolated compound of general formula (IIIc). The compounds of (IIIa), (IIIb), and (IIIc) have the structures:

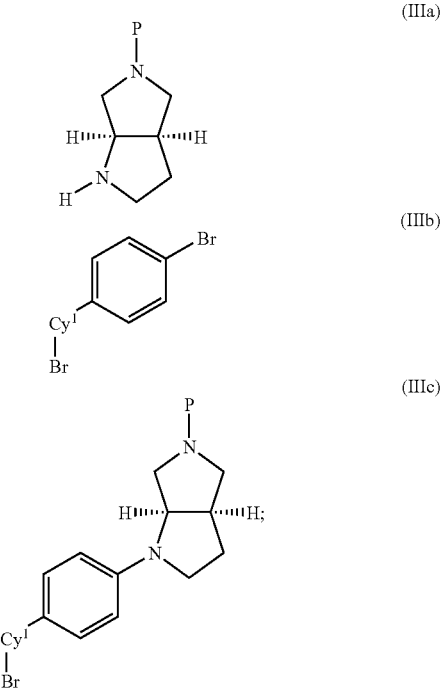

wherein $Cy^1$ is aryl, and preferably is phenyl, and P is a nitrogen-protecting group. Heating compounds of formula (IIIc) with the compound of formula (IIId), a carbonate base and a copper source in a high-boiling polar solvent produces compounds of formula (IIIe). Preferably, the carbonate base is potassium carbonate. The copper source can be copper powder or copper (I) iodide. The preferred reaction is carried out by heating a compound of formula (IIIc) and a compound of formula (IIId) with copper (I) iodide, 8-hydroxyquinoline and potassium carbonate in N,N-dimethylformamide to about 120° C. to about 150° C. under an inert atmosphere. The compounds can be isolated by cooling the mixture to between about 15° C. and about 40° C., partitioning the mixture between and organic solvent and a sodium chloride solution, and then concentrating the organic solution provides compounds of formula (IIIe), as shown below.

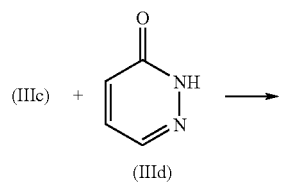

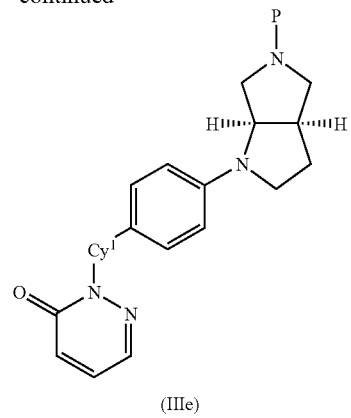

Removing the nitrogen protecting group of the compound of formula (IIIe) provides compounds of formula (III), wherein preferably $Cy^1$ is p-phenyl. Preferably the nitrogen-protecting group P of (IIIe) is ethoxycarbonyl, methoxycarbonyl, or tert-butyloxycarbonyl. The preferred nitrogen-protecting group is ethoxycarbonyl. Commonly used nitrogen-protecting groups as well as methods to remove them are disclosed in T. W. Greene and P. G. M. Wuts, Protective Groups in Organic Synthesis, 3rd edition, John Wiley & Sons, New York (1999). Preferred methods of removing nitrogen-protecting groups include the treatment with hydrogen bromide in acetic acid or, alternatively, treatment with a base in the presence of ethylene glycol.

The invention also provides pharmaceutical compositions comprising a therapeutically effective amount of a compound of formula (I) or (II), or suitable salts and polymorphs thereof, in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyimide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts, esters, or amides derived from inorganic or organic acids. The term "pharmaceutically acceptable salts, esters and amides", as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid or inorganic acid.

Representative acid addition salts include, but are not limited to ascorbic acid, (D)-tartaric acid, (L)-tartaric acid, phosphoric acid, salicylic acid, sulfuric acid, trifluoroacetic acid, and hydrochloric acid.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide", as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug", as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I) or formula (II).

Salts and Polymorphs

Particular salts and polymorphs of compounds of the invention also have been identified and are described herein. More particularly, the invention relates to 2-{4'-[(3aR,6aR)-5-methylhexahydropyrrolo[3,4-b]pyrrol-1(2H)-yl]-1,1'-biphenyl-4-yl}pyridazin-3(2H)-one ascorbate, (D)-tartrate, (L)-tartrate, phosphate, salicylate, sulfate, hydrochloride, and trifluoroacetate salts. Particular polymorphs of the L-tartrate salt and hydrochloride salt also are described herein.

More particularly, the invention relates to crystalline 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate salt monohydrate. The salt exhibits at least two polymorphs, designated as 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form A and 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form B.

2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate monohydrate Form A (also referred to herein as "Form A") exists as a crystalline solid characterized by the powder X-ray diffraction pattern shown in FIG. 1. The crystallographic unit cell parameters of 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form A have been determined as: a is 7.6 Å, b is 7.4 Å, c is 22.7 Å, or more precisely where a is 7.588(3) Å, b is 7.428(3) Å$^3$, c is 22.700 (7) Å, to afford a cell volume of 1276 Å$^3$, or more precisely 1276.3(7) Å$^3$, wherein a, b, and c are each a representative length of the crystal lattice and the unit cell angle β is 94.1°, or more precisely 94.093(5)°. The salt crystallizes in the monoclinic P2$_1$ space group.

2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate monohydrate Form A crystalline solid can be identified by characteristic peaks in its powder X-ray diffraction pattern. One with skill in the art of analytical chemistry would be able to readily identify the 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form A solid by as few as one characteristic peak in its powder X-ray diffraction pattern. Two-theta angle positions of characteristic peaks in a powder X-ray diffraction pattern of 2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate monohydrate Form A are 3.90±0.2, 16.72±0.2, 16.99±0.2, 17.17±0.2, 18.12±0.2, 19.72±0.2, 19.98±0.2, 20.25±0.2, 23.96±0.2, 27.65±0.2, and 28.93±0.2.

Figure 2:
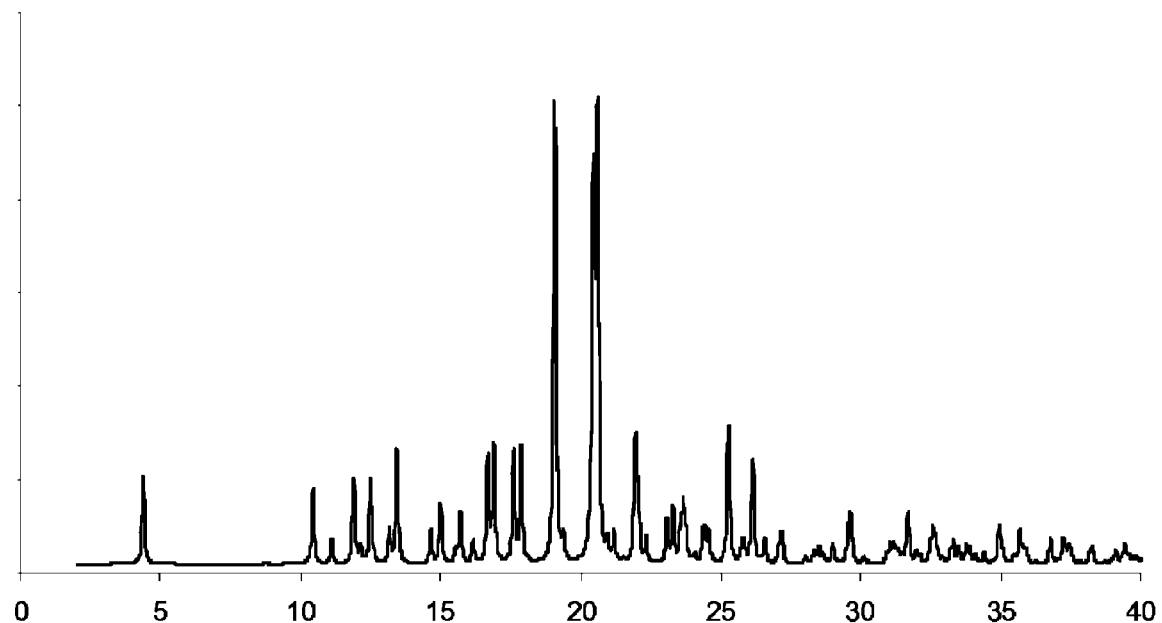
FIG. 2 is a powder X-ray diffraction pattern of a L-tartrate monohydrate Form B polymorph of 2-{4'-[(3aR,6aR)-5-methylhexahydropyrrolo[3,4-b]pyrrol-1(2H)-yl]-1,1'-biphenyl-4-yl}pyridazin-3(2H)-one.

2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate monohydrate Form B (also referred to herein as "Form B") exists as a crystalline solid characterized by the powder X-ray diffraction pattern shown in FIG. 2. The crystallographic unit cell parameters of 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form B have been determined as: a is 7.6 Å, b is 8.7 Å, c is 40.3 Å, or more precisely where a is 7.551(5) Å, b is 8.660(6) Å, c is 40.26(3) Å, to afford a cell volume of 2633(3) Å$^3$, wherein a, b, and c are each a representative length of the crystal lattice. The salt crystallizes in the orthorhombic P2$_1$2$_1$2$_1$ space group.

2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate monohydrate Form B crystalline solid can be identified by characteristic peaks in its powder X-ray diffraction pattern. One with skill in the art of analytical chemistry would be able to readily identify the 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form B solid by as few as one characteristic peak in its powder X-ray diffraction pattern. Two-theta angle positions of characteristic peaks in a powder X-ray diffraction pattern of 2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate monohydrate Form B are 4.39±0.2, 10.45±0.2, 11.92±0.2, 12.52±0.2, 13.45±0.2, 16.71±0.2, 16.92±0.2, 17.62±0.2, 17.90±0.2, 19.10±0.2, 20.46±0.2, and 20.63±0.2.

Figure 3:
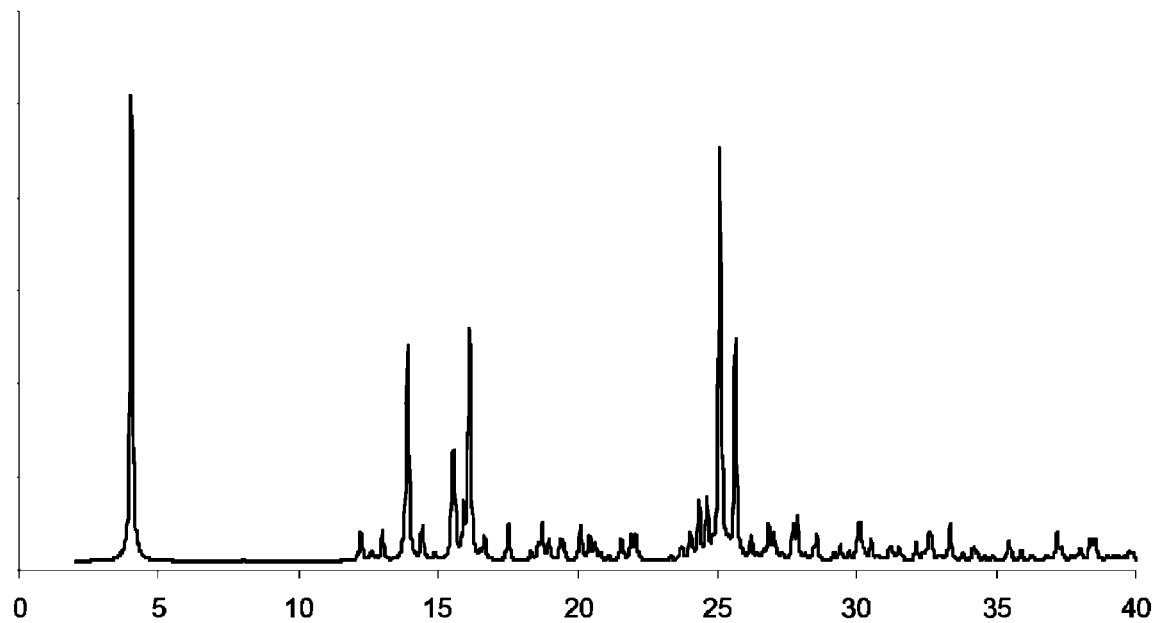
FIG. 3 is a powder X-ray diffraction pattern of a hydrochloride trihemihydrate polymorph of 2-{4'-[(3aR,6aR)-5-methylhexahydropyrrolo[3,4-b]pyrrol-1(2H)-yl]-1,1'-biphenyl-4-yl}pyridazin-3(2H)-one.

The invention also relates to crystalline 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride trihemihydrate. 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride trihemihydrate exists as a crystalline solid characterized by the powder X-ray diffraction pattern shown in FIG. 3. The crystallographic unit cell parameters of 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride trihemihydrate have been determined as: a is 7.3 Å, b is 7.4 Å, and c is 22.2 Å, or more precisely where a is 7.287(2) Å, b is 7.405(2) Å, and c is 22.234(5) Å to afford a cell volume of 1155 Å$^3$, or more precisely 1155.4(4) Å$^3$, wherein a, b, and c are each a representative length of the crystal lattice and the unit cell angles α, β, and γ are each respectively 86.3°, 81.0°, and 77.3°, or more precisely 86.258(4)°, 80.957(4)°, and 77.330(4)°. The salt crystallizes in the triclinic P1 space group.

2-{4'-[(3aR,6aR)-5-Methylhexahydropyrrolo[3,4-b]pyrrol-1(2H)-yl]-1,1'-biphenyl-4-yl}pyridazin-3(2H)-one hydrochloride trihemihydrate crystalline solid can be identified by characteristic peaks in its powder X-ray diffraction pattern. One with skill in the art of analytical chemistry would be able to readily identify the 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride trihemihydrate solid by as few as one characteristic peak in its powder X-ray diffraction pattern. Two-theta angle positions of characteristic peaks in a powder X-ray diffraction pattern of 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride trihemihydrate are 4.03±0.2, 13.92±0.2, 15.55±0.2, 15.61±0.2, 15.93±0.2, 16.15±0.2, 24.37±0.2, 24.66±0.2, 25.12±0.2, 25.68±0.2, and 27.90±0.2.

Figure 4:
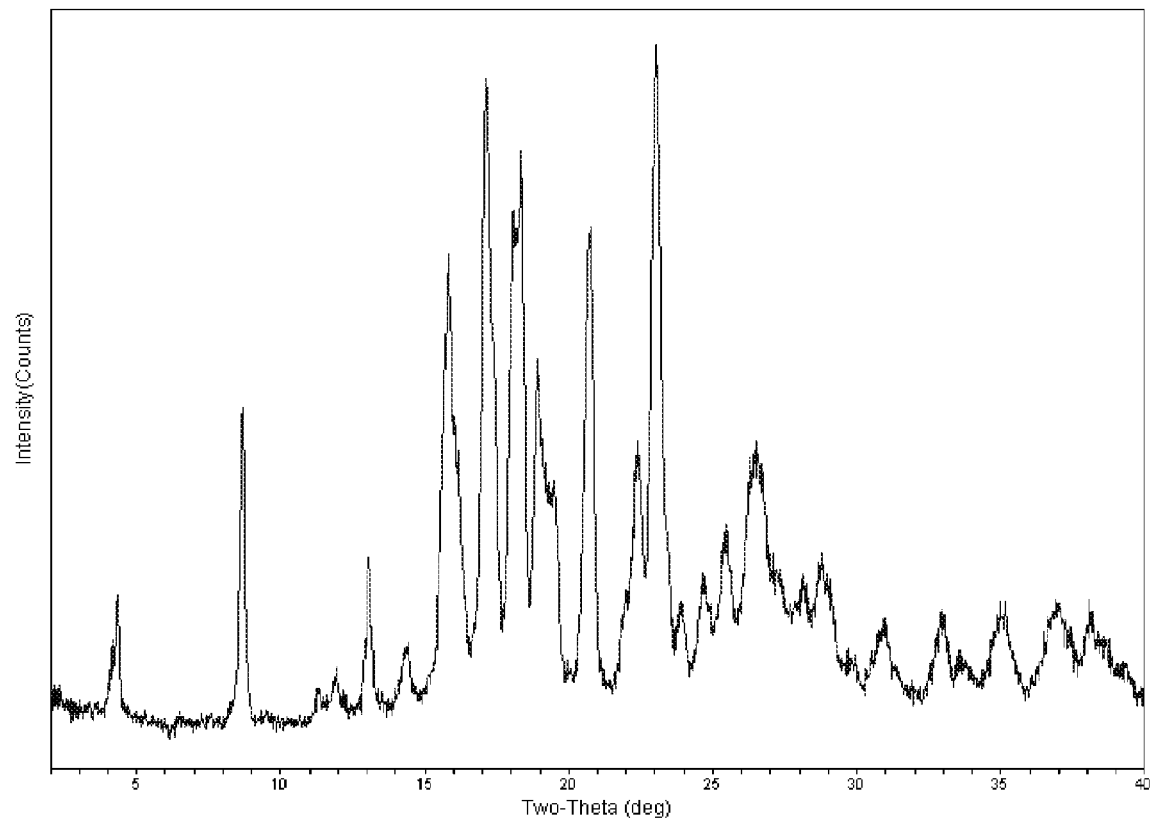
FIG. 4 is a powder X-ray diffraction pattern of an anhydrous tartrate polymorph of 2-{4'-[(3aR,6aR)-5-methylhexahydropyrrolo[3,4-b]pyrrol-1(2H)-yl]-1,1'-biphenyl-4-yl}pyridazin-3(2H)-one.

The invention also relates to crystalline 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate anhydrate. 2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate anhydrate exists as a crystalline solid characterized by the powder X-ray diffraction pattern shown in FIG. 4. 2-{4'-[(3aR,6aR)-5-Methylhexahydropyrrolo[3,4-b]pyrrol-1(2H)-yl]-1,1'-biphenyl-4-yl}pyridazin-3(2H)-one tartrate anhydrate crystalline solid can be identified by characteristic peaks in its powder X-ray diffraction pattern. One with skill in the art of analytical chemistry would be able to readily identify the 2-{4'-[(3aR,6aR)-5-methylhexahydropyrrolo[3,4-b]pyrrol-1(2H)-yl]-1,1'-biphenyl-4-yl}pyridazin-3(2H)-one tartrate anhydrate solid by as few as one characteristic peak in its powder X-ray diffraction pattern. Two-theta angle positions of characteristic peaks in a powder X-ray diffraction pattern of 2-{4'-[(3aR,6aR)-5-methylhexahydropyrrolo[3,4-b]pyrrol-1(2H)-yl]-1,1'-biphenyl-4-yl}pyridazin-3(2H)-one tartrate anhydrate are 4.34±0.2, 8.69±0.2, 13.04±0.2, 15.82±0.2, 17.11±0.2, 18.35±0.2, 18.93±0.2, 20.74±0.2, 22.40±0.2, 23.04±0.2, and 26.45±0.2.

Figure 5:
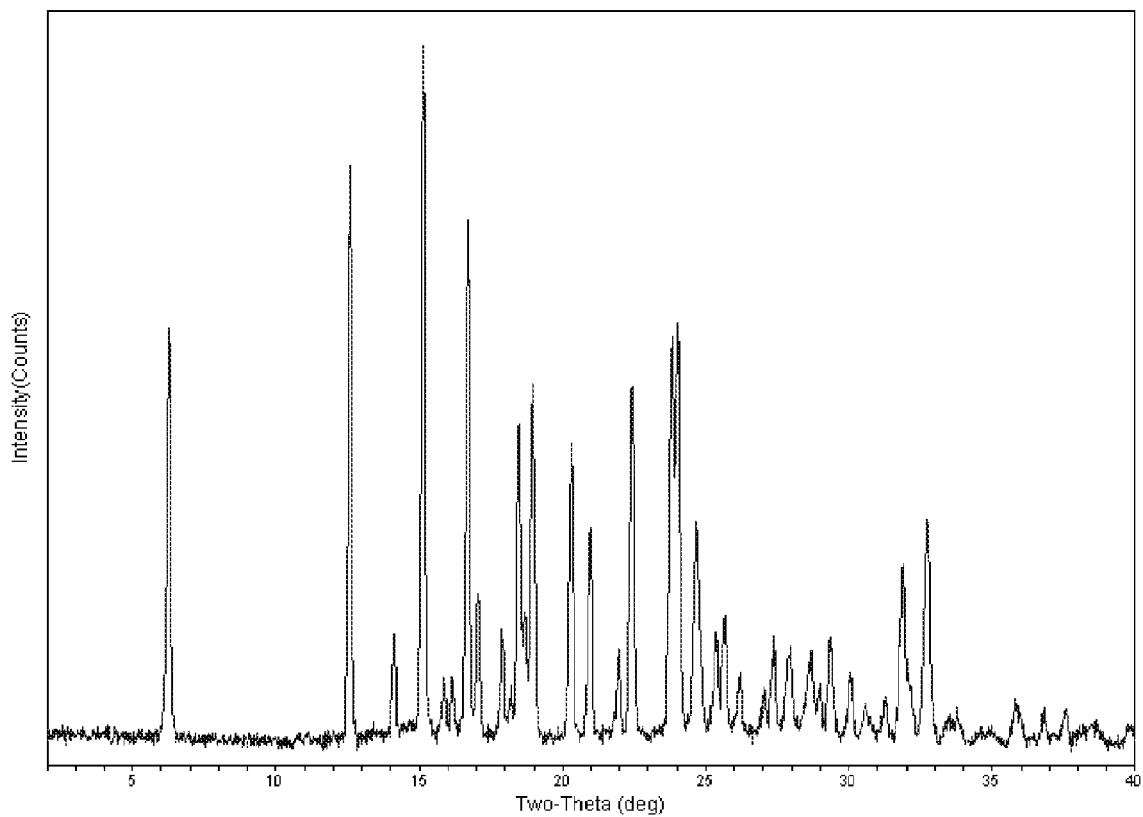
FIG. 5 is a powder X-ray diffraction pattern of an anhydrous hydrochloride polymorph of 2-{4'-[(3aR,6aR)-5-methylhexahydropyrrolo[3,4-b]pyrrol-1(2H)-yl]-1,1'-biphenyl-4-yl}pyridazin-3(2H)-one.

The invention also relates to crystalline 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride anhydrate. 2-{4'-[(3aR,6aR)-5-Methylhexahydropyrrolo[3,4-b]pyrrol-1(2H)-yl]-1,1'-biphenyl-4-yl}pyridazin-3(2H)-one hydrochloride anhydrate exists as a crystalline solid characterized by the powder X-ray diffraction pattern shown in FIG. 5. 2-{4'-[(3aR,6aR)-5-Methylhexahydropyrrolo[3,4-b]pyrrol-1(2H)-yl]-1,1'-biphenyl-4-yl}pyridazin-3(2H)-one hydrochloride anhydrate crystalline solid can be identified by characteristic peaks in its powder X-ray diffraction pattern. One with skill in the art of analytical chemistry would be able to readily identify the 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride anhydrate solid by as few as one characteristic peak in its powder X-ray diffraction pattern. Two-theta angle positions of characteristic peaks in a powder X-ray diffraction pattern of 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride anhydrate are 6.27±0.2, 12.59±0.2, 15.15±0.2, 16.71±0.2, 18.49±0.2, 18.95±0.2, 20.31±0.2, 20.97±0.2, 22.44±0.2, 23.82±0.2, 24.03±0.2, 24.67±0.2, 31.90±0.2, and 32.75±0.2.

The L-tartrate monohydrate Form A salt and L-tartrate monohydrate Form B salt generally demonstrate better relative oxidative stability than the 2-{4'-[(3aR,6aR)-5-methylhexahydropyrrolo[3,4-b]pyrrol-1(2H)-yl]-1,1'-biphenyl-4-yl}pyridazin-3(2H)-one compound. Accordingly, a L-tartrate monohydrate Form A or L-tartrate monohydrate Form B salt may be preferred for formulation and more suitable for administration.

As used herein the term "substantially pure", when used in reference to a salt of 2-{4'-[(3aR,6aR)-5-methylhexahydropyrrolo[3,4-b]pyrrol-1(2H)-yl]-1,1'-biphenyl-4-yl}pyridazin-3(2H)-one, refers to a salt that is greater than about 90% pure. The crystalline form of 2-{4'-[(3aR,6aR)-5-methylhexahydropyrrolo[3,4-b]pyrrol-1(2H)-yl]-1,1'-biphenyl-4-yl}pyridazin-3(2H)-one does not contain more than about 10% of any other compound and, in particular, does not contain more than about 10% of any other form of 2-{4'-[(3aR,6aR)-5-methylhexahydropyrrolo[3,4-b]pyrrol-1(2H)-yl]-1,1'-biphenyl-4-yl}pyridazin-3(2H)-one, such as amorphous, solvated forms, non-solvated forms, desolvated forms, and the enantiomer.

More preferably, a "substantially pure" salt refers to a salt that is greater than about 95% pure, wherein the crystalline form of 2-{4'-[(3aR,6aR)-5-methylhexahydropyrrolo[3,4-b]pyrrol-1(2H)-yl]-1,1'-biphenyl-4-yl}pyridazin-3(2H)-one does not contain more than about 5% of any other compound and, in particular, does not contain more than about 5% of any other form of 2-{4'-[(3aR,6aR)-5-methylhexahydropyrrolo[3,4-b]pyrrol-1(2H)-yl]-1,1'-biphenyl-4-yl}pyridazin-3(2H)-one, such as amorphous, solvated forms, non-solvated forms, desolvated forms, and the enantiomer.

Even more preferably, a "substantially pure" salt refers to a salt that is greater than about 97% pure; wherein the crystalline form of 2-{4'-[(3aR,6aR)-5-methylhexahydropyrrolo[3,4-b]pyrrol-1(2H)-yl]-1,1'-biphenyl-4-yl}pyridazin-3(2H)-one does not contain more than about 3% of any other compound and, in particular, does not contain more than about 3% of any other form of 2-{4'-[(3aR,6aR)-5-methylhexahydropyrrolo[3,4-b]pyrrol-1(2H)-yl]-1,1'-biphenyl-4-yl}pyridazin-3(2H)-one, such as amorphous, solvated forms, non-solvated forms, desolvated forms, and the enantiomer.

Compositions comprising 2-{4'-[(3aR,6aR)-5-methylhexahydropyrrolo[3,4-b]pyrrol-1(2H)-yl]-1,1'-biphenyl-4-yl}pyridazin-3(2H)-one salts and polymorphs also are contemplated. A suitable pharmaceutical composition comprises a substantially pure 2-{4'-[(3aR,6aR)-5-methylhexahydropyrrolo[3,4-b]pyrrol-1(2H)-yl]-1,1'-biphenyl-4-yl}pyridazin-3(2H)-one salt or polymorph formulated together with one or more non-toxic pharmaceutically acceptable carriers as previously described for the compositions. Such compositions comprising 2-{4'-[(3aR,6aR)-5-methylhexahydropyrrolo[3,4-b]pyrrol-1(2H)-yl]-1,1'-biphenyl-4-yl}pyridazin-3(2H)-one salts and polymorphs are administered and can be used in the methods of the invention as previously described for the compounds of the invention, except substituting a desired salt or polymorph in place of a compound, which would readily understood by one with skill in the art.

Powder X-ray diffraction (PXRD) analysis of samples was conducted in the following manner. Samples for X-ray diffraction analysis were prepared by spreading the sample in a thin layer on the sample holder and gently flattening the sample with a microscope slide. For example, the sample may have been ground to a fine powder with mortar and pestle, or with glass microscope slides for limited quantity samples. Samples were run in one of three configurations: circular bulk holder, a quartz zero background plate, or hot stage mount (similar mounting to a zero background plate).

Diffraction patterns were collected using an Inel G3000 difractometer equipped with an incident beam germanium monochromator to provide Cu—K$_{\alpha 1}$ radiation. The X-ray generator was operated at a voltage of 40 kV and a current of 30 mA. The Inel G3000 is equipped with a position sensitive detector that monitors all diffraction data simultaneously. The detector was calibrated by collecting the attenuated direct beam for seven seconds in 1 degree intervals across a 90 degree two theta range. The calibration was checked against a silicon line position reference standard (NIST 640c). Samples were placed on an aluminum sample holder and leveled with a glass slide.

Alternatively, X-ray powder diffraction can be performed using a Rigaku Miniflex diffractometer (30 kV and 15 mA;

X-ray source: Cu; Range: 2.00-40.00° Two Theta; Scan rate: 1-5 degree/minute) or a Scintag X1 or X2 diffractometer (2 kW normal focus X-ray tube with either a liquid nitrogen or Peltier cooled germanium solid state detector; 45 kV and 40 mA; X-ray source: Cu; Range: 2.00-40.00° Two Theta; Scan Rate: 1-5 degree/minute).

Characteristic powder X-ray diffraction pattern peak positions are reported in terms of angular positions (two theta) with an allowable variability of ±0.2°. The variability of ±0.1° is intended to be used when comparing two powder X-ray diffraction patterns. In practice, if a diffraction pattern peak from one pattern is assigned a range of angular positions (two theta) which is the measured peak position ±0.2° and a diffraction pattern peak from another pattern is assigned a range of angular positions (two theta) which is measured peak position ±0.2° and if those ranges of peak position overlap, then the two peaks are considered to have the same angular position (two theta). For example, if a diffraction pattern peak from one pattern is determined to have a peak position of 5.20° for comparison purposes the allowable variability allows the peak to be assigned a position in the range of 5.00°-5.40°. If a comparison peak from the other diffraction pattern is determined to have a peak position of 5.35° and the allowable variability allows the peak to be assigned a position in the range of 5.15°-5.55°, then the two peaks being compared are considered to have the same angular position (two theta) because there is overlap between the two ranges of peak positions.

Single crystal X-ray diffraction analysis of samples was conducted in the following manner. Samples for X-ray diffraction analysis were prepared by affixing selected single crystals to glass pins with epoxy adhesive. X-ray diffraction data was collected using a Bruker SMART system with an APEX area detector (50 kv and 40 mA; X-ray source: Mo). Data were collected at −90° C.

Radiolabelled Compound Use

Compounds and compositions of the invention also are useful as diagnostic tools. The ability of PET (positron emitting tomography) and sPECT to probe the degree of receptor occupancy in humans and animals by endogenous ligands (such as histamine for the histamine $H_3$ receptor) or drugs (such with a clinically used drug that affects brain histamine levels) is widely recognized. This constitutes the use of PET as a biomarker to assess efficacy of pharmacological interventions with drugs. The topic and use of positron-emitting ligands for these purposes has been generally reviewed, for example in "PET ligands for assessing receptor occupancy in vivo" Burns, et al. Annual Reports in Medicinal Chemistry (2001), 36, 267-276; "Ligand-receptor interactions as studied by PET: implications for drug development" by Jarmo Hietala, Annals of Medicine (Helsinki) (1999), 31(6), 438-443; "Positron emission tomography neuroreceptor imaging as a tool in drug discovery, research and development" Burns, et al. Current Opinion in Chemical Biology (1999), 3(4), 388-394. The compounds of the invention, synthesized with $^{11}C$, $^{18}F$, or other positron-emitting isotopes are suitable ligand tools for PET; a number of positron-emitting reagents have been synthesized, are available, and are known to those skilled in the art. Especially suitable compounds of the invention for this use are those wherein a $^{11}CH_3$ group can be incorporated in by reaction with $^{11}CH_3I$. Also, especially suitable compounds of the use are those wherein a $^{18}F$ group can be incorporated into the compound by reaction with $^{18}F$-fluoride anion. The incorporation of $^{11}CH_3I$ can be carried out according to a method known to those skilled in the art. According to one method, compounds of formula (I), wherein $R^1$ is hydrogen can be treated with base and $^{11}CH_3I$ to prepare ligands for use in PET studies. For incorporation of $^{18}F$ into compounds or compositions of the invention, compounds of formula (I), wherein $R^1$ is 1-hydroxyethyl, can be treated with methanesulfonic anhydride or triflic anhydride and a base in an inert solvent such as dichloromethane, and the resulting compound (a methanesulfonate or triflate) can be treated with $^{18}F$-fluoride by methods well known to skilled in the art of synthetic organic chemistry or medicinal chemistry.

REFERENCE EXAMPLE

The following Reference Example describes synthesis of a compounds used for preparation of compounds as described in the Examples. Such methods are intended only to provide examples of how such compounds can be obtained and are not intended to provide an exhaustive list of how to provide the desired compound.

Reference Example A

Ethyl(3aR,6aR)-hexahydropyrrolo[2,3-c]pyrrole-5 (1H)-carboxylate dibenzoyl-D-tartrate salt Example A1

((R)-1-Phenyl-ethylamino)-acetic acid methyl ester

A reactor was charged with 10 g of R-methylbenzylamine, 100 mL of EtOAc, and 9.19 g of $Et_3N$. Methyl bromoacetate (15.15 g) was added and the mixture was heated to 50-60° C. for 10 hours with stirring. The mixture was then cooled to ambient temperature, then washed with 50 mL of water followed by 50 mL of 15% NaCl solution, to provide 100 g of an ethyl acetate solution which contained 15 grams of (1-phenyl-ethylamino)-acetic acid methyl ester (96% yield).

Example A2

(1-(R)-Phenyl-ethylamino)-acetic acid

A solution of (1-(R)-phenyl-ethylamino)-acetic acid methyl ester (21.7 g of a solution in EtOAc) was concentrated, and the residue was taken up in 24 mL of water and heated at reflux for 13 hours. Upon completion, the mixture was concentrated under reduced pressure and 30 mL of isopropanol was added. The resulting precipitate was filtered and rinsed with 10 mL of isopropanol then dried under reduced pressure to provide 2.4 g of the title compound.

Example A3

Ethyl 1-(R)-1-phenylethyl)hexahydropyrrolo[2,3-c] pyrrole-5(1H)-carboxylate

A solution of (1-(R)-phenyl-ethylamino)-acetic acid (25.6 g) in 384 mL of toluene was heated to 90° C. To this 170 g (1.1 equivalents) of a 15.84 wt. % solution of allyl-(2-oxo-ethyl)-carbamic acid ethyl ester (U.S. Pat. No. 5,071,999) in toluene, was added over 20 minutes and the mixture was stirred at 90° C. for 14 hours then at 95° C. for 12 hours. After cooling, the product was extracted with 2×115 g of 20% citric acid solution. The citric acid solution was diluted with 205 mL of isopropyl acetate, and the mixture was neutralized with a solution of 51.2 g $K_2CO_3$ in 120 g water, and thoroughly shaken. The layers were separated, and the aqueous layer was extracted again with 102 mL of isopropyl acetate. The organic extracts were combined and distilled under reduced pressure to provide an oil which was then diluted with 125 mL of methanol to provide 140 g (100% yield) of the title compound as a 30% by weight solution in methanol.

Example A4

Ethyl hexahydropyrrolo[3,4-b]pyrrole-5(1H)-carboxylate

5% Palladium hydroxide on activated carbon (13.9 g, 50% w/w in water) was added to a pressure reactor. The product of Example A3 (as 506.8 g of a 25.9 wt % solution of ethyl 1-((R)-1-phenylethyl)hexahydropyrrolo[2,3-c]pyrrole-5 (1H)-carboxylate (131.3 g) in MeOH) was added, followed by a methanol rinse (37 g). The mixture was heated to 50° C. under an atmosphere of hydrogen (40 psi) for 4 hours. The mixture was filtered through Hyflo® Filter Aid and rinsed with 200 mL of MeOH to provide a solution containing 78.9 g of the title compound.

Example A5

Ethyl(3aR,6aR)-hexahydropyrrolo[2,3-c]pyrrole-5 (1H)-carboxylate dibenzoyl-D-tartrate salt A solution of 150 g of ethyl hexahydropyrrolo[3,4-b]pyrrole-5(1H)-carboxylate (~11.2% wt in MeOH) was heated to 60° C. To this was added a solution of D-dibenzoyltartaric acid mono-hydrate (231.5 g) dissolved in MeOH (591 mL+95 mL rinse), and the mixture was stirred at 60±5° C. for 2 hours during which time crystallization occurred. The slurry was cooled to 18° C. over 6 hours, and the product was collected by filtration and rinsed with MeOH (2×330 mL). The product was dried at 40-45° C. to provide 198 g of the title compound. Chiral HPLC analysis of the Cbz-derivative of the product indicated that the product was obtained with 99% ee.

EXAMPLES

The compounds and processes of the invention will be better understood by reference to the following examples, which are intended as an illustration of and not a limitation upon the scope of the invention.

Unless otherwise described, reactions were carried out under ambient conditions (ranging 17-27° C.), under nitrogen. Unless otherwise described, column chromatography means flash chromatography carried out using silica gel, a technique well known to those of ordinary skill in the art of organic synthesis.

Example 1

(3aR,6aR)-4'-(5-Ethyl-hexahydro-pyrrolo[3,4-b] pyrrol-1-yl)-biphenyl-4-carbonitrile

Example 1A (3aR,6aR)-Hexahydro-pyrrolo[3,4-b]pyrrole-1,5-dicarboxylic acid 5-benzyl ester 1-tert-butyl ester (3aR,6aR)-Hexahydro-pyrrolo[3,4-b]pyrrole-1-carboxylic acid tert-butyl ester (3.0 g, 12.5 mmole) and N-(benzyloxycarbonyloxy)-succinimide (3.42 g, 13.7 mmole) were mixed in 15 ml of dichloromethane. The mixture was stirred at room temperature overnight and then concentrated under vacuum to provide the crude product. The residue was purified by flash chromatography (20% ethyl acetate in hexane) to provide the title compound. $^1$H NMR (CDCl$_3$) δ ppm 7.29-7.43 (m, 5H) 5.13 (s, 2H) 4.15-4.33 (m, 1H) 3.39-3.74 (m, 5H) 3.20-3.37 (m, 1H) 2.84-2.96 (m, 1H) 1.92-2.03 (m, 1H) 1.66-1.82 (m, 1H) 1.46 (s, 9H). MS: (M+H)$^+$=347.

The starting material (3aR,6aR)-hexahydro-pyrrolo[3,4-b] pyrrole-1-carboxylic acid tert-butyl ester (CAS #370880-09-4) may be prepared as described in the literature, for example the method of Schenke, et al., "Preparation of 2,7-Diazabicyclo[3.3.0]octanes" U.S. Pat. No. 5,071,999 (1991) which provides a racemate which may be resolved by chromatography on a chiral column or by fractional crystallization of diasteromeric salts, or as described in Basha, et al. "Substituted diazabicycloalkane derivatives", US 2005101602 (2005).

Example 1B (3aR,6aR)-Hexahydro-pyrrolo[3,4-b]pyrrole-5-carboxylic acid benzyl ester The product of Example 1A ((3aR,6aR)-hexahydro-pyrrolo[3,4-b]pyrrole-1,5-dicarboxylic acid 5-benzyl ester 1-tert-butyl ester) (4.5 g, 12.5 mmole), was stirred with a mixture of dichloromethane and trifluoroacetic acid (15 ml/15 ml) for 2 hours. The solvent was removed under reduced pressure, and the residue was basified with saturated sodium bicarbonate, then extracted with dichloromethane (3×). The combined organic layers were washed with brine, dried over sodium sulfate, filtered, and concentrated under reduced pressure. The residue was purified by column chromatography (0.6% ammonium hydroxide and 6% methanol in dichloromethane) to provide the title compound. $^1$H NMR (CDCl$_3$) δ ppm 7.28-7.40 (m, 5H) 5.12 (s, 2H) 3.74-3.87 (m, 1H) 3.53-3.71 (m, 2H) 3.36-3.48 (m, 1H) 3.18-3.32 (m, 1H) 3.01-3.13 (m, 1H) 2.88-3.01 (m, 1H) 2.70-2.83 (m, 1H) 1.87-2.03 (m, 1H) 1.58-1.76 (m, 1H). MS: (M+H)$^+$=247.

Example 1C

Trifluoro-methanesulfonic acid 4'-cyano-biphenyl-4-yl ester

Commercially available 4-cyano-4'-hydroxybiphenyl was dissolved in dichloromethane. Triethylamine (2.5 equiv.) was added and the mixture was stirred at room temperature. Triflic anhydride (1.3 equiv) was added slowly, and the resulting solution was stirred for 2 hours. The mixture was diluted with saturated aqueous sodium bicarbonate and extracted with dichloromethane. The organic layer was washed with brine, dried over sodium sulfate, filtered, and concentrated under reduced pressure. The residue was purified by column chromatography to provide the title compound. $^1$H NMR (CDCl$_3$) δ ppm 7.76 (d, J=8.82 Hz, 2H) 7.66 (d, J=8.82 Hz, 4H) 7.40 (d, J=8.82 Hz, 2H). MS: (M+H)$^+$=328.

Example 1D (3aR,6aR)-1-(4'-Cyano-biphenyl-4-yl)-hexahydropyrrolo[3,4-b]pyrrole-5-carboxylic acid benzyl ester The product of Example 1B (trifluoro-methanesulfonic acid 4'-cyano-biphenyl-4-yl ester) (135 mg, 0.55 mmole), the product of Example 1C (198 mg, 0.61 mmole), palladium acetate (2.7 mg, 0.012 mmole), racemic-2,2'-bis(diphenylphosphino)-1,1'-binaphthyl (BINAP, 20 mg, 0.033 mmole) and sodium tert-butoxide (80 mg, 0.83 mmole) were mixed in 1.5 ml of toluene and heated at 80° C. under N$_2$ for 16 hours. The mixture was cooled to room temperature, diluted with water and extracted with dichloromethane (3×). The combined organics were dried over sodium sulfate and concentrated to provide the crude product, which was purified by chromatography (5% methanol in dichloromethane) to provide the title compound. MS: (M+H)⁺=424.

Example 1E (3aR,6aR)-4'-(Hexahydro-pyrrolo[3,4-b]pyrrol-1-yl)-biphenyl-4-carbonitrile The product of Example 1D ((3aR,6aR)-1-(4'-Cyano-biphenyl-4-yl)-hexahydro-pyrrolo[3,4-b]pyrrole-5-carboxylic acid benzyl ester) (750 mg, 1.77 mmole) was refluxed in 10 ml trifluoroacetic acid for 2.5 hours. The solution was concentrated and triturated with dichloromethane. The residue was redissolved in dichloromethane and stirred with sodium bicarbonate powder. The solution was loaded on a silica gel column and purified by chromatography (0.6% ammonium hydroxide and 6% methanol in dichloromethane) to provide the title compound (330 mg, 64%). $^1$H NMR (CDCl$_3$) δ ppm 7.64 (d, J=2.71 Hz, 4H) 7.51 (d, J=8.81 Hz, 2H) 6.66 (d, J=8.82 Hz, 2H) 4.07-4.17 (m, 1H) 3.50-3.65 (m, 1H) 3.24-3.36 (m, 1H) 2.86-3.10 (m, 5H) 2.15-2.29 (m, 1H) 1.74-1.93 (m, 1H). MS: (M+H)⁺=290.

Example 1F (3aR,6aR)-4'-(5-Ethyl-hexahydro-pyrrolo[3,4-b]pyrrol-1-yl)-biphenyl-4-carbonitrile The product of Example 1E (22 mg, 0.076 mmole) was dissolved in 2.5 ml anhydrous THF under nitrogen. Sodium hydride (95%, 4 mg, 0.167 mmole) was added and the mixture was stirred at room temperature for 1 hour. Iodoethane (18 µl, 0.225 mmole) was added and the mixture was stirred at room temperature over night. The mixture was diluted with water and extracted with dichloromethane (3×). The combined organic layers were washed with brine, dried over sodium sulfate, filtered, and concentrated under reduced pressure. The resulting residue was purified by column chromatography (eluting with a mixture of 0.2% ammonium hydroxide and 2% methanol in dichloromethane) to provide the title compound (11 mg, 46%). $^1$H NMR (CDCl$_3$) δ ppm 7.64 (d, J=1.36 Hz, 4H) 7.50 (d, J=8.82 Hz, 2H) 6.65 (d, J=8.82 Hz, 2H) 4.14-4.23 (m, 1H) 3.47-3.60 (m, 1H) 3.27-3.39 (m, 1H) 2.92-3.04 (m, 1H) 2.70-2.81 (m, 1H) 2.38-2.67 (m, 5H) 2.11-2.25 (m, 1H) 1.89-2.03 (m, 1H) 1.08 (t, J=7.12 Hz, 3H); MS (M+H)⁺=318.

Example 2

4'-[(3aR,6aR)-5-isopropylhexahydropyrrolo[3,4-b]pyrrol-1(2H)-yl]-1,1'-biphenyl-4-carbonitrile To a solution of the product of Example 1E (26 mg, 0.09 mmole) in methanol (2 ml) was added acetone (132 µl, 1.8 mmole), and the mixture was stirred at room temperature for 1.5 hour. Sodium cyanoborohydride (28 mg, 0.44 mmole) was added and the mixture stirred overnight. The mixture was diluted with 2 ml 1N NaOH and extracted with dichloromethane (with 5% methanol) (3×). The combined organic layers were washed with brine, dried over sodium sulfate, filtered, and concentrated under reduced pressure. The residue was purified by column chromatography (eluting with a mixture of 0.35% ammonium hydroxide and 3.5% methanol in dichloromethane) to provide the title compound. $^1$H NMR (CDCl$_3$) δ ppm 7.63 (d, J=3.74 Hz, 4H) 7.50 (d, J=9.05 Hz, 2H) 6.64 (d, J=8.73 Hz, 2H) 4.16-4.22 (m, 1H) 3.48-3.55 (m, 1H) 3.31-3.38 (m, 1H) 2.90-3.01 (m, 2H) 2.74 (t, J=7.96 Hz, 1H) 2.46-2.52 (m, 2H) 2.31-2.39 (m, 1H) 2.10-2.20 (m, 1H) 1.90-1.99 (m, 1H) 1.06 (dd, J=6.24, 1.87 Hz, 6H); MS (M+H)⁺=332.

The following compounds and Examples were made according to the procedures described above with the exception that different reagents were substituted to obtain the titled compounds.

TABLE 1

Examples 3-6

| Example | Starting Material | Reaction procedure | Resulting compound | NMR and MS |
| --- | --- | --- | --- | --- |
| Example 3 | Product of Example 1E and iodopropane | Example 1F | 4'-[(3aR,6aR)-5-propylhexahydropyrrolo[3,4-b]pyrrol-1(2H)-yl]-1,1'-biphenyl-4-carbonitrile | $^1$H NMR (CDCl$_3$) δ ppm 7.64 (d, J = 1.70 Hz, 4 H), 7.50 (d, J = 8.82 Hz, 2 H), 6.64 (d, J = 8.82 Hz, 2 H), 4.12-4.22 (m, 1 H), 3.46-3.57 (m, 1 H), 3.27-3.39 (m, 1 H), 2.88-3.02 (m, 1 H), 2.61-2.74 (m, 2 H), 2.49-2.58 (m, 2 H), 2.26-2.42 (m, 2 H), 2.10-2.23 (m, 1 H), 1.86-2.04 (m, 1 H), 1.40-1.54 (m, 2 H), 0.89 (t, J = 7.29 Hz, 3 H),; MS (M + H)⁺ = 332. |
| Example 4 | Product of Example 1E and n-butyl-aldehyde | Example 2 | 4'-[(3aR,6aR)-5-butylhexahydropyrrolo[3,4-b]pyrrol-1(2H)-yl]-1,1'-biphenyl-4-carbonitrile | $^1$H NMR (CDCl$_3$) δ ppm 7.64 (d, J = 2.03 Hz, 4 H), 7.50 (d, J = 8.81 Hz, 2 H), 6.64 (d, J = 8.82 Hz, 2 H), 4.13-4.25 (m, 1 H), 3.46-3.59 (m, 1 H), 3.27-3.40 (m, 1 H), 2.87-3.04 (m, 1 H), 2.49-2.77 (m, 4 H), 2.29-2.46 (m, 2 H), 2.12-2.24 (m, 1 H), 1.86-2.03 (m, 1 H), 1.23-1.49 (m, J = 44.07 Hz, 4 H), 0.89 (t, J = 7.12 Hz, 3 H); MS (M + H)⁺ = 346. |

TABLE 1-continued

Examples 3-6

| Example | Starting Material | Reaction procedure | Resulting compound | NMR and MS |
|---|---|---|---|---|
| Example 5 | Product of Example 1E and isobutyl-aldehyde | Example 2 | 4'-((3aR,6aR)-5-Isobutyl-hexahydro-pyrrolo[3,4-b]pyrrol-1-yl)-biphenyl-4-carbonitrile | $^1$H NMR (CDCl$_3$) δ ppm 7.64 (d, J = 1.36 Hz, 4 H), 7.50 (d, J = 8.82 Hz, 2 H), 6.64 (d, J = 8.82 Hz, 2 H), 4.13-4.25 (m, 1 H), 3.44-3.54 (m, 1 H), 3.29-3.41 (m, 1 H), 2.86-2.99 (m, 1 H), 2.44-2.70 (m, 4 H), 2.06-2.19 (m, 2 H), 1.86-2.02 (m, 2 H), 1.61-1.77 (m, 1 H), 0.82-0.98 (m, 6 H); MS (M + H)$^+$ = 346. |
| Example 6 | Product of Example 1E and cyclo-propanecarbox-aldehyde | Example 2 | 4'-[(3aR,6aR)-5-(cyclopropylmethyl)hexahydropyrrolo[3,4-b]pyrrol-1(2H)-yl]-1,1'-biphenyl-4-carbonitrile | $^1$H NMR (CDCl$_3$) δ ppm 7.64 (d, J = 2.76 Hz, 4 H), 7.50 (d, J = 8.90 Hz, 2 H), 6.65 (d, J = 8.59 Hz, 2 H), 4.18-4.26 (m, 1 H), 3.51-3.59 (m, 1 H), 3.31-3.41 (m, 1 H), 2.87-3.09 (m, 2 H), 2.73-2.83 (m, 1 H), 2.56-2.70 (m, 2 H), 2.25-2.43 (m, 2 H), 2.12-2.23 (m, 1 H), 1.93-2.05 (m, 1 H), 0.85-0.96 (m, 1 H), 0.12 (d, J = 4.30 Hz, 2 H), 0.50 (d, J = 7.98 Hz, 2 H); MS (M + H)$^+$ = 344. |

Example 7

4'-[(3aR,6aR)-5-methylhexahydropyrrolo[3,4-b]pyrrol-1(2H)-yl]-1,1'-biphenyl-4-carbonitrile

Example 7A (3aR,6aR)-5-Methyl-hexahydro-pyrrolo[3,4-b]pyrrole-1-carboxylic acid tert-butyl ester To a solution of (3aR,6aR)-hexahydro-pyrrolo[3,4-b]pyrrole-1-carboxylic acid tert-butyl ester (18.31 g, 0.86 mol) in methanol (450 ml) was added paraformaldehyde (52 g, 1.72 mole) and the mixture was stirred at room temperature for 1 hour. Sodium cyanoborohydride was then added and the mixture was stirred at room temperature for 10 hours, diluted with 1N NaOH (450 ml), extracted with dichloromethane (5×200 ml). The combined organic layers were dried (Na$_2$SO$_4$), filtered and concentrated to provide the title compound. $^1$H NMR (300 MHz, DMSO-d$_6$) δ ppm 4.18 (m, 1H) 3.47-3.59 (m, 1H) 3.34-3.46 (m, 2H) 2.75-2.90 (m, 1H) 2.71 (m, 1H) 2.44-2.60 (m, 2H) 2.29 (s, 3H) 1.89-2.06 (m, 1H) 1.65-1.81 (m, 1H) 1.42-1.49 (m, 9H). MS: (M+H)$^+$=226.

(3aR,6aR)-Hexahydro-pyrrolo[3,4-b]pyrrole-1-carboxylic acid tert-butyl ester (CAS #370880-09-4) may be prepared as described in Schenke, T., et al, "Preparation of 2,7-Diazabicyclo[3.3.0]octanes", U.S. Pat. No. 5,071,999 (1991) which provides a racemate which may be resolved by chromatography on a chiral column or by fractional crystallization of diasteromeric salts, or as described in Basha, et al. "Substituted diazabicycloalkane derivatives", US 2005101602 (2005).

Example 7B (3aR,6aR)-5-Methyl-hexahydro-pyrrolo[3,4-b]pyrrole

To a solution of the product of Example 7A (20.8 g, 0.86 mole) in methanol (450 ml) was added aqueous 3N HCl (300 ml). The mixture was stirred at room temperature overnight, then concentrated to dryness at 30° C. under vacuum. The residue was treated with aqueous 1N NaOH to obtain a pH of 9-10. The mixture was concentrated to dryness. The crude material was purified by chromatography (eluting with a mixture of 10% methanol and 1% ammonium hydroxide in dichloromethane) to provide the title compound. $^1$H NMR (300 MHz, CDCl$_3$) δ ppm 4.12-4.17 (m, 1H) 3.31-3.43 (m, 1H) 3.19-3.30 (m, 1H) 3.12 (d, J=11.53 Hz, 1H) 2.88-3.01 (m, 1H) 2.69 (dd, J=9.49, 2.37 Hz, 1H) 2.40-2.52 (m, 2H) 2.33 (s, 3H) 2.12-2.28 (m, 1H) 1.82-1.95 (m, 1H). MS: (M+H)$^+$=127.

Example 7C (3aR,6aR)-1-(4-Bromo-phenyl)-5-methyl-octahydro-pyrrolo[3,4-b]pyrrole The product of Example 7B (2.30 g, 18.2 mmole), 1,4-dibromobenzene (5.16 g, 20.9 mmole), tris(dibenzylideneacetone)dipalladium (340 mg, 0.36 mmole), racemic-2,2'-bis(diphenylphosphino)-1,1'-binaphthyl (460 mg, 0.73 mmole) and sodium tert-butoxide (2.63 g, 27.3 mmole) were dissolved in 20 ml of toluene and heated to 70° C. under N$_2$ for 16 hours. The mixture was cooled to room temperature, diluted with water and extracted with dichloromethane (5×). The combined organics were dried over sodium sulfate, filtered and concentrated and purified by chromatography (eluting with a mixture of 5% methanol in dichloromethane) to provide the title compound. $^1$H NMR (300 MHz, CDCl$_3$) δ ppm 7.25-7.30 (m, 2H) 6.41-6.46 (m, 2H) 4.07 (m, 1H) 3.47 (ddd, J=9.1, 7.7, 5.9 Hz, 1H) 3.19 (dt, J=8.9, 7.3 Hz, 1H) 2.95 (m, 1H) 2.68 (dd, J=9.0, 3.0 Hz, 1H) 2.55-2.60 (m, 3H) 2.32 (s, 3H) 2.13-2.22 (m, 1H) 1.88-1.98 (m, 1H). MS: (M+H)$^+$=281/283.

Example 7D (3aR,6aR)-4'-(5-Methyl-hexahydro-pyrrolo[3,4-b]pyrrol-1-yl)-biphenyl-4-carbonitrile The product of Example 7C (30.0 mg, 0.11 mmole), 4-cyanophenylboronic acid (18.8 mg, 0.13 mmole), palladium(II) acetate (1.2 mg, 0.005 mmole), 2-(dicyclohexylphosphino)biphenyl (3.8 mg, 0.01 mmole) and potassium phosphate (K$_3$PO$_4$) (75 mg, 0.35 mmole) were dissolved in 1 ml of toluene, 0.5 ml of isopropanol and 0.5 ml of water. The mixture was stirred at 60° C. under $N_2$ for 5 hours. The mixture was cooled to room temperature, diluted with water and extracted with dichloromethane (5×). The combined organics were dried over sodium sulfate, filtered and concentrated and purified by chromatography (eluting with a mixture of 5% methanol in dichloromethane) to provide the title compound (23.1 mg, 71.3%). 1H NMR (300 MHz, CDCl$_3$) δ ppm 7.60-7.68 (m, 4H) 7.47-7.53 (m, 2H) 6.61-6.68 (m, 2H) 4.14-4.22 (m, 1H) 3.51-3.60 (m, 1H) 3.28-3.35 (m, 1H) 2.93-3.01 (m, 1H) 2.71-2.75 (m, 1H) 2.48-2.61 (m, 3H) 2.32 (s, 3H) 2.14-2.25 (m, 1H) 1.96 (d, J=7.12 Hz, 1H). MS: $(M+H)^+$=281/283.

The following compounds and Examples were made according to the procedures outlined in Example 7C, with the exception that different reagents were substituted to obtain the titled compounds.

TABLE 2

Example 8-38.

| Example | Starting Material | Resulting compound | NMR and MS |
|---|---|---|---|
| Example 8 | Product of Example 7C and 4-methoxyphenyl-boronic acid | (3aR,6aR)-1-(4'-methoxy-1,1'-biphenyl-4-yl)-5-methyloctahydropyrrolo[3,4-b]pyrrole | $^1$H NMR (CDCl$_3$) δ ppm 7.47 (d, J = 9.15 Hz, 2 H), 7.42 (d, J = 9.15 Hz, 2 H), 6.94 (d, J = 8.81 Hz, 2 H), 6.63 (d, J = 8.81 Hz, 2 H), 4.11-4.19 (m, 1 H), 3.83 (s, 3 H), 3.50-3.60 (m, 1 H), 3.22-3.33 (m, 1 H), 2.91-3.03 (m, 1 H), 2.69-2.77 (m, 1 H), 2.52-2.62 (m, 3 H), 2.34 (s, 3 H), 2.11-2.26 (m, 1 H), 1.89-2.01 (m, 1 H); MS (M + H)$^+$ = 309. |
| Example 9 | Product of Example 7C and 4-(cyano-methyl-phenyl)boronic acid | {4'-[(3aR,6aR)-5-methylhexahydropyrrolo[3,4-b]pyrrol-1(2H)-yl]1,1'-biphenyl-4-yl}acetonitrile | $^1$H NMR (CDCl$_3$) δ ppm 7.55 (d, J = 8.48 Hz, 2 H), 7.47 (d, J = 8.81 Hz, 2 H), 7.34 (d, J = 8.48 Hz, 2 H), 6.64 (d, J = 8.82 Hz, 2 H), 4.12-4.23 (m, 1 H), 3.76 (s, 2 H), 3.49-3.63 (m, 1 H), 3.24-3.36 (m, 1 H), 2.90-3.08 (m, 1 H), 2.70-2.80 (m, 1 H), 2.51-2.64 (m, 3 H), 2.35 (s, 3 H), 2.10-2.25 (m, 1 H), 1.89-2.02 (m, 1 H),; MS (M + H)$^+$ = 318. |
| Example 10 | Product of Example 7B and 4-(bromophenyl)acetophenone | 1-{4'-[(3aR,6aR)-5-methylhexahydropyrrolo[3,4-b]pyrrol-1(2H)-yl]-1,1'-biphenyl-4-yl}ethanone | $^1$H NMR (300 MHz, CDCl$_3$) δ ppm 7.96-8.00 (m, 2 H), 7.46-7.57 (m, 4 H), 6.65 (m, 2 H), 4.11-4.22 (m, 1 H), 3.49-3.62 (m, 1 H), 3.26-3.39 (m, 1 H), 2.97 (m, 1 H), 2.69-2.75 (m, 1 H), 2.61 (s, 3 H), 2.50-2.62 (m, 3 H), 2.32 (s, 3 H), 2.13-2.23 (m, 1 H), 1.91-2.01 (m, 1 H); MS (M + H)$^+$ = 321. |
| Example 11 | Product of Example 7C and 3-(4,4,5,5-Tetramethyl-[1,3,2]dioxaborolan-2-yl)-quinoline | 3-{4-[(3aR,6aR)-5-methylhexahydropyrrolo[3,4-b]pyrrol-1(2H)-yl]phenyl}quinoline | $^1$H NMR (CDCl$_3$) δ ppm 9.17 (d, J = 2.37 Hz, 1 H), 8.21 (d, J = 2.37 Hz, 1 H), 8.10 (d, J = 7.80 Hz, 1 H), 7.84 (dd, J = 8.14, 1.36 Hz, 1 H), 7.48-7.71 (m, 4 H), 6.71 (d, J = 8.81 Hz, 2 H), 4.17-4.28 (m, 1 H), 3.55-3.65 (m, 1 H), 3.30-3.40 (m, 1 H), 2.94-3.09 (m, 1 H), 2.72-2.82 (m, 1 H), 2.53-2.70 (m, 3 H), 2.36 (s, 3 H), 2.15-2.29 (m, 1 H), 1.92-2.06 (m, 1 H); MS (M + H)$^+$ = 330. |
| Example 12 | Product of Example 7C and 2-methoxy-5-pridine boronic acid | (3aR,6aR)-1-[4-(6-methoxypyridin-3-yl)phenyl]-5-methyloctahydropyrrolo[3,4-b]pyrrole | $^1$H NMR (300 MHz, CDCl$_3$) δ ppm 8.33 (d, J = 2.03 Hz, 1 H), 7.74 (dd, J = 8.65, 2.54 Hz, 1 H), 7.35-7.44 (m, 2 H), 6.77 (d, J = 9.49 Hz, 1 H), 6.61-6.68 (m, 2 H), 4.10-4.21 (m, 1 H), 3.96 (s, 3 H), 3.50-3.58 (m, 1 H), 3.23-3.31 (m, 1 H), 2.90-3.03 (m, 1 H), 2.55-2.77 (m, 4 H), 2.33 (s, 3 H), 2.12-2.25 (m, 1 H), 1.88-2.03 (m, 1 H); MS (M + H)$^+$ = 310. |
| Example 13 | Product of Example 7C and 4-(hydroxymethylphenyl)boronic acid | {4'-[(3aR,6aR)-5-methylhexahydropyrrolo[3,4-b]pyrrol-1(2H)-yl]-1,1'-biphenyl-4-yl}methanol | $^1$H NMR (CDCl$_3$) δ ppm 7.55 (d, J = 8.14 Hz, 2 H), 7.48 (d, J = 8.82 Hz, 2 H), 7.39 (d, J = 8.14 Hz, 2 H), 6.64 (d, J = 8.82 Hz, 2 H), 4.71 (s, 2 H), 4.13-4.23 (m, 1 H), 3.52-3.61 (m, 2 H), 3.24-3.36 (m, 1 H), 2.92-3.06 (m, 1 H), 2.70-2.77 (m, 1 H), 2.49-2.66 (m, 3 H), 2.35 (s, 3 H), 2.11-2.26 (m, 1 H), 1.88-2.03 (m, 1 H); MS (M + H)$^+$ = 309. |
| Example 14 | Product of Example 7C and 2-cyanopyridine-5-boronic acid pinacolester | 5-{4-[(3aR,6aR)-5-methylhexahydropyrrolo[3,4-b]pyrrol-1(2H)-yl]phenyl}pyridine-2-carbonitrile | $^1$H NMR (300 MHz, CDCl$_3$) δ ppm 8.76 (d, J = 2.37 Hz, 1 H), 8.19 (d, J = 8.14 Hz, 1 H), 7.92-8.01 (m, 1 H), 7.48-7.56 (m, 2 H), 6.62-6.71 (m, 2 H), 4.15-4.26 (m, 1 H), 3.54-3.63 (m, 1 H), 3.34 (m, 1 H), 2.92-3.08 (m, 1 H), 2.51-2.79 (m, 4 H), 2.35 (s, 3 H), 2.15-2.26 (m, 1 H), 1.93-2.08 (m, 1 H); MS (M + H)$^+$ = 305 |

TABLE 2-continued

Example 8-38.

| Example | Starting Material | Resulting compound | NMR and MS |
|---|---|---|---|
| Example 15 | Product of Example 7C and 2,6-Dimethyl-3-(4,4,5,5-tetramethyl-[1,3,2]dioxaborolan-2-yl)-pyridine | (3aR,6aR)-1-[4-(2,6-dimethylpyridin-3-yl)phenyl]-5-methyloctahydropyrrolo[3,4-b]pyrrole | $^1$H NMR (CDCl$_3$) δ ppm 7.40 (d, J = 7.80 Hz, 1 H), 7.17 (d, J = 8.81 Hz, 2 H), 7.00 (d, J = 7.80 Hz, 1 H), 6.62 (d, J = 8.81 Hz, 2 H), 4.09-4.20 (m, 1 H), 3.50-3.60 (m, 1 H), 3.23-3.34 (m, 1 H), 2.90-3.02 (m, 1 H), 2.70-2.78 (m, 1 H), 2.56-2.64 (m, 2 H), 2.55 (s, 3 H), 2.51 (s, 3 H), 2.44-2.49 (m, 1 H), 2.32 (s, 3 H), 2.12-2.24 (m, 1 H), 1.88-2.01 (m, 1 H); MS (M + H)$^+$ = 308. |
| Example 16 | Product of Example 7C and 3-fluoro-4-methoxyphenylboronic acid | (3aR,6aR)-1-(3'-fluoro-4'-methoxy-1,1'-biphenyl-4-yl)-5-methyloctahydropyrrolo[3,4-b]pyrrole | $^1$H NMR (CDCl$_3$) δ ppm 7.42 (d, J = 8.82 Hz, 2 H), 7.20-7.32 (m, 2 H), 6.98-7.04 (m, 1 H), 6.60 (d, J = 8.82 Hz, 2 H), 4.26-4.38 (m, 1 H), 3.91 (s, 3 H), 3.78-3.90 (m, 1 H), 3.53-3.64 (m, 1 H), 3.32-3.45 (m, 1 H), 3.07-3.24 (m, 1 H), 2.68-3.03 (m, 3 H), 2.56 (s, 3 H), 2.13-2.30 (m, 1 H), 1.91-2.10 (m, 1 H); MS (M + H)$^+$ = 327. |
| Example 17 | Product of Example 7C and 2-Methyl-5-(4,4,5,5-tetramethyl-[1,3,2]dioxaborolan-2-yl)-benzothiazole | 2-methyl-5-{4-[(3aR,6aR)-5-methylhexahydropyrrolo[3,4-b]pyrrol-1(2H)-yl]phenyl}-1,3-benzothiazole | 1H NMR (CDCl$_3$) δ ppm 8.11 (d, J = 1.70 Hz, 1 H), 7.81 (d, J = 8.14 Hz, 1 H), 7.51-7.60 (m, 3 H), 6.68 (d, J = 8.81 Hz, 2 H), 4.12-4.22 (m, 1 H), 3.50-3.63 (m, 1 H), 3.24-3.37 (m, 1 H), 2.91-3.06 (m, 1 H), 2.85 (s, 3 H), 2.69-2.79 (m, 1 H), 2.47-2.66 (m, 3 H), 2.33 (s, 3 H), 2.10-2.25 (m, 1 H), 1.87-2.03 (m, 1 H); MS (M + H)$^+$ = 350. |
| Example 18 | Product of Example 7B nd 1-(4-bromophenyl)imidazole | (3aR,6aR)-1-[4-(1H-imidazol-1-yl)phenyl]-5-methyloctahydropyrrolo[3,4-b]pyrrole | $^1$H NMR (CDCl$_3$) δ ppm 7.72 (s, 1 H), 7.21 (d, J = 9.15 Hz, 2 H), 7.15-7.18 (m, 2 H), (d, J = 8.81 Hz, 2 H), 4.09-4.17 (m, 1 H), 3.48-3.59 (m, 1 H), 3.21-3.32 (m, 1 H), 2.92-3.03 (m, 1 H), 2.69-2.75 (m, 1 H), 2.46-2.62 (m, 3 H), 2.32 (s, 3 H), 2.13-2.26 (m, 1 H), 1.90-2.02 (m, 1 H); MS (M + H)$^+$ = 269. |
| Example 19 | Product of Example 7C and 4-(thoxyphenyl)boronic acid | (3aR,6aR)-1-(4'-ethoxy-1,1'-biphenyl-4-yl)-5-methyloctahydropyrrolo[3,4-b]pyrrole | $^1$H NMR (CDCl$_3$) δ ppm 7.44 (dd, J = 8.82, 5.43 Hz, 4 H), 6.93 (d, J = 8.82 Hz, 2 H), 6.62 (d, J = 8.82 Hz, 2 H), 4.20-4.33 (m, 1 H), 4.06 (q, J = 7.12 Hz, 2 H), 3.51-3.64 (m, 1 H), 3.27-3.40 (m, 1 H), 3.02-3.15 (m, 1 H), 2.57-2.93 (m, 4 H), 2.47 (s, 3 H), 2.12-2.26 (m, 1 H), 1.91-2.04 (m, 1 H), 1.43 (t, J = 6.95 Hz, 3 H); MS (M + H)$^+$ = 323. |
| Example 20 | Product of Example 7C and 4(methylthio)phenylboronic acid | (3aR,6aR)-5-methyl-1-[4'-(methylthio)-1,1'-biphenyl-4-yl]octahydropyrrolo[3,4-b]pyrrole | $^1$H NMR (CDCl$_3$) δ ppm 7.48 (d, J = 3.39 Hz, 2 H), 7.45 (d, J = 3.39 Hz, 2 H), 7.27-7.34 (m, 2 H), 6.62 (d, J = 8.81 Hz, 2 H), 4.19-4.32 (m, 1 H), 3.52-3.66 (m, 1 H), 3.28-3.41 (m, 1 H), 3.02-3.17 (m, 1 H), 2.73-2.85 (m, 1 H), 2.59-2.71 (m, 1 H), 2.51 (s, 3 H), 2.41-2.50 (m, 2 H), 2.14-2.28 (m, 1 H), 1.90-2.06 (m, 1 H), 1.68 (s, 3H); MS (M + H)$^+$ = 325. |
| Example 21 | Product of Example 7C and pyridine-4-boronic acid | (3aR,6aR)-5-methyl-1-(4-pyridin-4-ylphenyl)octahydropyrrolo[3,4-b]pyrrole | $^1$H NMR (300 MHz, CDCl$_3$) δ ppm 7.54-7.59 (m, 2 H), 7.18-7.25 (m, 4 H), 6.54-6.60 (m, 2 H), 4.11-4.25 (m, 1 H), 3.47-3.59 (m, 1 H), 3.16-3.36 (m, 1 H), 2.91-3.04 (m, 1 H), 2.64 (m, 4 H), 2.35 (s, 3 H), 2.08-2.26 (m, 1 H), 1.89-2.08 (m, 1 H); MS (M + H)$^+$ = 280. |
| Example 22 | Product of Example 7C and 3-cyanophenyl boronic acid | 4'-[(3aR,6aR)-5-methylhexahydropyrrolo[3,4-b]pyrrol-1(2H)-yl]-1,1'-biphenyl-3-carbonitrile | $^1$H NMR (300 MHz, CDCl$_3$) δ ppm 7.73-7.84 (m, 2 H), 7.39-7.54 (m, 4 H), 6.62-6.69 (m, 2 H), 4.13-4.23 (m, 1 H), 3.48-3.64 (m, 1 H), 3.25-3.41 (m, 1 H), 2.91-3.04 (m, 1 H), 2.69-2.76 (m, 1 H), 2.50-2.68 (m, 3 H), 2.33 (s, 3 H), 2.11-2.25 (m, 1 H), 1.91-2.02 (m, 1 H); MS (M + H)$^+$ = 304. |
| Example 23 | Product of Example 7C and 3,4-methylenedioxybenzene boronic acid | (3aR,6aR)-1-[4-(1,3-benzodioxol-5-yl)phenyl]-5-methyloctahydropyrrolo[3,4-b]pyrrole | $^1$H NMR (CDCl$_3$) δ ppm 7.39 (d, J = 9.15 Hz, 2 H), 7.00 (dd, J = 10.34, 2.20 Hz, 2 H), 6.84 (d, J = 8.48 Hz, 1 H), 6.61 (d, J = 8.81 Hz, 2 H), 5.97 (s, 2 H), 4.12-4.25 (m, 1 H), 3.50-3.62 (m, 1 H), 3.23-3.36 (m, 1 H), 2.92-3.09 (m, 1 H), 2.52-2.82 (m, 4 H), 2.38 (s, 3 H), 2.10-2.26 (m, 1 H), 1.88-2.03 (m, 1 H); MS (M + H)$^+$ = 323. |

TABLE 2-continued

Example 8-38.

| Example | Starting Material | Resulting compound | NMR and MS |
|---|---|---|---|
| Example 24 | Product of Example 7C and pyridine-3-boronic acid | (3aR,6aR)-5-methyl-1-(4-pyridin-3-ylphenyl)octahydropyrrolo[3,4-b]pyrrole | 1H NMR (300 MHz, CDCl$_3$) δ ppm 7.43-7.50 (m, 1 H), 7.17-7.25 (m, 2 H), 6.61-6.74 (m, 2 H), 6.52-6.62 (m, 2 H), 4.05-4.15 (m, 1 H), 3.45-3.56 (m, 1 H), 3.15-3.28 (m, 1 H), 2.87-3.02 (m, 1 H), 2.47-2.70 (m, 4 H), 2.30-2.34 (s, 3 H), 2.09-2.20 (m, 1 H), 1.88-1.98 (m, 1 H); MS (M + H)$^+$ = 280. |
| Example 25 | Product of Example 7C and 2,5-difluoropyridine-3-boronic acid | (3aR,6aR)-1-[4-(2,6-difluoropyridin-3-yl)phenyl]-5-methyloctahydropyrrolo[3,4-b]pyrrole | $^1$H NMR (CDCl$_3$) δ ppm 7.91 (dd, J = 17.63, 7.80 Hz, 1 H), 7.40 (dd, J = 8.98, 1.86 Hz, 1 H), 6.86 (dd, J = 7.80, 3.39 Hz, 1 H), 6.64 (d, J = 8.82 Hz, 2 H), 4.12-4.20 (m, 1 H), 3.50-3.60 (m, 1 H), 3.25-3.35 (m, 1 H), 2.91-3.03 (m, 1 H), 2.69-2.76 (m, 1 H), 2.47-2.64 (m, 3 H), 2.32 (s, 3 H), 2.12-2.24 (m, 1 H), 1.89-2.01 (m, 1 H); MS (M + H)$^+$ = 316. |
| Example 26 | Product of Example 7C and 3-acetylbenzeneboronic acid | 1-{4'-[(3aR,6aR)-5-methylhexahydropyrrolo[3,4-b]pyrrol-1(2H)-yl]-1,1'-biphenyl-3-yl}ethanone | $^1$H NMR (CDCl$_3$) δ ppm 8.13 (t, J = 1.86 Hz, 1 H), 7.84 (d, J = 7.46 Hz, 1 H), 7.74 (d, J = 8.14 Hz, 1 H), 7.51 (t, J = 8.14 Hz, 2 H), 6.64 (d, J = 8.48 Hz, 2 H), 4.28-4.42 (m, 1 H), 3.55-3.67 (m, 1 H), 3.34-3.49 (m, 1 H), 3.12-3.27 (m, 1 H), 2.69-2.98 (m, 4 H), 2.65 (s, 3 H), 2.57 (s, 3 H), 2.15-2.30 (m, 1 H), 1.94-2.11 (m, 1 H); MS (M + H)$^+$ = 321. |
| Example 27 | Product of Example 7C and 4-(ethylthio)benzeneboronic acid | (3aR,6aR)-1-[4'-(ethylthio)-1,1'-biphenyl-4-yl]-5-methyloctahydropyrrolo[3,4-b]pyrrole | $^1$H NMR (CDCl$_3$) δ ppm 7.47 (d, J = 8.14 Hz, 4 H), 7.36 (d, J = 8.81 Hz, 2 H), 6.62 (d, J = 8.81 Hz, 2 H), 4.18-4.32 (m, 1 H), 3.51-3.65 (m, 1 H), 3.28-3.41 (m, 1 H), 3.03-3.16 (m, 1 H), 2.96 (q, J = 7.46 Hz, 2 H), 2.57-2.88 (m, J = 38.31 Hz, 4 H), 2.45 (s, 3 H), 2.13-2.26 (m, 1 H), 1.91-2.08 (m, 1 H), 1.33 (t, J = 7.29 Hz, 3 H); MS (M + H)$^+$ = 339. |
| Example28 | Product of Example 7C and 4-(trifluoromethyl)phenylboronic acid | (3aR,6aR)-5-methyl-1-[4'-(trifluoromethyl)-1,1'-biphenyl-4-yl]octahydropyrrolo[3,4-b]pyrrole | $^1$H NMR (CDCl$_3$) δ ppm 7.63 (s, 4 H), 7.50 (d, J = 8.82 Hz, 2 H), 6.65 (d, J = 8.82 Hz, 2 H), 4.19-4.32 (m, 1 H), 3.51-3.65 (m, 1 H), 3.29-3.42 (m, 1 H), 3.00-3.17 (m, 1 H), 2.58-2.92 (m, 4 H), 2.43 (s, 3 H), 2.12-2.29 (m, 1 H), 1.92-2.07 (m, 1 H); MS (M + H)$^+$ = 347. |
| Example 29 | Product of Example 7C and 4-vinylpnenyl boronic acid | (3aR,6aR)-5-methyl-1-(4'-vinyl-1,1'-biphenyl-4-yl)octahydropyrrolo[3,4-b]pyrrole | $^1$H NMR (CDCl$_3$) δ ppm 7.47-7.55 (m, 4 H), 7.45 (d, J = 8.82 Hz, 2 H), 6.74 (dd, J = 17.63, 10.85 Hz, 1 H), 6.63 (d, J = 8.82 Hz, 2 H), 5.75 (d, J = 17.63 Hz, 1 H), 5.22 (d, J = 10.85 Hz, 1 H), 4.21-4.32 (m, 1 H), 3.52-3.64 (m, 1 H), 3.29-3.42 (m, 1 H), 3.02-3.15 (m, 1 H), 2.61-2.88 (m, 4 H), 2.46 (s, 3 H), 2.12-2.27 (m, 1 H), 1.92-2.04 (m, 1 H); MS (M + H)$^+$ = 305. |
| Example 30 | Product of Example 7C and 4-methyl-3-nitro-phenylboronic acid | (3aR,6aR)-5-methyl-1-(4'-methyl-3'-nitro-1,1'-biphenyl-4-yl)octahydropyrrolo[3,4-b]pyrrole | $^{1H}$ NMR (CDCl$_3$) δ ppm 8.14 (d, J = 2.03 Hz, 1 H), 7.67 (dd, J = 7.80, 2.03 Hz, 1 H), 7.49 (d, J = 8.82 Hz, 2 H), 7.34 (d, J = 7.80 Hz, 1 H), 6.64 (d, J = 8.82 Hz, 2 H), 4.21-4.32 (m, 1 H), 3.52-3.65 (m, 1 H), 3.30-3.43 (m, 1 H), 3.00-3.16 (m, 1 H), 2.68-2.94 (m, 4 H), 2.60 (s, 3 H), 2.44 (s, 3 H), 2.15-2.28 (m, 1 H), 1.93-2.05 (m, 1 H); MS (M + H)$^+$ = 338. |
| Example 31 | Product of Example 7C and 2-4-(dimethoxy)pyrimidine-5-boronic acid | (3aR,6aR)-1-[4-(2,4-dimethoxypyrimidin-5-yl)phenyl]-5-methyloctahydropyrrolo[3,4-b]pyrrole | $^1$H NMR (CDCl$_3$) δ ppm 8.22 (s, 1 H), 7.37 (d, J = 8.82 Hz, 2 H), 6.62 (d, J = 8.82 Hz, 2 H), 4.11-4.24 (m, 1 H), 4.02 (s, 3 H), 4.01 (s, 3 H), 3.50-3.61 (m, 1 H), 3.24-3.35 (m, 1 H), 2.93-3.05 (m, 1 H), 2.69-2.79 (m, 2 H), 2.53-2.64 (m, 2 H), 2.35 (s, 3 H), 2.11-2.25 (m, 1 H), 1.90-2.03 (m, 1 H); MS (M + H)$^+$ = 341 |
| Example 32 | Product of Example 7C and 4-fluorophenyl boronic acid | (3aR,6aR)-1-(4'-fluoro-1,1'-biphenyl-4-yl)-5-methyloctahydropyrrolo[3,4-b]pyrrole | $^1$H NMR (300 MHz, CDCl$_3$) δ ppm 7.40-7.50 (m, 4 H), 7.02-7.11 (m, 2 H), 6.58-6.67 (m, 2 H), 4.13-4.26 (m, 1 H), 3.50-3.63 (m, 1 H), 3.24-3.37 (m, 1 H), 3.01 (m, 1 H), 2.56-2.79 (m, 4 H), 2.38 (s, 3 H), 2.11-2.25 (m, 1 H), 1.91-2.01 (m, 1 H); MS (M + H)$^+$ = 297. |
| Example 33 | Product of Example 7C and 1-naphthalene boronic acid | (3aR,6aR)-5-methyl-1-[4-(1-naphthyl)phenyl]octahydropyrrolo[3,4-b]pyrrole | $^1$H NMR (CDCl$_3$) δ ppm 8.01 (d, J = 8.48 Hz, 1 H), 7.88 (d, J = 9.16 Hz, 1 H), 7.80 (d, J = 8.14 Hz, 1 H), 7.40-7.53 (m, 4 H), 7.38 (d, J = 8.82 Hz, 2 H), 6.69 (d, J = 8.48 Hz, 2 H), 4.21-4.30 (m, 1 H), 3.55-3.66 (m, 1 H), 3.32-3.42 (m, 1 H), 2.99-3.10 (m, 1 H), 2.57-2.93 (m, 4 H), 2.41 (s, 3 H), 2.14-2.27 (m, 1 H), 1.97-2.06 (m, 1 H); MS (M + H)$^+$ = 329 |

TABLE 2-continued

Example 8-38.

| Example | Starting Material | Resulting compound | NMR and MS |
|---|---|---|---|
| Example 34 | Product of Example 7C J = 8.82 Hz, and 3-(hydroxymethyl)phenyl borobic acid | {4'-[(3aR,6aR)-5-methylhexahydropyrrolo[3,4-b]pyrrol-1(2H)-yl]-1,1'-biphenyl-3-yl}methanol | $^1$H NMR (CDCl$_3$) δ ppm 7.55 (s, 1 H), 7.46-7.52 (m, 4 H), 7.39 (t, J = 7.63 Hz, 1 H), 6.64 (d, 2 H), 4.74 (d, J = 5.76 Hz, 2 H), 4.13-4.24 (m, 1 H), 3.50-3.62 (m, 1 H), 3.23-3.39 (m, 1 H), 2.92-3.08 (m, 1 H), 2.69-2.80 (m, 2 H), 2.52-2.66 (m, 2 H), 2.37 (s, 3 H), 2.12-2.27 (m, 1 H), 1.89-2.06 (m, 1 H); MS (M + H)$^+$ = 309 |
| Example 35 | Product of Example 7C and dibenzofuran-2-boronic acid | (3aR,6aR)-1-(4-dibenzo[b,d]furan-4-ylphenyl)-5-methyloctahydropyrrolo[3,4-b]pyrrole | $^1$H NMR (CDCl$_3$) δ ppm 7.98 (d, J = 6.78 Hz, 1 H), 7.80-7.90 (m, 2 H), 7.52-7.65 (m, 2 H), 7.31-7.50 (m, 4 H), 6.69-6.78 (m, 2 H), 4.21-4.34 (m, 1 H), 3.55-3.67 (m, 1 H), 3.33-3.47 (m, 1 H), 2.97-3.13 (m, 1 H), 2.75-2.90 (m, 2 H), 2.54-2.70 (m, 2 H), 2.41 (d, J = 1.36 Hz, 3 H), 2.14-2.29 (m, 1 H), 1.93-2.05 (m, 1 H); MS (M + H)$^+$ = 369 |
| Example 36 | Product of Example 7C and 3-(trifluoromethyl)phenylboronic acid | (3aR,6aR)-5-Methyl-1-(3'-trifluoromethyl-biphenyl-4-yl)-octahydro-pyrrolo[3,4-b]pyrrole | $^1$H NMR (CDCl$_3$) δ ppm 7.77 (s, 1 H), 7.71 (d, J = 1.36 Hz, 1 H), 7.50 (d, J = 2.03 Hz, 2 H), 7.47 (d, J = 1.36 Hz, 2 H), 6.65 (d, J = 8.82 Hz, 2 H), 4.18-4.28 (m, 1 H), 3.52-3.63 (m, 1 H), 3.29-3.40 (m, 1 H), 2.97-3.10 (m, 1 H), 2.71-2.82 (m, 2 H), 2.56-2.69 (m, 2 H), 2.39 (s, 3 H), 2.12-2.28 (m, 1 H), 1.91-2.05 (m, 1 H); MS (M + H)$^+$ = 347 |
| Example 37 | Product of Example 7C and 4-fluoro-3-methyl-phenylboronic acid | (3aR,6aR)-1-(4'-fluoro-3'-methyl-1,1'-biphenyl-4-yl)-5-methyloctahydropyrrolo[3,4-b]pyrrole | $^1$H NMR (CDCl$_3$) δ ppm 7.45 (d, J = 8.14 Hz, 2 H), 7.29-7.36 (m, 2 H), 6.99-7.08 (m, 1 H), 6.59 (d, J = 8.82 Hz, 2 H), 4.52-4.61 (m, 1 H), 4.21-4.36 (m, 1 H), 3.87-4.02 (m, 2 H), 3.55-3.64 (m, 2 H), 3.00-3.51 (m, 1 H), 2.83 (s, 3 H), 2.61-2.78 (m, 1 H), 2.33 (s, 3 H), 2.18-2.29 (m, 1 H), 1.91-2.02 (m, 1 H); MS (M + H)$^+$ = 311 |
| Example 38 | Product of Example 7C and 2-naphthalene boronic acid | (3aR,6aR)-5-methyl-1-[4-(2-naphthyl)phenyl]octahydropyrrolo[3,4-b]pyrrole | $^1$H NMR (CDCl$_3$) δ ppm 7.97 (d, J = 1.70 Hz, 1 H), 7.80-7.89 (m, 3 H), 7.72 (dd, J = 8.48, 1.70 Hz, 1 H), 7.63 (d, J = 8.82 Hz, 2 H), 7.39-7.51 (m, 2 H), 6.68 (d, J = 8.48 Hz, 2 H), 4.24-4.34 (m, 1 H), 3.55-3.67 (m, 1 H), 3.32-3.43 (m, 1 H), 3.04-3.17 (m, 1 H), 2.62-2.87 (m, 4 H), 2.48 (s, 3 H), 2.14-2.30 (m, 1 H), 1.93-2.07 (m, 1 H); MS (M + H)$^+$ = 329 |

Example 39

(1E)-1-{4'-[(3aR,6aR)-5-methylhexahydropyrrolo[3,4-b]pyrrol-1(2H)-yl]-1,1'-biphenyl-4-yl}ethanone oxime To a solution of the product compound of Example 10 (20.0 mg, 0.062 mmole) in 1 ml of ethanol and pyridine (50 μl, 0.62 mmole) was added hydroxylamine hydrochloride (6.5 mg, 0.094 mmole). The mixture was stirred at 80° C. under N$_2$ for 6 hours and the solvent removed under reduced pressure. The residue was purified by chromatography (eluting with a mixture of 0.25% ammonium hydroxide and 2.5% methanol in dichloromethane) to provide the title compound. $^1$H NMR (300 MHz, CDCl$_3$) δ ppm 7.44-7.67 (m, 6H) 6.64 (d, J=8.82 Hz, 2H) 4.14-4.26 (m, 1H) 3.51-3.60 (m, 1H) 3.25-3.39 (m, 1H) 2.89-3.04 (m, 2H) 2.67-2.83 (m, 2H) 2.55-2.61 (m, 2H) 2.35 (s, 3H) 2.30 (s, 3H) 2.16-2.25 (m, 1H) 1.89-2.05 (m, 1H); MS (M+H)$^+$=336.

Example 40

1-{4'-[(3aR,6aR)-5-methylhexahydropyrrolo[3,4-b]pyrrol-1(2H)-yl]-1,1'-biphenyl-4-yl}ethanol To a solution of Example 10 (35.0 mg, 0.11 mmole) in 2 ml of methanol was added sodium borohydride (16.8 mg, 0.44 mmole). The mixture was stirred at room temperature for 24 hours, diluted with water and extracted with dichloromethane (5×). The combined organics were dried over sodium sulfate, filtered and concentrated under reduced pressure and purified by chromatography (eluting with a mixture of 0.25% ammonium hydroxide and 2.5% methanol in dichloromethane) to provide the title compound. $^1$H NMR (300 MHz, CDCl$_3$) δ ppm 7.36-7.63 (m, 6H) 6.63 (d, J=7.46 Hz, 2H) 4.93 (q, J=6.44 Hz, 1H) 4.14-4.27 (m, 1H) 3.49-3.67 (m, 1H) 3.25-3.37 (m, 1H) 2.93-3.10 (m, 1H) 2.54-2.81 (m, J=41.03 Hz, 4H) 2.39 (s, 3H) 2.12-2.24 (m, 1H) 1.97 (dd, J=12.38, 6.27 Hz, 1H) 1.53 (d, J=6.44 Hz, 3H); MS (M+H)$^+$=323.

Example 41

2-{4'-[(3aR,6aR)-5-methylhexahydropyrrolo[3,4-b]pyrrol-1(2H)-yl]-1,1'-biphenyl-4-yl}pyridazin-3(2H)-one

Example 41A (3aR,6aR)-1-(4'-Bromo-biphenyl-4-yl)-5-methyl-octahydro-pyrrolo[3,4-b]pyrrole The title compound was prepared according to the procedure described in Example 7C, substituting 4,4'-dibromobiphenyl for 1,4-dibromobenzene. $^1$H NMR (300 MHz, CDCl$_3$) δ ppm 7.39-7.53 (m, 6H) 6.60-6.66 (m, 2H) 4.17-4.23 (m, 1H) 3.52-3.61 (m, 1H) 3.26-3.35 (m, 1H) 2.98-3.05 (m, 1H)

2.70-2.80 (m, 2H) 2.58-2.64 (m, 2H) 2.38 (s, 3H) 2.15-2.26 (m, 1H) 1.97 (m, 1H). MS: (M+H)+=357/359.

Example 41B

2-{4'-[(3aR,6aR)-5-methylhexahydropyrrolo[3,4-b]pyrrol-1(2H)-yl]-1,1'-biphenyl-4-yl}pyridazin-3(2H)-one The product of Example 41A (4.54 g, 12.6 mmole), 3(2H)-pyridazinone (2.41 g, 25.2 mmole), copper powder (1.60 g, 25.2 mmole) and potassium carbonate (5.21 g, 37.7 mmole) were dissolved in 63 ml of quinoline and heated at 150° C. under $N_2$ for 48 hours. The mixture was cooled to room temperature, diluted with hexane (15 ml) and filtered through CELITE®. The filtrate was concentrated under reduced pressure and the residue was purified by chromatography (eluting first with diethyl ether, followed by dichloromethane, then elution with a mixture of 5% methanol in dichloromethane) to provide the title compound. $^1$H NMR (300 MHz, CDCl$_3$) δ ppm 7.91 (dd, J=3.73, 1.70 Hz, 1H) 7.61-7.65 (m, 4H) 7.51 (d, J=8.48 Hz, 2H) 7.25 (dd, dd, J=9.40, 4.07 Hz, 1H) 7.07 (dd, J=9.49, 1.70 Hz, 1H) 6.64 (d, J=8.81 Hz, 2H) 4.19-4.27 (m, 1H) 3.54-3.64 (m, 1H) 3.28-3.38 (m, 1H) 3.00-3.11 (m, 1H) 2.56-2.85 (m, 4H) 2.40 (s, 3H) 2.10-2.29 (m, 1H) 1.89-2.05 (m, J=6.78 Hz, 1H); MS (M+H)+=373. The solid (3aR,6aR)-2-[4'-(5-methyl-hexahydro-pyrrolo[3,4-b]pyrrol-1-yl)-biphenyl-4-yl]-2H-pyridazin-3-one obtained showed a melting range of 204-207° C. (dec.). To a solution of (3aR,6aR)-2-[4'-(5-methyl-hexahydro-pyrrolo[3,4-b]pyrrol-1-yl)-biphenyl-4-yl]-2H-pyridazin-3-one in methanol was added D-(−)-tartaric acid; a solid formed which was collected by filtration and dried to give a solid of m.p. 218-221° C. In like manner, a methanolic solution of (3aR,6aR)-2-[4'-(5-methyl-hexahydro-pyrrolo[3,4-b]pyrrol-1-yl)-biphenyl-4-yl]-2H-pyridazin-3-one when treated with L-(+)-tartaric acid, followed by concentration of the solution and addition of diethyl ether, gave a solid of m.p. 206-209° C. A methanolic solution of (3aR,6aR)-2-[4'-(5-methyl-hexahydro-pyrrolo[3,4-b]pyrrol-1-yl)-biphenyl-4-yl]-2H-pyridazin-3-one when treated with phosphoric acid, followed by concentration of the solution, gave a solid of m.p. 224-229° C. A methanolic solution of (3aR,6aR)-2-[4'-(5-methyl-hexahydro-pyrrolo[3,4-b]pyrrol-1-yl)-biphenyl-4-yl]-2H-pyridazin-3-one when treated with salicylic acid, followed by concentration of the solution and addition of diethyl ether and hexane, gave a solid of m.p. 115-118° C. A methanolic solution of (3aR,6aR)-2-[4'-(5-methyl-hexahydro-pyrrolo[3,4-b]pyrrol-1-yl)-biphenyl-4-yl]-2H-pyridazin-3-one when treated with ascorbic acid, followed by concentration of the solution and addition of diethyl ether and hexane, gave a solid of m.p. 163-167° C. A methanolic solution of (3aR,6aR)-2-[4'-(5-methyl-hexahydro-pyrrolo[3,4-b]pyrrol-1-yl)-biphenyl-4-yl]-2H-pyridazin-3-one when treated with sulfuric acid, followed by concentration of the solution and addition of diethyl ether, gave a solid of m.p. 232-235° C.

Alternatively, (3aR,6aR)-2-[4'-(5-methyl-hexahydro-pyrrolo[3,4-b]pyrrol-1-yl)-biphenyl-4-yl]-2H-pyridazin-3-one, the product of Example 41B, can be prepared according to the following:

Example 41C

Ethyl(3aR,6aR)-hexahydropyrrolo[3,4-b]pyrrole-5(1H)-carboxylate

The product of Example A5 (205 g) and CH$_2$Cl$_2$ (1 L) were combined and cooled to 0° C. 1.54 L of a 20% KOH solution was cooled to 0° C. then slowly added to the salt slurry and the biphasic reaction mixture was stirred vigorously at 0° C. After 2.75 hours, the layers were separated and the aqueous layer was extracted with CH$_2$Cl$_2$ (1 L). The organic layers were combined and concentrated under reduced pressure, then chased with toluene (1.6 L) to provide 386 g of a 19 wt % solution of product (100%).

Example 41D

Ethyl(3aR,6aR)-1-(4'-bromo-1,1'-biphenyl-4-yl)hexahydropyrrolo[3,4-b]pyrrole-5(1H)-carboxylate To a vessel containing 4,4'-dibromobiphenyl (12.48 g, 2.0 equiv.) and cesium carbonate (13.04 g, 2.0 eq.) was added the product of Example 41C (17.9 wt %, 20.6 g, 1.0 eq.) after which the vessel was evacuated and purged. A catalyst solution was prepared in a separate vessel by mixing Xantphos (0.77 g, 0.067 eq.) and palladium (II) acetate (0.22 g, 0.049 eq.) and degassed after which 17.3 g of toluene was added with stirring.

The catalyst solution was added to the vessel containing the 4,4'-dibromobiphenyl, cesium carbonate, and the product of Example 41C and the mixture was heated to 98° C. for 12 hours. The mixture was cooled to 20° C. and 80 g of dichloromethane was added. The resulting mixture was stirred and then filtered to remove the catalyst. The resulting solution was concentrated under reduced pressure and the residue was purified by column chromatography to yield 5.65 g of the title compound.

Example 41E

Ethyl(3aR,6aR)-1-[4'-(6-oxopyridazin-1(6H)-yl)-1,1'-biphenyl-4-yl]hexahydropyrrolo[3,4-b]pyrrole-5(1H)-carboxylate A mixture of 1.98 g of copper (I) iodide (10.4 mmole, 0.10 eq.), 1.66 g of 8-hydroxyquinoline (11.44 mmole, 0.11 eq.), 4.0 g of potassium carbonate (28.94 mmole, 0.29 eq.) in 18.8 g of dimethylformamide (DMF) was mixed at ambient temperature. The mixture was added to another flask containing 41.6 g of the product of Example 41D (100.16 mmole, 1.00 eq.), 23.6 g of potassium carbonate (170.75 mmole, 1.70 eq.), and 14.4 g of pyridazinone (149.86 mmole, 1.50 eq.). Additional DMF (226 g) was used to transfer the catalyst slurry. The resulting mixture was deoxygenated then heated to 140° C. for about 18 hours. After cooling to ambient temperature the mixture was diluted with 567 g of THF and 384 g of 10% sodium chloride solution. The mixture was filtered to remove excess salts and the aqueous phase was separated and back extracted with an additional 177 g of THF. The combined organic phases were then washed with 10% sodium chloride solution (3×384 g). The organic phase was concentrated under reduced pressure and methanol (253 g) was added and the contents were concentrated under reduced pressure. After adding additional methanol (158 g) the contents were cooled to 0° C., filtered, and washed with cold methanol. The resulting solids were transferred to a vacuum oven to yield 35.31 g (81.9% yield). Mass Spectroscopy: 431.5 (m.w. 430.5). $^1$H NMR (400 MHz, DMSO-d$_6$) δ ppm 1.15 (s, 3H), 1.78-1.88 (m, 1H), 2.10 (ddd, J=12.49, 6.17, 6.04 Hz, 1H), 3.03 (s, 1H), 3.24-3.35 (m, 5H), 3.53 (ddd, J=9.23, 6.86, 6.69 Hz, 2H), 3.67 (s, 1H), 4.00 (s, 2H), 4.22 (s, 1H), 6.63 (d, J=8.51 Hz, 2H), 7.07 (dd, J=9.47, 1.51 Hz, 1H), 7.48 (dd, J=9.47, 3.84 Hz, 1H), 7.53-7.60 (m, 4H), 7.68 (d, J=8.64 Hz, 2H), 8.06 (dd, J=3.84, 1.51 Hz, 1H). $^{13}$C NMR (100 MHz, DMSO-d6) δ ppm 14.79 (CH3), 28.89 (CH$_2$), 47.71 (CH$_2$), 60.24 (CH$_2$), 112.34 (CH), 124.87 (CH), 125.27 (CH), 126.02 (C), 126.89 (CH), 130.05 (CH), 131.69 (CH), 136.87 (CH), 138.78 (C), 139.31 (C), 145.61 (C), 153.53 (C), 158.64 (C).

Example 41F

2-{4'-[(3aR,6aR)-Hexahydropyrrolo[3,4-b]pyrrol-1(2H)-yl]-1,1'-biphenyl-4-yl}pyridazin-3(2H)-one A mixture of the product of Example 41E (7.50 g, 17.42 mmol) in 33% HBr in acetic acid (37 mL, 205.57 mmol, 11.8 equivalents) was heated to 65-70° C. for at least 6 hours while monitored by HPLC analysis for completion. When reaction is complete the mixture is cooled to not more than 45° C. and is diluted with methanol (111 mL). The mixture was cooled to 20-25° C., the product is collected by filtration and is washed with fresh methanol (50 mL). The wet cake is dried in the vacuum oven at not more than 55° C. to provide the title compound (7.25 g, 94.8%).

Example 41G

2-[4'-(3aR,6aR)-(5-Methylhexahydropyrrolo[3,4-b]pyrrol-1(2H)-yl)-1,1'-biphenyl-4-yl]pyridazin-3(2H)-one To a stirred solution of the product of Example 41F (13.80 g, 31.41 mmol) in dimethylacetamide (500 mL) was added a solution of 37% aqueous formaldehyde (7.2 mL, 94.23 mmol, 3.0 equivalents) followed by sodium triacetoxyborohydride (20.0 g, 94.23 mmol, 3.0 equivalents). The mixture was stirred at 25+/−5° C. for 30 minutes during which the starting material was consumed, giving a clear solution. The mixture was diluted with 1N HCl (94 mL, 94 mmol, 3 equivalents) and stirred for one hour. The mixture was adjusted to pH 9.0+/−0.5 with 1N NaOH (335 mL). The mixture was stirred for 1 hour then filtered. The wet cake was washed with water and dried in a vacuum oven at about 50° C. to provide the title compound (10.40 g, 88.9%).

Example 41H

2-[4'-(3aR,6aR)-(5-Methylhexahydropyrrolo[3,4-b]pyrrol-1(2H)-yl)-1,1'-biphenyl-4-yl]pyridazin-3(2H)-one L-tartrate A solution of 3.45 g of L-tartaric acid (1.07 eq.) in 56 g of water was added to a flask containing a slurry of 8.00 g of the product of Example 41G in anhydrous ethanol (44 g). The mixture was heated under reflux and after 30 minutes most solids had dissolved. The mixture was cooled at 5° C. per hour to 60° C., and then allowed to cool to ambient temperature overnight. After cooling the mixture to −15° C. the product slurry was filtered and dried at 45-50° C. overnight to provide the title compound (10.64 g, 94.8%).

Example 42

(3aR,6aR)-5-methyl-1-(4'-pyrimidin-5-yl-1,1'-biphenyl-4-yl)octahydropyrrolo[3,4-b]pyrrole The title compound was prepared according to the procedure described in Example 7D, substituting the product of Example 41A for the product of Example 7C and substituting pyrimidine-5-boronic acid for 4-cyanophenylboronic acid. $^1$H NMR (300 MHz, CDCl$_3$) δ ppm 9.19 (s, 1H) 8.99 (s, 2H) 7.62-7.74 (m, 4H) 7.52-7.58 (m, 2H) 6.63-6.70 (m, 2H) 4.20-4.31 (m, 1H) 3.55-3.67 (m, 1H) 3.30-3.42 (m, 1H) 2.99-3.14 (m, 1H) 2.60-2.84 (m, 4H) 2.42 (s, 3H) 2.16-2.26 (m, 1H) 1.95-2.05 (m, 1H); MS (M+H)$^+$=357.

The following compounds and Examples were made according to the procedures outlined in Example 42, with the exception that different reagents were substituted to obtain the titled compounds.

TABLE 3

Example 43-47.

| Example | Starting Material | Resulting compound | NMR and MS |
|---|---|---|---|
| Example 43 | Product of Example 41A and 3-cyanophenylboronic acid | 4'''-[(3aR,6aR)-5-methylhexahydropyrrolo[3,4-b]pyrrol-1(2H)-yl]-1,1':4',1''-terphenyl-3-carbonitrile | $^1$H NMR (300 MHz, CDCl$_3$) δ ppm 7.82-7.91 (m, 2 H), 7.47-7.68 (m, 8 H), 6.61-6.70 (m, 2 H), 4.20-4.33 (m, 1 H), 3.53-3.66 (m, 1 H), 3.28-3.43 (m, 1 H), 3.00-3.19 (m, 1 H), 2.61-2.91 (m, 4 H), 2.44 (s, 3 H), 2.15-2.28 (m, 1 H), 2.03 (d, 1 H); MS (M + H)$^+$ = 380. |
| Example 44 | Product of Example 41A and 2-fluoropyridine-5-boronic acid | (3aR,6aR)-1-[4'-(6-fluoropyridin-3-yl)-1,1'-biphenyl-4-yl]-5-methyloctahydropyrrolo[3,4-b]pyrrole | $^1$H NMR (300 MHz, CDCl$_3$) δ ppm 8.43 (dd, J = 18.14, 2.54 Hz, 1 H), 7.92-8.04 (m, 1 H), 7.33-7.71 (m, 6 H), 6.97-7.09 (m, 1 H), 6.62-6.68 (m, 2 H), 4.18-4.31 (m, 1 H), 3.54-3.67 (m, 1 H), 3.26-3.41 (m, 1 H), 2.96-3.16 (m, 1 H), 2.56-2.89 (m, 4H), 2.43 (s, 3 H), 2.12-2.27 (m, 1 H), 1.95-2.07 (m, 1 H); MS (M + H)$^+$ = 374. |
| Example 45 | Product of Example 41A and 2,6-dimethylpyridine-5-boronic acid pinacol ester | (3aR,6aR)-1-[4'-(2,6-dimethylpyridin-3-yl)-1,1'-biphenyl-4-yl]-5-methyloctahydropyrrolo[3,4-b]pyrrole | $^1$H NMR (300 MHz, CDCl$_3$) δ ppm 7.28-7.85 (m, 7 H), 7.02-7.07 (m, 1 H), 6.59-6.68 (m, 2 H), 4.15-4.28 (m, 1 H), 3.54-3.65 (m, 1 H), 3.30-3.36 (m, 1 H), 2.95-3.09 (m, 1 H), 2.51-2.59 (4, 3 H), 2.57 (6, 3 H), 2.48 (s, 3 H), 2.13-2.23 (m, 1 H), 1.94-2.08 (m, 1 H); MS (M + H)$^+$ = 384. |

TABLE 3-continued

Example 43-47.

| Example | Starting Material | Resulting compound | NMR and MS |
|---|---|---|---|
| Example 46 | Product of Example 41A and 2-chloropyridine-5-boronic acid | (3aR,6aR)-1-[4'-(6-chloropyridin-3-yl)-1,1'-biphenyl-4-yl]-5-methyloctahydropyrrolo[3,4-b]pyrrole | $^1$H NMR (300 MHz, CDCl$_3$) δ ppm 8.68 (s, 1 H), 8.52 (d, J = 4.75 Hz, 1 H), 7.33-7.72 (m, 6H), 6.61-6.69 (m, 3 H), 4.17-4.34 (m, 1 H), 3.54-3.68 (m, 1 H), 3.28-3.41 (m, 1 H), 2.95-3.17 (m, 1 H), 2.54-2.82 (m, 4 H), 2.41 (s, 3 H), 2.16-2.27 (m, 1 H), 1.90-2.05 (m, 1 H); MS (M + H)$^+$ = 390. |
| Example 47 | Product of Example 41A and 4-cyanophenylboronic acid | 4''-[(3aR,6aR)-5-methylhexahydropyrrolo[3,4-b]pyrrol-1(2H)-yl]-1,1':4',1''-terphenyl-4-carbonitrile | $^1$H NMR (300 MHz, CDCl$_3$) δ ppm 7.72 (s, 4 H), 7.59-7.69 (m, 4 H), 7.54 (d, J = 8.81 Hz, 2 H), 6.66 (d, J = 8.81 Hz, 2 H), 4.20-4.30 (m, 1 H), 3.52-3.66 (m, 1 H), 3.29-3.43 (m, 1 H), 2.97-3.14 (m, 1 H), 2.59-2.84 (m, 4 H), 2.42 (s, 3 H), 2.12-2.27 (m, 1 H), 1.93-2.06 (m, 1 H); MS (M + H)$^+$ = 380. |

Example 48

6-(4-{4-[(3aR,6aR)-5-methylhexahydropyrrolo[3,4-b]pyrrol-1(2H)-yl]phenyl}piperazin-1-yl)nicotinonitrile Example 48A 6-piperazin-1-yl-nicotinonitrile 6-Chloronicotinonitrile (500 mg, 3.61 mmole) and piperazine (930 mg, 10.8 mmole) were dissolved in 20 ml of acetonitrile and heated at 60° C. under N$_2$ for 5 hours. The mixture was cooled to room temperature, diluted with water and extracted with dichloromethane (5×). The combined organics were dried over sodium sulfate, filtered, and concentrated to provide the title compound. $^1$H NMR (300 MHz, CDCl$_3$) δ 8.40 (d, J=1.70 Hz, 1H) 7.60 (dd, J=8.81, 2.37 Hz, 1H) 6.59 (d, J=8.48 Hz, 1H) 3.57-3.75 (m, 4H) 2.91-3.05 (m, 4H); MS (M+H)$^+$=189.

Example 48B (3aR,6aR)-6-{4-[4-(5-Methyl-hexahydro-pyrrolo[3,4-b]pyrrol-1-yl)-phenyl]-piperazin-1-yl}-nicotinonitrile The product of Example 7C (281.2 mg, 1.0 mmole), the product of Example 48A (226 mg, 1.2 mmole), tris(dibenzylideneacetone)dipalladium (18.3 mg, 0.02 mmole), racemic-2,2'-bis(diphenylphosphino)-1,1'-binaphthyl (25.0 mg, 0.04 mmole) and sodium tert-butoxide (145 mg, 1.5 mmole) were dissolved in 5 ml of toluene and heated at 70° C. under N$_2$ for 24 hours. The mixture was cooled to room temperature, diluted with water and extracted with dichloromethane (5×). The combined organics were dried over sodium sulfate, filtered, and concentrated under reduced pressure and purified by chromatography (eluting with a mixture of 5% methanol in dichloromethane) to provide the title compound. $^1$H NMR (300 MHz, CDCl$_3$) δ ppm 8.43 (d, J=1.70 Hz, 1H) 7.62 (dd, J=8.98, 2.20 Hz, 1H) 6.92 (d, J=8.81 Hz, 2H) 6.64 (d, J=9.15 Hz, 1H) 6.56 (d, J=9.15 Hz, 2H) 4.01-4.15 (m, 4H) 3.79-3.88 (m, 4H) 3.45-3.55 (m, 1H) 3.14-3.23 (m, 1H) 3.08-3.14 (m, 4H) 2.97-3.04 (m, 1H) 2.55-2.75 (m, 4H) 2.36 (s, 3H) 2.09-2.22 (m, 1H) 1.92 (m, 1H); MS (M+H)$^+$=389.

Example 49

(3aR,6aR)-1-{4-[4-(6-chloropyridazin-3-yl)piperazin-1-yl]phenyl}-5-methyloctahydropyrrolo[3,4-b]pyrrole Example 49A (3aR,6aR)-1-{4-[4-(5-Methyl-hexahydro-pyrrolo[3,4-b]pyrrol-1-yl)-phenyl]-piperazin-1-yl}-ethanone The product of Example 7C (500 mg, 1.78 mmole), 1-acetylpiperazine (274 mg, 2.13 mmole), tris(dibenzylideneacetone)dipalladium (32.6 mg, 0.036 mmole), (r)-(+)-2,2'-bis(diphenylphosphino)-1,1'-binaphthyl were (44.3 mg, 0.071 mmole), sodium tert-butoxide (256 mg, 2.67 mmole) and 5 ml of toluene were mixed under N$_2$ in a Emrys process vial. The vial was sealed, then heated in the microwave for 20 minutes at 150° C., using the Emrys Creator microwave reactor. The mixture was diluted with water and extracted with dichloromethane (4×). The combined organic layers were washed with brine, dried over sodium sulfate, filtered, concentrated under reduced pressure and purified by column chromatography (eluting with a mixture of 10% methanol and 1% ammonium hydroxide in dichloromethane) to provide the title compound. $^1$H NMR (300 MHz, CDCl$_3$) δ ppm 6.87-6.91 (m, 2H) 6.53-6.60 (m, 2H) 4.05-4.07 (m, 1H) 3.73-3.79 (m, 2H) 3.57-3.63 (m, 2H) 3.46-3.54 (m, 1H) 3.12-3.20 (m, 1H) 2.96-3.03 (m, 4H) 2.56-2.71 (m, 5H) 2.34 (s, 3H) 2.14-2.18 (m, 1H) 2.13 (s, 3H) 1.87-1.97 (m, 1H). MS: (M+H)$^+$=329.

Example 49B (3aR,6aR)-5-Methyl-1-(4-piperazin-1-yl-phenyl)-octahydro-pyrrolo[3,4-b]pyrrole The product of Example 49A (300 mg, 0.91 mmole) was dissolved in 6 ml of 2N hydrochloric acid and 3 ml of methanol and stirred at 60° C. for 3 hours. The mixture was concentrated to dryness under reduced pressure, diluted with water and extracted with dichloromethane (4×). The combined organic layers were dried over sodium sulfate, filtered, and concentrated under reduced pressure and purified by column chromatography (eluting with a mixture of 10% methanol and 1% ammonium hydroxide in dichloromethane) to provide the title compound. $^1$H NMR (300 MHz, CDCl$_3$) δ ppm 6.84-6.94 (m, 2H) 6.53-6.60 (m, 2H) 4.00-4.07 (m, 1H) 3.44-3.51 (m, 1H) 3.11-3.20 (m, 1H) 2.99-3.09 (m, 9H) 2.88-2.96 (m, 1H) 2.68 (dd, J=9.66, 2.54 Hz, 1H) 2.48-2.59 (m, 2H) 2.31 (s, 3H) 2.09-2.19 (m, 1H) 1.89 (m, 1H). MS: (M+H)$^+$=287.

Example 49C (3aR,6aR)-1-{4-[4-(6-Chloro-pyridazin-3-yl)-piperazin-1-yl]-phenyl}-5-methyl-octahydro-pyrrolo[3,4-b]pyrrole The product of Example 49B (30 mg, 0.105 mmole), 3,6-dichloropyridazine (18.8 mg, 0.126 mmole), and triethylamine (45 ml, 0.036 mmole) were dissolved in 1 ml of acetonitrile and heated at 60° C. under N$_2$ for 24 hours. The mixture was cooled to room temperature, quenched with water and extracted with dichloromethane (5×). The combined organics were dried over sodium sulfate, filtered and concentrated under reduced pressure and purified by chromatography (eluting with a mixture of 0.5% ammonium hydroxide and 5% methanol in dichloromethane) to provide the title compound. $^1$H NMR (300 MHz, CDCl$_3$) δ ppm 7.24 (s, 1H) 7.21 (s, 1H) 6.91-6.96 (m, 2H) 6.53-6.58 (m, 2H) 4.13-4.21 (m, 1H) 3.72-3.83 (m, 4H) 3.50-3.61 (m, 1H) 3.36-3.45 (m, 1H) 3.11-3.19 (m, 4H) 2.99-3.08 (m, 1H) 2.60-2.80 (m, 4H) 2.46 (s, 3H) 2.13-2.23 (m, 1H) 1.89-2.04 (m, 1H); MS: (M+H)$^+$=399.

Example 50

(3aR,6aR)-5-methyl-1-{4-[4-(1,3-thiazol-2-yl)piperazin-1-yl]phenyl}octahydropyrrolo[3,4-b]pyrrole The product of Example 49B (50 mg, 0.175 mmole), 2-bromothiazole (35 mg, 0.21 mmole), tris(dibenzylideneacetone)dipalladium (3.2 mg, 0.0035 mmole), racemic-2,2'-bis(diphenylphosphino)-1,1'-binaphthyl (4.4 mg, 0.007 mmole) and sodium tert-butoxide (25.2 mg, 1.5 mmole) were dissolved in 1 ml of toluene and heated at 80° C. under N$_2$ for 24 hours. The mixture was cooled to room temperature, diluted with water and extracted with dichloromethane (5×). The combined organics were dried over sodium sulfate, filtered, concentrated under reduced pressure and was purified by chromatography (eluting with a mixture of 5% methanol in dichloromethane) to provide the title compound. $^1$H NMR (300 MHz, CDCl$_3$) δ ppm 7.22 (d, J=3.73 Hz, 1H) 6.88-6.96 (m, 2H) 6.59 (d, J=3.73 Hz, 1H) 6.50-6.58 (m, 2H) 4.06-4.22 (m, 1H) 3.60-3.69 (m, 4H) 3.48-3.58 (m, 1H) 3.17-3.27 (m, 1H) 3.11-3.17 (m, 4H) 2.95-3.07 (m, 1H) 2.61-2.71 (m, 4H) 2.41 (s, 3H) 2.10-2.22 (m, 1H) 1.93-1.97 (m, 1H); MS (M+H)$^+$=370.

The following compounds and Examples were made according to the procedures outlined above with the exception that different reagents were substituted to obtain the titled compounds.

TABLE 4

Examples 51-66.

| Example | Starting Material | Reaction procedure | Resulting compound | NMR and MS |
|---|---|---|---|---|
| Example 51 | Product of Example 7C and 1(2-pyridinyl)piperazine | Example 48B | (3aR,6aR)-5-methyl-1-[4-(4-pyridin-2-ylpiperazin-1-yl)phenyl]octahydropyrrolo[3,4-b]pyrrole | $^1$H NMR (300 MHz, CDCl$_3$) δ ppm 8.17-8.25 (m, 1 H), 7.44-7.54 (m, 1 H), 6.87-7.01 (m, 2 H), 6.60-6.73 (m, 2 H), 6.49-6.60 (m, 2 H), 3.98-4.10 (m, 1 H), 3.64-3.76 (m, 4 H), 3.44-3.56 (m, 1 H), 3.18-3.25 (m, 1 H), 3.10-3.19 (m, 4 H), 2.97-3.04 (m, 1 H), 2.50-2.70 (m, 4 H), 2.32 (s, 3 H), 2.09-2.20 (m, 1 H) 1.84-1.96 (m, 1 H); MS (M + H)$^+$ = 364. |
| Example 52 | Product of Example 7C and 1(4-nitrophenyl)piperazine | Example 48B | (3aR,6aR)-5-methyl-1-{4-[4-(4-nitrophenyl)piperazin-1-yl]phenyl}octahydropyrrolo[3,4-b]pyrrole | $^1$H NMR (300 MHz, CDCl$_3$) δ ppm 8.15 (d, J = 9.49 Hz, 2 H), 7.19-7.24 (m, 2 H), 6.88 (d, J = 9.49 Hz, 2 H), 6.56 (d, J = 8.48 Hz, 2 H), 4.12-4.31 (m, 1 H), 3.53-3.62 (m, 4 H), 3.46-3.54 (m, 1 H), 3.24-3.38 (m, 1 H), 3.14-3.22 (m, 4 H), 2.96-3.09 (m, 1 H), 2.58-2.80 (m, 4 H), 2.49 (s, 3 H), 2.11-2.22 (m, 1 H), 1.93-2.06 (m, 1 H); MS (M + H)$^+$ = 407. |
| Example 53 | Product of Example 7C and 1(2-cyanophenyl)piperazine | Example 48B | 2-(4-{4-[(3aR,6aR)-5-methylhexahydropyrrolo[3,4-b]pyrrol-1(2H)-yl]phenyl}piperazin-1-yl)benzonitrile | $^1$H NMR (300 MHz, CDCl$_3$) δ ppm 7.46-7.61 (m, 1 H), 7.16-7.25 (m, 2 H), 6.99-7.08 (m, 1 H), 6.91-6.97 (m, 1 H), 6.69 (t, J = 7.29 Hz, 1 H), 6.58 (d, J = 7.46 Hz, 2 H), 4.08-4.14 (m, 1 H), 3.47-3.54 (m, 1 H), 3.34-3.42 (m, 4 H), 3.22-3.28 (m, 4 H), 3.13-3.21 (m, 1 H), 2.87-2.96 (m, 1 H), 2.64-2.73 (m, 1 H), 2.47-2.61 (m, 3 H), 2.29-2.33 (m, 3 H), 2.09-2.21 (m, 1 H), 1.86-1.98 (m, 1 H); MS (M + H)$^+$ = 388. |

TABLE 4-continued

Examples 51-66.

| Example | Starting Material | Reaction procedure | Resulting compound | NMR and MS |
|---|---|---|---|---|
| Example 54 | Product of Example 49B and 4-chloropyridine hydrochloride | Example 49C | (3aR,6aR)-5-methyl-1-[4-(4-pyridin-4-ylpiperazin-1-yl)phenyl]octahydropyrrolo[3,4-b]pyrrole | $^1$H NMR (300 MHz, CDCl$_3$) δ ppm 8.28 (d, J = 6.44 Hz, 2 H), 6.89-6.96 (m, 2 H), 6.73 (d, J = 6.44 Hz, 2 H), 6.57 (d, J = 8.82 Hz, 2 H), 4.03-4.19 (m, 1 H), 3.60-3.69 (m, 1 H), 3.47-3.56 (m, 4 H), 3.36-3.45 (m, 1 H), 3.11-3.21 (m, 4 H), 3.01-3.10 (m, 1 H), 2.56-2.77 (m, 4 H), 2.39 (s, 3 H), 2.12-2.19 (m, 1 H), 1.86-2.00 (m, 1 H); MS (M + H)$^+$ = 364. |
| Example 55 | Product of Example 49B and 3-chloro-6-methylpyridazine | Example 49C | (3aR,6aR)-5-methyl-1-{4-[4-(6-methylpyridazin-3-yl)piperazin-1-yl]phenyl}octahydropyrrolo[3,4-b]pyrrole | $^1$H NMR (300 MHz, CDCl$_3$) δ ppm 7.10 (d, J = 9.16 Hz, 1 H), 6.94 (d, J = 8.82 Hz, 2 H), 6.90 (d, J = 9.49 Hz, 1 H), 6.57 (d, J = 9.16 Hz, 2 H), 3.99-4.10 (m, 1 H), 3.72-3.80 (m, 4 H), 3.44-3.56 (m, 1 H), 3.11-3.22 (m, 4 H), 3.01-3.09 (m, 1 H), 2.85-2.97 (m, 1 H), 2.65-2.74 (m, 1 H), 2.56 (s, 3 H), 2.51-2.62 (m, 3 H), 2.33 (s, 3 H), 2.07-2.22 (m, 1 H), 1.82-2.00 (m, 1 H); MS (M + H)$^+$ = 379. |
| Example 56 | Product of Example 49B and 2-iodppyrazine | Example 49C | (3aR,6aR)-5-methyl-1-[4-(4-pyrazin-2-ylpiperazin-1-yl)phenyl]octahydropyrrolo[3,4-b]pyrrole | $^1$H NMR (300 MHz, CDCl$_3$) δ ppm 8.19 (d, J = 1.36 Hz, 1 H), 8.08 (dd, J = 2.71, 1.70 Hz, 1 H), 7.87 (d, J = 2.71 Hz, 1 H), 6.95 (d, J = 8.81 Hz, 2 H), 6.55 (d, J = 8.81 Hz, 2 H), 4.13-4.29 (m, 1 H), 3.70-3.81 (m, 4 H), 3.52-3.58 (m, 1 H), 3.21-3.30 (m, 1 H), 3.11-3.20 (m, 4 H), 3.00-3.11 (m, 1 H), 2.58-2.83 (m, 4 H), 2.54 (s, 3 H), 2.12-2.22 (m, 1 H), 1.92-2.04 (m, 1 H); MS (M + H)$^+$ = 365. |
| Example 57 | Product of Example 49B and 2-chloropyrimidine | Example 49C | (3aR,6aR)-5-methyl-1-[4-(4-pyrimidin-2-ylpiperazin-1-yl)phenyl]octahydropyrrolo[3,4-b]pyrrole | $^1$H NMR (300 MHz, CDCl$_3$) δ ppm 8.33 (d, J = 4.75 Hz, 2 H), 6.91-6.96 (m, 2 H), 6.53-6.58 (m, 2 H), 6.50 (t, J = 4.75 Hz, 1 H), 4.06-4.16 (m, 1 H), 3.93-4.00 (m, 4 H), 3.47-3.57 (m, 1 H), 3.14-3.27 (m, 1 H), 3.06-3.12 (m, 4 H), 2.95-3.05 (m, 1 H), 2.56-2.78 (m, 4 H), 2.40 (s, 3 H), 2.08-2.23 (m, 1 H), 1.88-2.00 (m, 1 H); MS (M + H)$^+$ = 365. |
| Example 58 | Product of Example 49B and 4-bromobenzonitrile | Example 49C | 4-(4-{4-[(3aR,6aR)-5-methylhexahydropyrrolo[3,4-b]pyrrol-1(2H)-yl]phenyl}piperazin-1-yl)benzonitrile | $^1$H NMR (300 MHz, CDCl$_3$) δ ppm 7.52 (d, J = 8.82 Hz, 2 H), 6.94 (d, J = 6.44 Hz, 2 H), 6.91 (d, J = 6.44 Hz, 2 H), 6.56 (d, J = 8.82 Hz, 1 H), 4.11-4.25 (m, 1 H), 3.52-3.62 (m, 1 H), 3.43-3.51 (m, 4 H), 3.21-3.30 (m, 1 H), 3.13-3.21 (m, 4 H), 3.00-3.05 (m, 1 H), 2.56-2.77 (m, 4 H), 2.43-2.49 (s, 3 H), 2.11-2.22 (m, 1 H), 1.91-2.03 (m, 1 H); MS (M + H)$^+$ = 388. |
| Example 59 | Product of Example 49B and 2-chloro-5-ethylpyrimidine | Example 50 | (3aR,6aR)-1-{4-[4-(5-ethylpyrimidin-2-yl)piperazin-1-yl]phenyl}-5-methyloctahydropyrrolo[3,4-b]pyrrole | $^1$H NMR (300 MHz, CDCl$_3$) δ ppm 8.20 (s, 2 H), 6.91-6.97 (m, 2 H), 6.53-6.59 (m, 2 H), 4.02-4.17 (m, 1 H), 3.89-3.98 (m, 4 H), 3.50-3.55 (m, 1 H), 3.15-3.24 (m, 1 H), 3.06-3.13 (m, 4 H), 2.89-3.03 (m, 1 H), 2.55-2.74 (m, 4 H), 2.48 (q, J = 7.57 Hz, 2 H), 2.34-2.40 (s, 3 H), 2.11-2.21 (m, 1 H), 1.86-1.99 (m, 1 H), 1.20 (t, J = 7.63 Hz, 3 H); MS (M + H)$^+$ = 393. |
| Example 60 | Product of Example 49B and 5-bromopyrimidine | Example 50 | (3aR,6aR)-5-methyl-1-[4-(4-pyrimidin-5-ylpiperazin-1-yl)phenyl]octahydropyrrolo[3,4-b]pyrrole | $^1$H NMR (300 MHz, CDCl$_3$) δ ppm 8.72 (s, 1 H), 8.42 (s, 2 H), 6.85-7.00 (m, 2 H), 6.50-6.62 (m, 2 H), 4.03-4.12 (m, 1 H), 3.47-3.58 (m, 1 H), 3.37-3.45 (m, 4 H), 3.15-3.26 (m, 4 H), 3.05-3.12 (m, 1 H), 2.90-3.02 (m, 1 H), 2.65 (m, 4 H), 2.36 (s, 3 H), 2.11-2.21 (m, 1 H), 1.85-2.00 (m, 1 H); MS (M + H)$^+$ = 365. |

TABLE 4-continued

Examples 51-66.

| Example | Starting Material | Reaction procedure | Resulting compound | NMR and MS |
|---|---|---|---|---|
| Example 61 | Product of Example 49B and 2-chloronicotinonitrile | Example 50 | (3aR,6aR)-2-{4-[4-(5-Methyl-hexahydro-pyrrolo[3,4-b]pyrrol-1-yl)-phenyl]-piperazin-1-yl}-nicotinonitrile | $^1$H NMR (300 MHz, CDCl$_3$) δ ppm 8.36 (dd, J = 4.75, 2.03 Hz, 1 H), 7.78 (dd, J = 7.80, 2.03 Hz, 1 H), 6.90-6.96 (m, 2 H), 6.76 (dd, J = 7.46, 4.75 Hz, 1 H), 6.53-6.59 (m, 2 H), 4.09-4.20 (m, 1 H), 3.85-3.92 (m, 4 H), 3.49-3.53 (m, 1 H), 3.21-3.25 (m, 1 H), 3.15-3.23 (m, 4 H), 2.99-3.05 (m, 1 H), 2.55-2.80 (m, 4 H), 2.40-2.45 (s, 3 H), 2.09-2.23 (m, 1 H), 1.88-2.01 (m, 1 H); MS (M + H)$^+$ = 389. |
| Example 62 | Product of Example 7B and 4-bromodiphenylmethane | Example 7C | (3aR,6aR)-1-(4-benzylphenyl)-5-methyloctahydropyrrolo[3,4-b]pyrrole | $^1$H NMR (300 MHz, CDCl$_3$) δ ppm 7.22-7.30 (m, 3 H), 7.12-7.20 (m, 2 H), 7.05 (d, J = 8.48 Hz, 2 H), 6.43-6.56 (m, 2 H), 4.17-4.25 (m, 1 H), 3.89 (s, 2 H), 3.46-3.57 (m, 1 H), 3.22-3.34 (m, 1 H), 3.01-3.15 (m, 2 H), 2.89-3.00 (m, 1 H), 2.73 (m, 2 H), 2.50 (s, 3 H), 2.08-2.24 (m, 1 H), 1.89-1.99 (m, 1 H); MS (M + H)$^+$ = 293. |
| Example 63 | Product of Example 7B and 4-bromobiphenylether | Example 7C | (3aR,6aR)-5-methyl-1-(4-phenoxyphenyl)octahydropyrrolo[3,4-b]pyrrole | $^1$H NMR (300 MHz, CDCl$_3$) δ ppm 7.25-7.31 (m, 2 H), 6.87-7.05 (m, 5 H), 6.51-6.61 (m, 2 H), 4.03-4.14 (m, 1 H), 3.45-3.56 (m, 1 H), 3.15-3.26 (m, 1 H), 2.90-3.00 (m, 1 H), 2.69-2.76 (m, 1 H), 2.50-2.63 (m, 3 H), 2.34 (s, 3 H), 2.13-2.22 (m, 1 H), 1.85-2.00 (m, 1 H); MS (M + H)$^+$ = 295. |
| Example 64 | Product of Example 7B and benzyl-4-bromophenylketone | Example 7C | 1-{4-[(3aR,6aR)-5-methylhexahydropyrrolo[3,4-b]pyrrol-1(2H)-yl]phenyl}-2-phenylethanone | $^1$H NMR (CDCl$_3$) δ ppm 7.93 (d, J = 8.82 Hz, 2 H), 7.20-7.34 (m, 5 H), 6.50 (d, J = 9.16 Hz, 2 H), 4.31-4.47 (m, 1 H), 4.19 (s, 2 H), 3.55-3.67 (m, 1 H), 3.39-3.52 (m, 1 H), 3.09-3.28 (m, 1 H), 2.44-2.89 (m, 4 H), 2.15-2.27 (m, 1 H), 2.09 (s, 3 H), 1.94-2.06 (m, 1 H); MS (M + H)$^+$ = 321. |
| Example 65 | Product of Example 49B and 4-bromophenylether | Example 49C | (3aR,6aR)-1-[4-(4-bromophenoxy)phenyl]-5-methyloctahydropyrrolo[3,4-b]pyrrole | $^1$H NMR (300 MHz, CDCl$_3$) δ ppm 7.32-7.39 (m, 2 H), 6.89-6.98 (m, 2 H), 6.75-6.84 (m, 2 H), 6.50-6.58 (m, 2 H), 4.14-4.20 (m, 1 H), 3.48-3.61 (m, 1 H), 3.24-3.30 (m, 1 H), 2.99-3.14 (m, 1 H), 2.62-2.86 (m, 4 H), 2.45 (s, 3 H), 2.13-2.23 (m, 1 H), 1.91-2.02 (m, 1 H); MS (M + H)$^+$ = 373/375. |
| Example 66 | Product of Example 65 and 4-cyanophenylboronic acid | Example 7D | 4'-{4-[(3aR,6aR)-5-methylhexahydropyrrolo[3,4-b]pyrrol-1(2H)-yl]phenoxy}-1,1'-biphenyl-4-carbonitrile | $^1$H NMR (300 MHz, CDCl$_3$) δ ppm 7.61-7.70 (m, 2 H), 7.47-7.53 (m, 2 H), 7.33-7.38 (m, 2 H), 6.89-6.94 (m, 2 H), 6.77-6.82 (m, 2 H), 6.52-6.57 (m, 2 H), 4.03-4.12 (m, 1 H), 3.47-3.55 (m, 1 H), 3.15-3.26 (m, 1 H), 2.90-3.01 (m, 1 H), 2.69-2.76 (m, 1 H), 2.50-2.64 (m, 3 H), 2.32-2.36 (m, 3 H), 2.12-2.24 (m, 1 H), 1.86-2.00 (m, 1 H)); MS (M + H)$^+$ = 396. |

Example 67

{4-[(3aR,6aR)-5-methylhexahydropyrrolo[3,4-b]pyrrol-1(2H)-yl]phenyl}(phenyl)methanone The product of Example 7B (35 mg, 0.28 mmole), 4-fluorobenzophenone (110 mg, 0.55 mmole) and triethylamine (200 μl, 1.43 mmole) were dissolved in 1 ml of acetonitrile and heated at 80° C. under N$_2$ for 3 days. The mixture was cooled to room temperature, diluted with water and extracted with dichloromethane (5×). The combined organics were dried over sodium sulfate, filtered, concentrated under reduced pressure and purified by chromatography (eluting with a mixture of 5% methanol and 0.5% ammonium hydroxide in dichloromethane) to provide the title compound. 1H NMR (CDCl$_3$) δ ppm 7.93 (d, J=8.82 Hz, 2H) 7.20-7.34 (m, 5H) 6.50 (d, J=9.16 Hz, 2H) 4.31-4.47 (m, 1H) 4.19 (s, 2H) 3.55-3.67 (m, 1H) 3.39-3.52 (m, 1H) 3.09-3.28 (m, 1H) 2.44-2.89 (m, 4H) 2.15-2.27 (m, 1H) 2.09 (s, 3H) 1.94-2.06 (m, 1H); MS (M+H)$^+$=307.

Example 68

4-[(3aR,6aR)-5-methylhexahydropyrrolo[3,4-b]pyrrol-1(2H)-yl]benzonitrile

The title compound was prepared according to the procedure described in Example 7C substituting 4-bromobenzonitrile for 1,4-dibromobenzene. $^1$H NMR (CDCl$_3$) δ ppm 7.45 (d, J=8.81 Hz, 2H) 6.51 (d, J=8.81 Hz, 2H) 4.16-4.28 (m, 1H)

3.47-3.62 (m, 1H) 3.31-3.44 (m, 1H) 2.95-3.13 (m, 1H) 2.68-2.81 (m, 2H) 2.55-2.67 (m, 2H) 2.36 (s, 3H) 2.12-2.27 (m, 1H) 1.93-2.09 (m, 1H); MS (M+H)$^+$=228.

Example 69

1-{4-[(3aR,6aR)-5-methylhexahydropyrrolo[3,4-b]pyrrol-1(2H)-yl]phenyl}methanamine The product of Example 68 (676 mg, 3.0 mmole) in 50 mL of 20% ammonia in methanol was stirred in the presence of 6.8 g Raney-Nickel under an atmosphere of hydrogen at 60 psi at room temperature for 4 hours. Catalyst was removed by filtration through CELITE® and the filtrate concentrated under reduced pressure. The resulting oil was purified by flash chromatography (eluting with a mixture of 5% basic methanol in dichloromethane) to provide the titled compound. $^1$H NMR (CDCl$_3$) δ ppm 7.17 (d, J=8.82 Hz, 2H) 6.55 (d, J=8.48 Hz, 2H) 4.07-4.16 (m, 1H) 3.77 (s, 2H) 3.45-3.59 (m, 1H) 3.16-3.28 (m, 1H) 2.88-3.04 (m, 1H) 2.63-2.74 (m, 2H) 2.53-2.63 (m, 2H) 2.34 (s, 3H) 2.08-2.23 (m, 1H) 1.86-2.05 (m, 1H); MS (M+H)$^+$=232.

Example 70

3-({4-[(3aR,6aR)-5-methylhexahydropyrrolo[3,4-b]pyrrol-1(2H)-yl]benzyl}amino)benzonitrile The product of Example 69 (40 mg, 0.173 mmole), 3-bromobenzonitrile (47 mg, 0.258 mmole), tris(dibenzylideneacetone)dipalladium (16 mg, 0.017 mmole), racemic-2,2'-bis(diphenylphosphino)-1,1'-binaphthyl (21 mg, 0.034 mmole) and cesium carbonate (85 mg, 0.26 mmole) were dissolved in 1 ml of toluene and heated at 100° C. under N$_2$ for 48 hours. The mixture was cooled to room temperature, diluted with water and extracted with dichloromethane (3×). The combined organics were dried over sodium sulfate, filtered, concentrated under reduced pressure and purified by chromatography (eluting with a mixture of 2% basic methanol in dichloromethane) to provide the title compound. $^1$H NMR (CDCl$_3$) δ ppm 9.73 (s, 1H) 7.72 (d, J=8.82 Hz, 2H) 7.30-7.54 (m, 2H) 7.14-7.22 (m, 1H) 6.77-6.88 (m, 1H) 6.56 (t, J=8.65 Hz, 2H) 4.22-4.33 (m, 1H) 4.19 (s, 2H) 3.36-3.64 (m, 2H) 2.90-3.08 (m, 1H) 2.66-2.79 (m, 2H) 2.52-2.63 (m, 2H) 2.32 (s, 3H) 2.09-2.26 (m, 1H) 1.87-2.04 (m, 1H); MS (M+H)$^+$=333.

The following compounds and Examples were made according to the procedures outlined above with the exception that different reagents were substituted to obtain the titled compounds.

Example 72

2-(5-{4-[(3aR,6aR)-5-Methylhexahydropyrrolo[3,4-b]pyrrol-1(2H)-yl]phenyl}pyridin-2-yl)pyridazin-3(2H)-one

Example 72A tert-Butyl(3aR,6aR)-1-(4-bromophenyl)hexahydropyrrolo[3,4-b]pyrrole-5(1H)-carboxylate tert-Butyl(3aR,6aR)-hexahydropyrrolo[3,4-b]pyrrole-5(1H)-carboxylate (1, 1.5 g, 7.0 mmol), 1,4-dibromobenzene (2.8 g, 20.4 mmol), Pd$_2$(dba)$_3$ (275 mg, 0.3 mmol), BINAP (375 mg, 0.6 mmol) and sodium tent-butoxide (1.93 g, 20.0 mmol) were placed in glass microwave tubes and then purged three times with N$_2$ gas, followed by the addition of toluene (45 mL). The mixture was heated to 140° C. for 15 minutes in a microwave reactor. The mixture was then cooled to room temperature, was filtered, and the crude mixture was purified via chromatography (SiO$_2$, 0-25% ethyl acetate:hexanes) to provide the title compound. $^1$H NMR (300 MHz, CDCl$_3$): δ=7.30 ppm (m, 2H), 7.39 (m, 2H), 4.11 (m, 1H), 3.57 (m, 3H), 3.31 (m, 3H), 2.99 (m, 1H), 2.15 (m, 1H), 1.92 (m, 1H), 1.43 (s, 9H). MS (ESI, M+1): 310.9.

Example 72B (3aR,6aR)-1-(4-Bromophenyl)-5-methyloctahydropyrrolo[3,4-b]pyrrole To a solution of (3aR,6aR)-tert-butyl 1-(4-bromophenyl)hexahydropyrrolo[3,4-b]pyrrole-5(1H)-carboxylate (1.86 g, 5.1 mmol) in CH$_2$Cl$_2$ (50 mL) at 23° C. was added TFA (8 mL) and the mixture was allowed to stir for 2 hrs. The solvents were removed under vacuum and the residue was taken up in MeOH (50 mL) followed by the addition of formaldehyde (37%, 3 mL, 40 mmol) and NaBH$_3$CN (950 mg, 15.1 mmol). The mixture was stirred at 23° C. for 10 hours, concentrated under reduced pressure and the residue was dissolved in CH$_2$Cl$_2$ (100 mL), washed sequentially with water (2×50 mL), brine (1×30 mL), and dried over Na$_2$SO$_4$, filtered and concentrated under reduced pressure. The crude product mixture was purified via chromatography (SiO$_2$, 0-10% MeOH in CH$_2$Cl$_2$) to provide the title compound. $^1$H NMR (300 MHz, CDCl$_3$): δ=7.28 ppm (m, 2H), 6.44 (m, 2H), 4.05 (m, 1H), 3.45 (m, 1H), 3.19 (m, 1H), 2.94 (m, 1H), 2.67 (m, 1H), 2.52 (m, 3H), 2.30 (s, 3H), 2.16 (m, 1H), 1.95 (m, 1H). MS (ESI, M+1): 280.8.

TABLE 5

Example 71.

| Example | Starting Material | Reaction procedure | Resulting compound | NMR and MS |
|---------|-------------------|--------------------|--------------------|------------|
| Example 71 | Product of Example 68B and 2-chloro-5-ethylpyrimidine | Example 68C | 5-ethyl-N-{4-[(3aR,6aR)-5-methylhexahydropyrrolo[3,4-b]pyrrol-1(2H)-yl]benzyl}pyrimidin-2-amine | $^1$H NMR (CDCl$_3$) δ ppm 8.15 (s, 2 H), 7.21 (d, J = 8.48 Hz, 2 H), 6.54 (d, J = 8.82 Hz, 2 H), 4.49 (d, J = 5.76 Hz, 2 H), 4.05-4.15 (m, 1 H), 3.67-3.85 (m, 1 H), 3.41-3.65 (m, 2 H), 3.13-3.29 (m, 1 H), 2.87-3.02 (m, 1 H), 2.61-2.73 (m, 1 H), 2.38-2.59 (m, 3 H), 2.32 (s, 3 H), 2.09-2.25 (m, 1 H), 1.86-2.03 (m, 1 H), 1.19 (t, J = 7.46 Hz, 3 H),; MS (M + H),$^+$ = 338. |

Example 72C (3aR,6aR)-5-Methyl-1-(4-(4,4,5,5-tetramethyl-1,3-dioxaborolan-2-yl)phenyl)octa-hydropyrrolo[3,4-b]pyrrole (3aR,6aR)-1-(4-Bromophenyl)-5-methyloctahydropyrrolo[3,4-b]pyrrole (1.0 g, 3.6 mmol), bis(pinacolato)diboron (4,4,4',4',5,5,5',5'-octamethyl-2,2'-bi(1,3,2-dioxaborolane, (1.0 g, 3.9 mmol), Pd(dppf)Cl$_2$.CH$_2$Cl$_2$ (100 mg, 0.12 mmol) and KOAc (1150 mg, 11.7 mmol) were placed in a sealed microwave reaction tube, and purged three times with N$_2$ gas. Dioxane (20 mL) was added, and the mixture was heated at 150° C. for 15 minutes. After cooling down to 23° C., the mixture was filtered, and solvent was removed under reduced pressure. The mixture was then purified via chromatography (SiO$_2$, 10-60% ethyl acetate in hexanes) to provide the title compound. $^1$H NMR (300 MHz, CDCl$_3$): δ=7.67 ppm (m, 2H), 6.54 (m, 2H), 4.21 (m, 1H), 3.52 (m, 1H), 3.33 (m, 1H), 2.97 (m, 1H), 2.67 (m, 2H), 2.57 (m, 2H), 2.34 (br, 3H), 2.15 (m, 1H), 1.95 (m, 1H), 1.32 (s, 12H). MS (ESI, M+1): 329.1.

Example 72D 2-(5-Bromopyridin-2-yl)pyridazin-3(2H)-one and 2-(6-bromopyridin-3-yl)pyridazin-3(2H)-one 3-Pyridazinone (300 mg, 3.1 mmol), 2,5-dibromopyridine (1.0 g, 4.2 mmol), copper powder (200 mg, 3.1 mmol) and K$_2$CO$_3$ (1.29 g, 9.3 mmol) were placed in a sealed microwave tube, and purged three times with N$_2$ gas, followed by the addition of pyridine (15 mL). The mixture was heated to 120° C. in a microwave reactor for 40 minutes. The mixture was concentrated under reduced pressure after which the residue was taken up in CH$_2$Cl$_2$/MeOH, filtered and concentrated under reduced pressure. The crude mixture was purified via chromatography (SiO2, 10-80% ethyl acetate in hexanes) to provide the title compounds.

2-(5-Bromopyridin-2-yl)pyridazin-3(2H)-one. $^1$H NMR (300 Mhz, CDCl$_3$): δ=8.72 ppm (s (br), 1H), 7.99 (m, 2H), 7.68 (d (br), J=8.4 Hz, 1H), 7.29 (dd (br), J=8.4, 3.7 Hz, 1H), 7.07 (dd, J=9.5, 1.7 Hz, 1H). MS (ESI, M+1): 253.8.

2-(6-Bromopyridin-3-yl)pyridazin-3(2H)-one. $^1$H NMR (300 MHz, CDCl$_3$): δ=8.76 ppm (d, J=3.4 Hz, 1H), 7.98 (dd, J=8.5, 2.7 Hz, 1H), 7.94 (dd, J=2.7, 1.7 Hz, 1H), 7.59 (d, J=8.4 Hz, 1H), 7.29 (dd, J=8.4, 3.4 Hz, 1H), 7.06 (dd, J=8.5, 1.7 Hz, 1H). MS (ESI, M+1): 253.8.

Example 72E 2-(5-(4-((3aR,6aS)-5-Methylhexahydropyrrolo[3,4-b]pyrrol-1(2H)-yl)phenyl)pyri-din-2-yl)pyridazin-3(2H)-one (3aR,6aR)-5-Methyl-1-(4-(4,4,5,5-tetramethyl-1,3-dioxaborolan-2-yl)phenyl)octa-hydro-pyrrolo[3,4-b]pyrrole (50 mg, 0.15 mmol), 2-(5-bromopyridin-2-yl)pyridazin-3(2H)-one (42 mg, 0.17 mmol), Pd(PPh$_3$)$_2$Cl$_2$ (11 mg, 0.01 mmol), 2-(dicyclohexylphosphino)biphenyl (5.6 mg, 0.016 mmol) and Na$_2$CO$_3$ (1M, 225 µL) were placed in a microwave tube, purged with N$_2$ and a mixture of solvents (EtOH:dioxane=1:1, 1 mL) was added. The mixture was heated to 140° C. in a microwave reactor for 15 minutes, cooled to ambient temperature, was filtered, and concentrated under reduced pressure. The residue was purified via chromatography (SiO$_2$, 0-10% MeOH in CH$_2$Cl$_2$) to provide the title compound. $^1$H NMR (300 MHz, CDCl$_3$): δ=8.82 ppm (d, J=2.8 Hz, 1H), 7.98 (m, 2H), 7.73 (d, J=8.2 Hz, 1H), 7.52 (m, 2H), 7.28 (dd, J=10.1, 3.7 Hz, 1H), 7.09 (dd, J=10.1, 1.7 Hz, 1H), 6.67 (m, 2H), 4.39 (m, 1H), 3.66 (m, 1H), 3.30 (m, 3H), 2.87 (m, 2H), 2.59 (s (br), 3H), 2.23 (m, 2H), 2.05 (m, 1H). MS (ESI, M+1): 374.2.

Example 73

2-(6-{4-[(3aR,6aR)-5-methylhexahydropyrrolo[3,4-b]pyrrol-1(2H)-yl]phenyl}pyridin-3-yl)pyridazin-3(2H)-one The title compound was prepared according to the procedure described in Example 72E, substituting 2-(5-bromopyridin-2-yl)pyridazin-3(2H)-one with 2-(6-bromopyridin-3-yl)pyridazin-3(2H)-one. $^1$H NMR (300 MHz, CDCl$_3$): δ=8.91 ppm (d, J=2.8 Hz, 1H), 8.02 (dd, J=8.8, 2.7 Hz, 1H), 7.94 (m, 3H), 7.73 (d, J=8.8 Hz, 1H), 7.27 (dd, J=9.5, 3.7 Hz, 1H), 7.08 (dd, J=9.5, 1.7 Hz, 1H), 6.65 (m, 2H), 4.33 (m, 1H), 3.62 (m, 1H), 3.43 (m, 1H), 3.15 (m, 1H), 2.83 (m, 2H), 2.70 (m, 2H), 2.47 (s (br), 3H), 2.22 (m, 1H), 2.03 (m, 1H). MS (ESI, M+1): 374.1.

Example 74

2-(5-{4-[(3aR,6aR)-5-methylhexahydropyrrolo[3,4-b]pyrrol-1(2H)-yl]phenyl}-1,3-thiazol-2-yl)pyridazin-3(2H)-one

Example 74A 2-(5-Bromothiazol-2-yl)pyridazin-3(2H)-one

The title compound was prepared according to the procedure described in Example 72D, substituting 2,5-dibromopyridine with 2,5-dibromothiazole. $^1$H NMR (300 MHz, CDCl$_3$): δ=8.20 ppm (s, 1H), 7.98 (dd, J=3.7, 1.7 Hz, 1H), 7.30 (dd, J=9.5, 3.7 Hz, 1H), 7.13 (dd, J=9.5, 1.7 Hz, 1H). MS (ESI, M+1): 259.8.

Example 74B 2-(5-(4-((3aR,6aR)-5-Methylhexahydropyrrolo[3,4-b]pyrrol-1(2H)-yl)phenyl)thia-zol-2-yl)pyridazin-3(2H)-one The title compound was prepared according to the procedure described in Example 72E, substituting 2-(5-bromopyridin-2-yl)pyridazin-3(2H)-one with 2-(5-bromothiazol-2-yl)pyridazin-3(2H)-one. $^1$H NMR (300 MHz, CDCl$_3$): δ=8.43 ppm (s, 1H), 7.95 (dd, J=4.0, 1.7 Hz, 1H), 7.84 (m, 2H), 7.25 (dd, J=9.5, 4.0 Hz, 1H), 7.10 (dd, J=9.5, 1.7 Hz, 1H), 6.59 (m, 2H), 4.26 (m, 1H), 3.58 (m, 1H), 3.40 (m, 1H), 3.05 (m, 1H), 2.77 (m, 2H), 2.65 (m, 2H), 2.39 (s (br), 3H), 2.19 (m, 1H), 2.00 (m, 1H). MS (ESI, M+1): 380.1.

Example 75

5-(4-{4-[(3aR,6aR)-5-methylhexahydropyrrolo[3,4-b]pyrrol-1(2H)-yl]phenyl}piperazin-1-yl)pyridine-2-carbonitrile

Example 75A (3aR,6aR)-5-Methyl-1-(4-piperazin-1-yl-phenyl)-octahydro-pyrrolo[3,4-b]pyrrole The product of Example 72B (200 mg, 0.71 mmole), piperazine (200 mg, 2.33 mmole), tris(dibenzylideneacetone)

dipalladium (20 mg, 0.022 mmole), (R)-(+)-2,2'-bis(diphenylphosphino)-1,1'-binaphthyl (28 mg, 0.045 mmole), sodium tert-butoxide (140 mg, 1.46 mmole) and 7 ml of toluene were mixed under $N_2$ in a Emrys process vial. The vial was sealed heated in the microwave for 15 minutes at 140° C. using the Emrys Creator. The mixture was diluted with Water and extracted with dichloromethane (4×). The combined organic layers were washed with brine, dried over sodium sulfate, filtered, and concentrated under reduced pressure to give the crude product which was purified by column chromatography (10% methanol and 1% ammonium hydroxide in dichloromethane) to provide the title compound. $^1$H NMR (300 MHz, CDCl$_3$) δ ppm 6.84-6.94 (m, 2H) 6.53-6.60 (m, 2H) 4.00-4.07 (m, 1H) 3.44-3.51 (m, 1H) 3.11-3.20 (m, 1H) 2.99-3.09 (m, 9H) 2.88-2.96 (m, 1H) 2.68 (dd, J=9.66, 2.54 Hz, 1H) 2.48-2.59 (m, 2H) 2.31 (s, 3H) 2.09-2.19 (m, 1H) 1.89 (m, 1H). MS: (M+H)$^+$=287.

Example 75B 5-(4-(4-(3aR,6aR)-5-methylhexahydropyrrolo[3,4-b]pyrrol-1(2H)-yl)phenyl)piperazin-1-yl)picolinonitrile The product of Example 75A (78.0 mg, 0.27 mmole), 5-bromo-2-cyanopyridine (74.8 mg, 0.41 mmole), palladium acetate (2.5 mg, 0.011 mmole), 4,5-bis(diphenylphosphino)-9,9-dimethylxanthene (19.0 mg, 0.037 mmole), cesium carbonate (142.1 mg, 0.44 mmole) and 3 ml of tetrahydrofuran were mixed under $N_2$ in a Emrys process vial. The vial was sealed and heated in the microwave for 2 hours at 120° C. using the Emrys Creator. The mixture was diluted with water and extracted with dichloromethane (4×). The combined organic layers were washed with brine, dried over sodium sulfate, filtered, and concentrated under reduced pressure to give the crude product which was purified by column chromatography (10% methanol and 1% ammonium hydroxide in dichloromethane) to provide the title compound. $^1$H NMR (300 MHz, CDCl$_3$) δ ppm 8.36 (d, J=2.71 Hz, 1H) 7.53 (d, J=8.82 Hz, 1H) 7.13 (dd, J=8.82, 3.05 Hz, 1H) 6.86-6.98 (m, 2H) 6.50-6.65 (m, 2H) 4.06 (t, J=8.65 Hz, 1H) 3.44-3.59 (m, 5H) 3.11-3.24 (m, 5H) 2.88-3.02 (m, 1H) 2.56-2.72 (m, 4H) 2.33 (s, 3H) 2.06-2.24 (m, 1H) 1.83-2.01 (m, 1H). MS: (M+H)$^+$=389.

Example 76

(3aR,6aR)-1-[4'-(2-methoxypyrimidin-5-yl)-1,1'-biphenyl-4-yl]-5-methyloctahydropyrrolo[3,4-b]pyrrole The title compound was prepared according to the procedure described in Example 7D, substituting the product of Example 41A for the product of Example 7C and substituting 2-methoxy-pyrimidine-5-boronic acid for 4-cyanophenylboronic acid. $^1$H NMR (500 MHz, CDCl$_3$) δ ppm 8.76 (s, 2H) 7.66 (d, J=8.54 Hz, 2H) 7.53 (dd, J=11.75, 8.70 Hz, 4H) 6.67 (d, J=8.85 Hz, 2H) 4.13-4.22 (m, 1H) 4.07 (s, 3H) 3.53-3.61 (m, 1H) 3.26-3.35 (m, 1H) 2.91-3.03 (m, 1H) 2.71-2.77 (m, 1H) 2.48-2.67 (m, 3H) 2.33 (s, 3H) 2.13-2.25 (m, 1H) 1.90-2.01 (m, 1H). MS: (M+H)$^+$=387.

Example 77

5-{4'-[(3aR,6aR)-5-methylhexahydropyrrolo[3,4-b]pyrrol-1(2H)-yl]-1,1'-biphenyl-4-yl}pyridine-2-carbonitrile The title compound was prepared according to the procedure described in Example 7D, substituting the product of Example 41A for the product of Example 7C and substituting 5-(4,4,5,5-tetramethyl-1,3,2-dioxaborolan-2-yl)picolinonitrile for 4-cyanophenylboronic acid. $^1$H NMR (500 MHz, CDCl$_3$) δ ppm 8.99 (d, J=2.14 Hz, 1H) 8.03 (dd, J=8.09, 2.29 Hz, 1H) 7.76 (d, J=7.93 Hz, 1H) 7.68-7.73 (m, 2H) 7.59-7.67 (m, 2H) 7.52-7.58 (m, 2H) 6.67 (d, J=8.85 Hz, 2H) 4.12-4.23 (m, 3.05 Hz, 1H) 3.53-3.62 (m, 1H) 3.26-3.35 (m, 1H) 2.92-3.03 (m, 1H) 2.69-2.78 (m, 1H) 2.48-2.67 (m, 3H) 2.33 (s, 3H) 2.13-2.25 (m, 1H) 1.91-2.03 (m, 1H).

Example 78

6-methyl-2-{4'-[(3aR,6aR)-5-methylhexahydropyrrolo[3,4-b]pyrrol-1(2H)-yl]-1,1'-biphenyl-4-yl}pyridazin-3(2H)-one The title compound was prepared according to the procedure described in Example 41B, substituting 6-methyl-3(2H)-pyridazinone for 3(2H)-pyridazinone. $^1$H NMR (400 MHz, CDCl$_3$) δ ppm 7.61 (d, J=1.53 Hz, 4H) 7.49 (d, J=8.59 Hz, 2H) 7.14 (d, J=9.51 Hz, 1H) 6.99 (d, J=9.51 Hz, 1H) 6.65 (d, J=8.90 Hz, 2H) 4.13-4.21 (m, 1H) 3.50-3.61 (m, 1H) 3.25-3.35 (m, 1H) 2.89-3.01 (m, 1H) 2.69-2.77 (m, 1H) 2.50-2.68 (m, 3H) 2.40 (s, 3H) 2.32 (s, 3H) 2.11-2.26 (m, 1H) 1.89-2.01 (m, 1H). MS: (M+H)$^+$=387.

Example 79

(3aR,6aR)-5-methyl-1-[4'-(1-methyl-1H-pyrazol-4-yl)-1,1'-biphenyl-4-yl]octahydropyrrolo[3,4-b]pyrrole The title compound was prepared according to the procedure described in Example 7D, substituting the product of Example 41A for the product of Example 7C and substituting 1-methyl-4-(4,4,5,5-tetramethyl-1,3,2-dioxaborolan-2-yl)-1H-pyrazole for 4-cyanophenylboronic acid. $^1$H NMR (300 MHz, CDCl$_3$) δ ppm 7.78 (s, 1H) 7.62 (s, 1H) 7.45-7.60 (m, 6H) 6.65 (d, J=8.82 Hz, 2H) 4.11-4.21 (m, 1H) 3.95 (s, 3H) 3.50-3.61 (m, 1H) 3.23-3.35 (m, 1H) 2.90-3.05 (m, 1H) 2.69-2.77 (m, 1H) 2.50-2.69 (m, 3H) 2.33 (s, 3H) 2.11-2.26 (m, 1H) 1.88-2.02 (m, 1H). MS: (M+H)$^+$=359.

Example 80

(3aR,6aR)-1-[4'-(3,5-dimethyl-1H-pyrazol-4-yl)-1,1'-biphenyl-4-yl]-5-methyloctahydropyrrolo[3,4-b]pyrrole The title compound was prepared according to the procedure described in Example 7D, substituting the product of Example 41A for the product of Example 7C and substituting 3,5-dimethyl-4-(4,4,5,5-tetramethyl-1,3,2-dioxaborolan-2-yl)-1H-pyrazole for 4-cyanophenylboronic acid. $^1$H NMR (300 MHz, CDCl$_3$) δ ppm 7.59 (d, J=8.14 Hz, 2H) 7.52 (d, J=8.82 Hz, 2H) 7.30 (d, J=8.14 Hz, 2H) 6.66 (d, J=8.82 Hz, 2H) 4.11-4.23 (m, 1H) 3.51-3.62 (m, 1H) 3.24-3.36 (m, 1H) 2.88-3.04 (m, 1H) 2.70-2.79 (m, 1H) 2.49-2.66 (m, 3H) 2.33 (s, 9H) 2.10-2.25 (m, 1H) 1.90-2.03 (m, 1H). MS: (M+H)$^+$=373.

Example 81

(3aR,6aR)-1-(4'-(1H-pyrazol-4-yl)biphenyl-4-yl)-5-methyloctahydropyrrolo[3,4-b]pyrrole

Example 81A (3aR,6aR)-5-methyl-1-(4'-(1-trityl-1H-pyrazol-4-yl)biphenyl-4-yl)octahydropyrrolo[3,4-b]pyrrole The title compound was prepared according to the procedure described in Example 7D, substituting the product of Example 41A for the product of Example 7C and substituting 4-(4,4,5,5-tetramethyl-1,3,2-dioxaborolan-2-yl)-1-trityl-1H-pyrazole for 4-cyanophenylboronic acid. $^1$H NMR (300 MHz, CDCl$_3$) δ ppm 7.96 (s, 1H) 7.63 (s, 1H) 7.42-7.54 (m, 6H) 7.29-7.37 (m, 9H) 7.17-7.24 (m, 6H) 6.64 (d, J=8.82 Hz, 2H) 4.11-4.23 (m, 1H) 3.49-3.61 (m, 1H) 3.23-3.35 (m, 1H) 2.91-3.03 (m, 1H) 2.66-2.78 (m, 1H) 2.51-2.66 (m, 3H) 2.33 (s, 3H) 2.12-2.24 (m, 1H) 1.92-2.01 (m, 1H). MS: (M+H)$^+$=586.

Example 81B (3aR,6aR)-1-(4'-(1H-pyrazol-4-yl)biphenyl-4-yl)-5-methyloctahydropyrrolo[3,4-b]pyrrole The product of Example 81A (44 mg, 0.075 mmole) was stirred with 3 ml of formic acid for 4 hours. The mixture was concentrated to dryness and the residue was dissolved in 10% methanol in dichloromethane and stirred with saturated sodium bicarbonate. Two layers were separated and the aqueous layer was extracted with dichloromethane (2×). The combined organic layers were dried over sodium sulfate, filtered, and concentrated under reduced pressure. The residue was purified by column chromatography to provide the title compound. $^1$H NMR (300 MHz, CDCl$_3$) δ ppm 7.88 (s, 2H) 7.47-7.64 (m, 6H) 6.65 (d, J=8.81 Hz, 2H) 4.11-4.25 (m, 1H) 3.50-3.66 (m, 1H) 3.25-3.37 (m, 1H) 2.92-3.07 (m, 1H) 2.71-2.82 (m, 1H) 2.51-2.69 (m, 3H) 2.34 (s, 3H) 2.13-2.25 (m, 1H) 1.90-2.05 (m, 1H). MS: (M+H)$^+$=345.

Example 82

3-methyl-1-{4'-[(3aR,6aR)-5-methylhexahydropyrrolo[3,4-b]pyrrol-1(2H)-yl]-1,1'-biphenyl-4-yl}pyridin-2(1H)-one The title compound was prepared according to the procedure described in Example 41B, substituting 3-methylpyridin-2(1H)-one for 3(2H)-pyridazinone. $^1$H NMR (500 MHz, CDCl$_3$) δ ppm 7.62 (d, J=8.54 Hz, 2H) 7.49 (d, J=8.85 Hz, 2H) 7.39 (d, J=8.54 Hz, 2H) 7.26-7.29 (m, 2H) 6.65 (d, J=8.85 Hz, 2H) 6.14-6.20 (m, 1H) 4.13-4.20 (m, 1H) 3.53-3.60 (m, 1H) 3.26-3.34 (m, 1H) 2.90-3.03 (m, 1H) 2.70-2.76 (m, 1H) 2.50-2.66 (m, 3H) 2.33 (s, 3H) 2.20 (s, 3H) 2.14-2.20 (m, 1H) 1.91-2.01 (m, 1H). MS: (M+H)$^+$=386.

Example 83

5-methyl-1-{4'-[(3aR,6aR)-5-methylhexahydropyrrolo[3,4-b]pyrrol-1(2H)-yl]-1,1'-biphenyl-4-yl}pyridin-2(1H)-one The title compound was prepared according to the procedure described in Example 41B, substituting 5-methylpyridin-2(1H)-one for 3(2H)-pyridazinone. $^1$H NMR (500 MHz, CDCl$_3$) δ ppm 7.62 (d, J=8.59 Hz, 2H) 7.48 (d, J=8.59 Hz, 2H) 7.38 (d, J=8.29 Hz, 2H) 7.31 (dd, J=9.21, 2.45 Hz, 2H) 7.15 (s, 1H) 6.65 (d, J=8.90 Hz, 2H) 4.14-4.21 (m, 1H) 3.51-3.60 (m, 1H) 3.26-3.36 (m, 1H) 2.92-3.03 (m, 1H) 2.70-2.77 (m, 1H) 2.51-2.69 (m, 3H) 2.33 (s, 3H) 2.15-2.26 (m, 1H) 2.11 (s, 3H) 1.90-2.01 (m, 1H), MS: (M+H)$^+$=386.

Example 84

6-methyl-1-{4'-[(3aR,6aR)-5-methylhexahydropyrrolo[3,4-b]pyrrol-1(2H)-yl]-1,1'-biphenyl-4-yl}pyridin-2(1H)-one The title compound was prepared according to the procedure described in Example 41B, substituting 6-methylpyridin-2(1H)-one for 3(2H)-pyridazinone. $^1$H NMR (400 MHz, CDCl$_3$) δ ppm 7.67 (d, J=2.76 Hz, 2H) 7.45-7.57 (m, 4H) 7.25-7.34 (m, 2H) 7.20 (d, J=8.29 Hz, 1H) 6.63-6.69 (m, 2H) 4.13-4.22 (m, 1H) 3.50-3.62 (m, 1H) 3.26-3.36 (m, 1H) 2.90-3.03 (m, 1H) 2.70-2.78 (m, 1H) 2.48-2.66 (m, 3H) 2.32 (s, 3H) 2.12-2.25 (m, 1H) 2.04 (s, 3H) 1.89-2.00 (m, 1H), MS: (M+H)$^+$=386.

Example 85

2-{4'-[(3aR,6aR)-5-ethylhexahydropyrrolo[3,4-b]pyrrol-1(2H)-yl]-1,1'-biphenyl-4-yl}pyridazin-3(2H)-one

Example 85A (3aR,6aR)-ethyl 1-(4'-(6-oxopyridazin-1(6H)-yl)biphenyl-4-yl)hexahydropyrrolo[3,4-b]pyrrole-5(1H)-carboxylate 2-(4'-Bromobiphenyl-4-yl)pyridazin-3(2H)-one (1.92 g, 5.86 mmol), palladium(II) acetate (0.158 g, 0.234 mmol), 9,9-dimethyl-4,5-bis(diphenylphosphino)xanthene (0.407 g, 0.703 mmol) and cesium carbonate (3.06 g, 9.38 mmol) were suspended in 25 mL of THF. A solution of (3aR,6aR)-ethyl hexahydropyrrolo[3,4-b]pyrrole-5(1H)-carboxylate in 10 mL of THF was added and the mixture was heated at 70° C. under N$_2$ for 20 hours. The mixture was allowed to cool to ambient temperature, diluted with 70 mL of EtOAc, and filtered through a ¼" pad of Celite®. The Celite® pad was washed with an additional 70 mL of EtOAc and the filtrate was absorbed on silica gel and chromatographed (eluting with 0-40% EtOAc in DCM) to provide the title compound. $^1$H NMR (300 MHz, CDCl$_3$) δ ppm 7.91 (dd, J=3.7, 1.7 Hz, 1H), 7.64 (s, 4H), 7.53 (d, J=8.8 Hz, 2H), 7.25 (dd, J=9.8, 3.4 Hz, 1H), 7.07 (dd, J=9.5, 1.7 Hz, 1H), 6.64 (d, J=8.5 Hz, 2H), 4.20-4.32 (m, 1H), 4.12 (q, J=7.5 Hz, 2H), 3.70-3.81 (m, 1H), 3.59-3.69 (m, 2H), 3.48-3.58 (m, 1H), 3.36-3.48 (m, 2H), 2.99-3.10 (m, 1H), 2.20 (ddd, J=13.0, 7.3 Hz, 1H), 1.95 (ddd, J=12.9, 6.4 Hz, 1H), 1.24 (t, J=7.1 Hz, 3H). MS (ESI+) m/z 431 (M+H)$^+$.

Example 85B 2-(4'-((3aR,6aR)-hexahydropyrrolo[3,4-b]pyrrol-1(2H)-yl)biphenyl-4-yl)pyridazin-3(2H)-one The product from Example 85A (0.110 g, 0.256 mmol) was dissolved in 3 mL of a 1:1 mixture of HOAc and 12 M aqueous HCl, and heated at 100° C. for 16 hours in a sealed vessel. The mixture was cooled to 0° C., diluted with 15 mL of water, and the pH was adjusted to ~10 by the dropwise addition of 20% (w/v) aqueous KOH. The mixture was extracted three times with 25 mL of 5% n-propanol in CHCl$_3$ and the combined extracts were dried over Na$_2$SO$_4$, filtered, and absorbed on silica gel. The crude material was chromatographed, eluting with 0-5% aqueous NH$_4$OH in MeCN/MeOH (9:1), to provide the title compound. $^1$H NMR (300 MHz, CDCl$_3$) δ ppm 7.91 (dd, J=3.7, 1.7 Hz, 1H), 7.64 (s, 4H), 7.52 (d, J=8.8 Hz, 2H), 7.21-7.27 (m, 1H), 7.07 (dd, J=9.5, 1.7 Hz, 1H), 6.65 (d, J=8.8 Hz, 2H), 4.10-4.19 (m, 1H), 3.56-3.67 (m, 1H), 3.23-3.35 (m, 1H), 2.91-3.22 (m, 5H), 2.15-2.32 (m, 1H), 2.12 (br s, 1H), 1.87 (ddd, J=12.9, 7.5 Hz, 1H). MS (ESI+) m/z 359 (M+H)$^+$.

Example 85C 2-(4'-((3aR,6aR)-5-ethylhexahydropyrrolo[3,4-b]pyrrol-1(2H)-yl)biphenyl-4-yl)pyridazin-3(2H)-one The product from Example 85B (0.050 g, 0.140 mmol) and acetaldehyde (10.0 μL, 0.140 mmol) were combined in 5 mL of dichloroethane containing 3 drops of HOAc and stirred at ambient temperature for 10 minutes. Sodium triacetoxyborohydride (0.039 g, 0.182 mmol) was added and the mixture was stirred for 3 hours. The mixture was diluted with 20 mL of aqueous NaHCO$_3$ and extracted three times with 25 mL of 5% n-propanol in CHCl$_3$ and the combined extracts were dried over Na$_2$SO$_4$, filtered, and absorbed on silica gel. The crude material was chromatographed, eluting with 1% aqueous NH$_4$OH in EtOAc/MeOH (9:1), to provide the title compound. $^1$H NMR (300 MHz, CDCl$_3$) δ ppm 7.91 (d, J=2.0 Hz, 1H), 7.63 (s, 4H), 7.50 (d, J=8.5 Hz, 2H), 7.23 (d, J=3.7 Hz, 1H), 7.07 (d, J=9.2 Hz, 1H), 6.65 (d, J=8.8 Hz, 2H), 4.11-4.25 (m, 1H), 3.47-3.60 (m, 1H), 3.24-3.39 (m, 1H), 2.88-3.05 (m, 1H), 2.78 (dd, J=9.5, 6.4 Hz, 1H), 2.56-2.70 (m, 2H), 2.35-2.56 (m, 3H), 2.10-2.25 (m, 1H), 1.85-2.02 (m, 1H), 1.26 (s, 1H), 1.09 (t, J=7.1 Hz, 2H). MS (ESI+) m/z 387 (M+H)$^+$.

Example 86

2-{4'-[(3aR,6aR)-5-cyclobutylhexahydropyrrolo[3,4-b]pyrrol-1(2H)-yl]-1,1'-biphenyl-4-yl}pyridazin-3(2H)-one The product from Example 85B (0.033 g, 0.092 mmol), cyclobutanone (8.00 μL, 0.101 mmol), and sodium triacetoxyborohydride (0.025 g, 0.0.120 mmol) were processed as described in Example 85C to provide the title compound. $^1$H NMR (300 MHz, CDCl$_3$) δ ppm 7.91 (d, J=1.7 Hz, 1H), 7.63 (s, 4H), 7.50 (d, J=8.5 Hz, 2H), 7.23 (d, J=3.7 Hz, 1H), 7.07 (d, J=8.8 Hz, 1H), 6.65 (d, J=8.5 Hz, 2H), 4.13-4.24 (m, 1H), 3.52 (q, 1H), 3.32 (q, J=7.3 Hz, 1H), 2.74-3.04 (m, 3H), 2.63 (t, 1H), 2.46 (dd, J=9.3, 2.2 Hz, 1H), 2.35 (dd, J=8.8, 4.4 Hz, 1H), 2.06-2.23 (m, 1H), 1.82-2.05 (m, 4H), 1.60-1.80 (m, 3H). MS (ESI+) m/z 413 (M+H)$^+$.

Example 87

2-{4'-[(3aR,6aR)-5-Methylhexahydropyrrolo[3,4-b]pyrrol-1(2H)-yl]biphenyl-4-yl}-4,5-dihydropyridazin-3(2H)-one Flash chromatographic purification of a 7.38 g sample of 2-(4'-bromobiphenyl-4-yl)pyridazin-3(2H)-one (silica gel, gradient from 1 to 3% methanol in dichloromethane) yielded 100 mg of 2-(4'-bromobiphenyl-4-yl)-4,5-dihydropyridazin-3(2H)-one.

A small pressure tube equipped with a magnetic stir bar was charged with 100 mg of 2-(4'-bromobiphenyl-4-yl)-4,5-dihydropyridazin-3(2H)-one, 58 mg of (3aR,6aR)-5-methylhexahydropyrrolo[3,4-b]pyrrole dihydrochloride, 350 mg of cesium carbonate, 15 mg of silver triflate, 4.2 mg of tris(dibenzylideneacetone)dipalladium, and 7.2 mg of 2-dicyclohexylphosphino-2'(N,N-dimethylamino)biphenyl and 2 ml of toluene. After sealing and purging with argon the tube was heated at 100° C. for 20 hours. Crude product was purified by flash chromatography (silica gel, gradient 2 to 10% methanol in dichloromethane), which yielded 17 mg of the title compound as a dark yellow oil. Mass spectroscopy gave (M+H)$^+$ m/z 375.2, consistent with assigned structure.

Determination of Biological Activity

To determine the effectiveness of representative compounds of this invention as histamine-3 receptor ligands (H$_3$ receptor ligands), the following tests were conducted according to previously described methods (see European Journal of Pharmacology, 188:219-227 (1990); Journal of Pharmacology and Experimental Therapeutics, 275:598-604 (1995); Journal of Pharmacology and Experimental Therapeutics, 276:1009-1015 (1996); and Biochemical Pharmacology, 22:3099-3108 (1973)).

The rat H$_3$ receptor was cloned and expressed in cells, and competition binding assays carried out, according to methods previously described (see Esbenshade, et al. Journal of Pharmacology and Experimental Therapeutics, vol. 313:165-175, 2005; Esbenshade et al., Biochemical Pharmacology 68 (2004) 933-945; Krueger, et al. Journal of Pharmacology and Experimental Therapeutics, vol. 314:271-281, 2005. Membranes were prepared from C6 or HEK293 cells, expressing the rat histamine H$_3$ receptor, by homogenization on ice in TE buffer (50 mM Tris-HCl buffer, pH 7.4, containing 5 mM EDTA), 1 mM benzamidine, 2 μg/ml aprotinin, 1 μg/ml leupeptin, and 1 μg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer.

Membrane preparations were incubated with [$^3$H]-N-α-methylhistamine (0.5-1.0 nM) in the presence or absence of increasing concentrations of ligands for H$_3$ receptor competition binding. The binding incubations were conducted in a final volume of 0.5 ml TE buffer at 25° C. and were terminated after 30 minutes. Thioperamide (30 μM) was used to define non-specific binding. All binding reactions were terminated by filtration under vacuum onto polyethylenimine (0.3%) presoaked Unifilters (Perkin Elmer Life Sciences) or Whatman GF/B filters followed by three brief washes with 2 ml of ice-cold TE buffer. Bound radiolabel was determined by liquid scintillation counting. For all of the radioligand competition binding assays, IC$_{50}$ values and Hill slopes were determined by Hill transformation of the data and pK$_i$ values were determined by the Cheng-Prusoff equation.

Generally, representative compounds of the invention demonstrated binding affinities in the above assay from about 0.5 nM to about 500 nM. Preferred compounds of the invention bound to histamine-3 receptors with binding affinities from about 0.5 nM to about 100 nM. More preferred compounds of the invention bound to histamine-3 receptors with binding affinities from about 0.5 nM to about 20 nM.

In addition to the utility of in vitro methods for characterizing the H$_3$ binding affinity of compounds, there are animal models of human disease available which demonstrate the utility of compounds of the invention for treating human disease.

One animal model of the human disease ADHD (attention deficit hyperactivity disorder) and related human disorders of attention is an inhibitory avoidance test in SHR rat pups (a Spontaneously Hypertensive strain of rat pups). This model has also been alternatively termed a PAR (passive avoidance response) model. The methodology and utility of this test has been described in the literature, for example in Komater, V. A., et al. Psychopharmacology (Berlin, Germany) (2003), 167(4), 363-372; in "Two novel and selective nonimidazole $H_3$ receptor antagonists A-304121 and A-317920: II. In vivo behavioral and neurophysiological characterization." Fox, G. B., et al. Journal of pharmacology and experimental therapeutics (2003), 305(3), 897-908; in Cowart, et al. *J. Med. Chem.* 2005, 48, 38-55; in Fox, G. B., et al. "Pharmacological Properties of ABT-239: II. Neurophysiological Characterization and Broad Preclinical Efficacy in Cognition and Schizophrenia of a Potent and Selective Histamine $H_3$ Receptor Antagonist", Journal of Pharmacology and Experimental Therapeutics (2005) 313, 176-190; in "Effects of histamine $H_3$ receptor ligands GT-2331 and ciproxifan in a repeated acquisition avoidance response in the spontaneously hypertensive rat pup." Fox, G. B., et al. Behavioural Brain Research (2002), 131(1,2), 151-161. Representative compounds are active in this model, with preferred compounds of the invention active in the model at doses of ranging about 0.001-0.1 mg/kg of body weight.

Compounds of the invention are histamine-3 receptor ligands that modulate function of the histamine-3 receptor by altering the activity of the receptor. These compounds may be inverse agonists that inhibit the basal activity of the receptor or they may be antagonists that block the action of receptor-activating agonists.

Preparation of Salts and Polymorphs

Example A

2-{4'-[(3aR,6aR)-5-methylhexahydropyrrolo[3,4-b]pyrrol-1(2H)-yl]-1,1'-biphenyl-4-yl}pyridazin-3(2H)-one HCl salt hydrate 2-{4'-[(3aR,6aR)-5-Methylhexahydropyrrolo[3,4-b]pyrrol-1(2H)-yl]-1,1'-biphenyl-4-yl}pyridazin-3(2H)-one (745 mg) was suspended in dichloromethane (2.4 mL). The suspension was heated to about 35° C. A solution of HCl in methanol/water mixture was prepared by mixing 2.2 ml of 1 M HCl (in MeOH) with 0.6 ml water. The HCl solution was added to the suspension in dichloromethane dropwise. Throughout the process the suspension is stirred using a magnetic stirrer. The solid completely dissolved when about half of the HCl solution was added, yielded a clear solution. The solution was let cool to ambient temperatures naturally. Crystallization was observed during the cooling process. The resulting suspension was agitated at ambient temperatures overnight before the crystals were harvested.

Example B

2-{4'-[(3aR,6aR)-5-Methylhexahydropyrrolo[3,4-b]pyrrol-1(2H)-yl]-1,1'-biphenyl-4-yl}pyridazin-3(2H)-one HCl anhydrate 2-{4'-[(3aR,6aR)-5-Methylhexahydropyrrolo[3,4-b]pyrrol-1(2H)-yl]-1,1'-biphenyl-4-yl}pyridazin-3(2H)-one (226 mg) was suspended in methanol (4.0 mL). A solution of 1 M HCl in methanol (0.66 mL) was added to the suspension dropwise. Throughout the process the suspension is stirred using a magnetic stirrer. Most of the solid dissolved leaving a light suspension. Upon sonication, crystallization was observed. The resulting suspension was agitated at ambient temperatures overnight before the crystals were harvested.

Example C

2-{4'-[(3aR,6aR)-5-Methylhexahydropyrrolo[3,4-b]pyrrol-1(2H)-yl]-1,1'-biphenyl-4-yl}pyridazin-3(2H)-one HCl anhydrate 2-{4'-[(3aR,6aR)-5-Methylhexahydropyrrolo[3,4-b]pyrrol-1(2H)-yl]-1,1'-biphenyl-4-yl}pyridazin-3(2H)-one (372 mg) was suspended in dichloromethane (1.5 mL). The suspension was heated to about 50° C. A 1 M HCl (1.1 mL) solution was added to the suspension in dichloromethane dropwise. Throughout the process the suspension is stirred using a magnetic stirrer and temperature maintained at about 50° C. Most of the solid dissolved leaving a light suspension when about one third of the HCl solution was added. Upon further addition of the HCl solution, crystallization was observed. The resulting suspension was agitated at ambient temperatures overnight before the crystals were harvested.

Example D

Single crystal of 2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate salt monohydrate (Form A)

2-{4'-[(3aR,6aR)-5-Methylhexahydropyrrolo[3,4-b]pyrrol-1(2H)-yl]-1,1'-biphenyl-4-yl}pyridazin-3(2H)-one tartrate (Form A) was suspended in 1 mL of solution mixture, which was prepared by mixing 3.0 mL of dichloromethane with 1.5 mL of 20% water (in methanol). The suspension was vortexed and heated in a shaking water bath to about 40° C. and maintained for 1.5 hrs. It was further heated to about 70° C. The suspension was then filtered. The water bath was turned off, and the supernatant cooled to ambient temperatures naturally in the water bath. Single crystals were offered.

Example E

Single crystal of 2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate salt monohydrate (Form B)

2-{4'-[(3aR,6aR)-5-Methylhexahydropyrrolo[3,4-b]pyrrol-1(2H)-yl]-1,1'-biphenyl-4-yl}pyridazin-3(2H)-one tartrate (Form A) was suspended in 1 mL of solution mixture, which was prepared by mixing 5.0 mL of dichloromethane with 5.0 mL of 20% water (in methanol). The suspension was vortexed and heated to about 48° C. yielding a clear solution. The solution was then filtered and the supernatant cooled to ambient temperatures naturally overnight. The solids precipitated over the night were dissolved again the next day by heating the suspension to about 90° C. The solution was cooled slowly by progressively lowering the temperature of the water bath to ambient temperatures. Single crystals were offered.

Example F

Crystallization of Form B of L-tartrate salt of 2-{4'-[(3aR,6aR)-5-Methylhexahydropyrrolo[3,4-b]pyrrol-1(2H)-yl]-1,1'-biphenyl-4-yl}pyridazin-3(2H)-one 2-{4'-[(3aR,6aR)-5-Methylhexahydropyrrolo[3,4-b]pyrrol-1(2H)-yl]-1,1'-biphenyl-4-yl}pyridazin-3(2H)-one (free base, 1.74 g) was dissolved in 25 mLs of dimethyl acetamide by heating to 75° C. in a 50 mL jacketed reactor equipped with overhead stirring motor. A solution of L-tartaric acid in water was prepared by dissolving 850 mg of L-tartaric acid in 15 mL of de-ionized water by mixing at 25+/−5% ° C. The L-tartaric acid solution was slowly added to the hot free base solution, while maintaining the temperature of the free base solution at 75° C. Once all the L-tartaric acid solution had been, the reactor was cooled to 20° C. at 12° C./hour. Once the reactor reached 20° C., a sample was collected from the reactor for PXRD. The reactor was stirred for another 72 hours. The slurry was discharged onto a medium frit sintered glass filtration funnel. The reactor was rinsed with 20 mL of de-ionized water and the rinse was used to wash the cake. Solids were air-dried on the filter for 3 hours. PXRD analysis on the solids was collected after at 20° C. before and after the 72-hour hold and indicated that the solids were of crystalline Form B of the L-tartrate salt of 2-{4'-[(3aR,6aR)-5-methylhexahydropyrrolo[3,4-b]pyrrol-1(2H)-yl]-1,1-biphenyl-4-yl}pyridazin-3(2H)-one.

Example G

Crystallization of Form B of L-tartrate salt of 2-{4'-[(3aR,6aR)-5-Methylhexahydropyrrolo[3,4-b]pyrrol-1(2H)-yl]-1,1'-biphenyl-4-yl}pyridazin-3(2H)-one 2-{4'-[(3aR,6aR)-5-Methylhexahydropyrrolo[3,4-b]pyrrol-1(2H)-yl]-1,1'-biphenyl-4-yl}pyridazin-3(2H)-one (free base, 3.12 grams), 1.5 grams of L-tartaric acid and 15 mL each of absolute ethanol and water were added to a 50 mL jacketed reactor and heated to 76° C. while stirring at 250 rpm to affect a clear solution. Once all the solids had dissolved, the reactor was cooled to 60° C. at 5° C./hour and then held at 60° C. for 3 hours. After the 3 hour hold, the reactor was cooled to 20° C. at 10° C./hour. The reactor was stirred continuously at 20° C. for 24 hours. The slurry was discharged onto a medium frit sintered glass filtration funnel. Solids were washed with 15 mLs of de-ionized water and then air-dried 30 minutes. PXRD analysis of the solids indicated that the solids were of the crystalline Form B of the L-tartrate salt of 2-{4'-[(3aR,6aR)-5-methylhexahydropyrrolo[3,4-b]pyrrol-1(2H)-yl]-1,1'-biphenyl-4-yl}pyridazin-3(2H)-one.

Example H

Crystallization of Form A of L-tartrate salt of 2-{4'-[(3aR,6aR)-5-Methylhexahydropyrrolo[3,4-b]pyrrol-1(2H)-yl]-1,1'-biphenyl-4-yl}pyridazin-3(2H)-one 2-{4'-[(3aR,6aR)-5-Methylhexahydropyrrolo[3,4-b]pyrrol-1(2H)-yl]-1,1'-biphenyl-4-yl}pyridazin-3(2H)-one (free base, 1.74 g) was dissolved in 25 mLs of dimethyl acetamide by heating to 75° C. in a 50 mL jacketed reactor equipped with overhead stirring motor. A solution of L-tartaric acid in water was prepared by dissolving 549 mg of L-tartaric acid in 15 mL of de-ionized water by mixing at 25+/−5% ° C. The L-tartaric acid solution was slowly added to the hot free base solution, while maintaining the temperature of the free base solution at 75° C. The temperature of the solution was held at 75° C. for 20 minutes. The reactor was cooled to 47° C. The reactor was held at 47° C. for 30 minutes and then continued cool to 20° C. Once the reactor reached 20° C., a sample was collected from the reactor for PXRD. The reactor was stirred for another 24 hours. The slurry was discharged onto a medium frit sintered glass filtration funnel. The cake was washed with 18 mL of a 50/50 v/v mixture of de-ionized water and methanol. Solids were air-dried on the filter for 3 hours. PXRD analysis on the solids collected after at 20° C. before and after the 24-hour hold and indicated that the solids were of crystalline Form A of the L-tartrate salt of 2-{4'-[(3aR,6aR)-5-methylhexahydropyrrolo[3,4-b]pyrrol-1(2H)-yl]-1,1'-biphenyl-4-yl}pyridazin-3(2H)-one.

Example I

2-{4'-[(3aR,6aR)-5-Methylhexahydropyrrolo[3,4-b]pyrrol-1(2H)-yl]-1,1'-biphenyl-4-yl}pyridazin-3(2H)-one L-tartrate anhydrate 2-{4'-[(3aR,6aR)-5-Methylhexahydropyrrolo[3,4-b]pyrrol-1(2H)-yl]-1,1'-biphenyl-4-yl}pyridazin-3(2H)-one (free base, 37.4 mg) was dissolved in 300 micro liters of dichloromethane by stirring at 25° C. with a magnetic bead in a 4 mL vial. A solution of L-tartaric acid in methanol was prepared by dissolving 18.2 mg of L-tartaric acid in 200 micro liters of methanol by mixing at 25+/−5% ° C. The L-tartaric acid solution was slowly added to the free base solution, while stirring. The reactor was stirred for 3 hours. The slurry was discharged onto a medium frit sintered glass filtration funnel. Solids were air-dried on the filter for 30 minutes. PXRD analysis on the solids indicated that the solids were of crystalline anhydrous form of the L-tartrate salt of 2-{4'-[(3aR,6aR)-5-methylhexahydropyrrolo[3,4-b]pyrrol-1(2H)-yl]-1,1'-biphenyl-4-yl}pyridazin-3(2H)-one.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. Crystalline 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form A demonstrating at least one characteristic peak in the powder X-ray diffraction pattern at values of two theta of 3.90±0.2, 16.72±0.2, 16.99±0.2, 17.17±0.2, 18.12±0.2, 19.72±0.2, 19.98±0.2, 20.25±0.2, 23.96±0.2, 27.65±0.2, and 28.93±0.2.

2. Crystalline 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form B demonstrating at least one characteristic peak in the powder X-ray diffraction pattern at values of two theta of 4.39±0.2, 10.45±0.2, 11.92±0.2, 12.52±0.2, 13.45±0.2, 16.71±0.2, 16.92±0.2, 17.62±0.2, 7.90±0.2, 19.10±0.2, 20.46±0.2, and 20.63±0.2.

3. Crystalline 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride trihemihydrate demonstrating at least one characteristic peak in the powder X-ray diffraction pattern at values of two theta of 4.03±0.2, 13.92±0.2, 15.55±0.2, 15.61±0.2, 15.93±0.2, 16.15±0.2, 24.37±0.2, 24.66±0.2, 25.12±0.2, 25.68±0.2, and 27.90±0.2.

4. Crystalline 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate anhydrate demonstrating at least one characteristic peak in the powder X-ray diffraction pattern at values of two theta of 4.34±0.2, 8.69±0.2, 13.04±0.2, 15.82±0.2, 17.11±0.2, 18.35±0.2, 18.93±0.2, 20.74±0.2, 22.40±0.2, 23.04±0.2, and 26.45±0.2.

5. Crystalline 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride anhydrate demonstrating at least one characteristic peak in the powder X-ray diffraction pattern at values of two theta of 6.27±0.2, 12.59±0.2, 15.15±0.2, 16.71±0.2, 18.49±0.2, 18.95±0.2, 20.31±0.2, 20.97±0.2, 22.44±0.2, 23.82±0.2, 24.03±0.2, 24.67±0.2, 31.90±0.2, and 32.75±0.2.

6. Substantially pure crystalline 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form A.

7. Substantially pure crystalline 2-{4'-[(3aR,6aR)-5-methylhexylhydropyrrolo[3,4-b]pyrrol-1(2)-yl]-1,1'-biphenyl-4-yl}pyridazin 3(2H)-one L-tartrate monohydrate Form B.

8. Substantially pure crystalline 2-{4'-[(3aR,6aR)-5-methylhexahydropyrrolo[3,4-b]pyrrol-1(2H)-yl]-1,1'-biphenyl-4-yl}pyridazin-3(2H)-one hydrochloride trihemihydrate.

9. Substantially pure crystalline 2-{4'-[(3aR,6aR)-5-methylhexahydropyrrolo[3,4-b]pyrrol-1(2H)-yl]-1,1'-biphenyl-4-yl}pyridazin-3(2H)-L-tartrate anhydrate.

10. Substantially pure crystalline 2-{4'-[(3aR,6aR)-5-methylhexahydropyrrolo[3,4-b]pyrrol-1(2H)-yl]-1,1-biphenyl-4-yl}pyridazin-3(2H)-one hydrochloride anhydrate.

11. Crystalline 2-{4'-[(3aR,6aR)-5-methylhexahydropyrrolo[3,4-b]pyrrol-1(2H)-yl]-1,1'-biphenyl-4-yl}pyridazin-3(2H)-one L-tartrate monohydrate Form A having the unit cell parameters wherein a is 7.6 Å, b is 7.4 Å, c is 22.7 Å and β is 94.1°.

12. Crystalline 2-{4'-[(3aR,6aR)-5-methylhexahydropyrrolo[3,4-b]pyrrol-1(2H)-yl]-1,1'-biphenyl-4-yl}pyridazin-3(2)-one L-tartrate monohydrate Form B having the unit cell parameters wherein a is 7.6 Å, b is 8.7 Å, c is 40.3 Å.

13. Crystalline 2-{4-[(3aR,6aR)-5-methylhexahydropyrrolo[3,4-b]pyrrol-1(2H)-yl]-1,1'-biphenyl-4-yl}pyridazin-3(2H)-one hydrochloride trihemihydrate having the unit cell parameters wherein a is 7.3 Å, b is 7.4 Å, c is 22.2 Å and α, β, γ are each respectively 86.3°, 81.0°, and 77.3°.

14. A process for preparing 2-{4'-[(3aR,6aR)-5-methylhexahydropyrrolo[3,4-b]pyrrol-1(2H)-yl]-1,1'-biphenyl-4-yl}pyridazin-3(2H)-one comprising recrystallizing 2-{4'-[(3aR,6aR)-5-methylhexahydropyrrolo[3,4-b]pyrrol-1(2H)-yl]-1,1-biphenyl-4-yl}pyridazin-3(2H)-one L-tartrate salt in water and dimethyl acetamide or ethanol.

* * * * *